(12) United States Patent
Bramhill et al.

(10) Patent No.: US 9,156,917 B2
(45) Date of Patent: Oct. 13, 2015

(54) CH2 DOMAIN TEMPLATE MOLECULES DERIVED FROM RATIONAL GRAFTING OF DONOR LOOPS ONTO CH2 SCAFFOLDS

(75) Inventors: David Bramhill, Tucson, AZ (US); Gopalan Raghunathan, San Diego, CA (US)

(73) Assignee: RESEARCH CORPORATION TECHNOLOGIES, INC., Tucson, AZ (US)

( * ) Notice: Subject to any disclaimer, the term of this patent is extended or adjusted under 35 U.S.C. 154(b) by 0 days.

(21) Appl. No.: 13/370,831

(22) Filed: Feb. 10, 2012

(65) Prior Publication Data

US 2012/0230981 A1    Sep. 13, 2012

Related U.S. Application Data

(60) Provisional application No. 61/441,967, filed on Feb. 11, 2011.

(51) Int. Cl.
| | |
|---|---|
| *C07K 16/46* | (2006.01) |
| *C07K 16/00* | (2006.01) |
| *C07K 16/42* | (2006.01) |
| *C40B 30/04* | (2006.01) |
| *G01N 33/68* | (2006.01) |

(52) U.S. Cl.
CPC ........... *C07K 16/461* (2013.01); *C07K 16/005* (2013.01); *C07K 16/42* (2013.01); *C40B 30/04* (2013.01); *G01N 33/6854* (2013.01); *C07K 2317/524* (2013.01); *C07K 2317/92* (2013.01); *C07K 2317/94* (2013.01)

(58) Field of Classification Search
CPC ................................................ C07K 2317/524
See application file for complete search history.

(56) References Cited

U.S. PATENT DOCUMENTS

| | | | | |
|---|---|---|---|---|
| 8,198,413 | B2 * | 6/2012 | Haeuw | ....................... 530/387.3 |
| 8,580,927 | B2 | 11/2013 | Dimitrov | |
| 2009/0118127 | A1 | 5/2009 | Raghunathan | |
| 2009/0298195 | A1 | 12/2009 | Rüker et al. | |
| 2010/0074901 | A1 | 3/2010 | Mercken et al. | |
| 2010/0272720 | A1 | 10/2010 | Lo et al. | |
| 2010/0316641 | A1 | 12/2010 | Dimitrov | |
| 2011/0118131 | A1 * | 5/2011 | Takeuchi | ......................... 506/7 |

FOREIGN PATENT DOCUMENTS

| | | |
|---|---|---|
| WO | 2006/072620 A1 | 7/2006 |
| WO | 2008/003103 A2 | 1/2008 |
| WO | 2009/058379 A2 | 5/2009 |
| WO | 2009/099961 A2 | 8/2009 |
| WO | 2010/065578 | 6/2010 |

OTHER PUBLICATIONS

Bowie, et al. Science, vol. 247: 1306-1310, 1990.*
Lazar, et al. Mol. Cell. Biol., 8(3): 1247-1252, 1988.*
Burgess, et al. J. Cell Biol. 111: 2129-2138, 1990.*
Ngo et al., in"The Protein Folding Problem and Tediary Structure Prediction", 1994, Merz, et al. (ed.), Birkhauser, Boston, MA, pp. 433, and 492-495.*
Paul, Fundamental Immunology, 3rd Edition, 1993, pp. 292-295.*
Rudikoff et al., Proc. Natl. Acad. Sci. USA, 79(6):1979-1983, Mar. 1982.*
Colman, Research in Immunology, 145:33-36, 1994.*
Bendig, Methods: A Companion to Methods in Enzymology, 1995; 8:83-93.*
Xiao, X. et al., "A large library based on a novel (CH2) scaffold: Identification of HIV-1 inhibitors" Biochemical and Biophysical Research Communications (Sep. 2009) pp. 387-392, vol. 387, No. 2.
Dimitrov, D.S., "Engineered CH2 domains (nanoantibodies)" Landes Bioscience (Jan./Feb. 2009) pp. 26-28, vol. 1, No. 1.
Gong, R. et al., "Engineered Human Antibody Constant Domains with Increased Stability" The Journal of Biological Chemistry (May 2009) pp. 14203-14210, vol. 284, No. 22.
Supplementary European Search Report dated Jun. 5, 2015 issued in European Application No. EP 12744675.5.

* cited by examiner

*Primary Examiner* — Hong Sang
(74) *Attorney, Agent, or Firm* — Scully, Scott, Murphy & Presser, P.C.

(57) ABSTRACT

Novel CH2 domain template molecules wherein donor loops from a database of domains are transferred to a CH2 domain scaffold. At least one or up to three loops from a donor are transferred to the CH2 domain. The donor loops may be chosen based on length, e.g., the donor loop may have a length that is similar to that of a structural loop in the CH2 domain scaffold.

1 Claim, 6 Drawing Sheets

SEQUENCE LISTING

<160> NUMBER OF SEQ ID NOS: 160

<210> SEQ ID NO 1
<211> LENGTH: 112
<212> TYPE: PRT

<213> ORGANISM: Homo sapiens

<400> SEQUENCE: 1

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

<210> SEQ ID NO 2
<211> LENGTH: 10
<212> TYPE: PRT
<213> ORGANISM: Homo sapiens

<400> SEQUENCE: 2

Asp Val Ser His Glu Asp Pro Glu Val Lys
1               5                   10

<210> SEQ ID NO 3
<211> LENGTH: 9
<212> TYPE: PRT
<213> ORGANISM: Homo sapiens

<400> SEQUENCE: 3

Ser Asn Lys Ala Leu Pro Ala Pro Ile
1               5

<210> SEQ ID NO 4
<211> LENGTH: 6
<212> TYPE: PRT
<213> ORGANISM: Homo sapiens

<400> SEQUENCE: 4

Glu Glu Gln Tyr Asn Ser
1               5

<210> SEQ ID NO 5
<211> LENGTH: 4
<212> TYPE: PRT
<213> ORGANISM: Artificial Sequence
<220> FEATURE:
<223> OTHER INFORMATION: Example of variant L2 loop sequence for CH2
      molecule
<220> FEATURE:
<221> NAME/KEY: VARIANT
<222> LOCATION: (1)..(4)

<400> SEQUENCE: 5

Glu Glu His Asn
1

<210> SEQ ID NO 6
<211> LENGTH: 5
<212> TYPE: PRT

```
<213> ORGANISM: Artificial Sequence
<220> FEATURE:
<223> OTHER INFORMATION: Example of variant L2 loop sequence for CH2
      molecule
<220> FEATURE:
<221> NAME/KEY: VARIANT
<222> LOCATION: (1)..(5)

<400> SEQUENCE: 6

Glu Glu Ala Ala Ser
1               5

<210> SEQ ID NO 7
<211> LENGTH: 6
<212> TYPE: PRT
<213> ORGANISM: Artificial Sequence
<220> FEATURE:
<223> OTHER INFORMATION: Example of variant L2 loop sequence for CH2
      molecule
<220> FEATURE:
<221> NAME/KEY: VARIANT
<222> LOCATION: (1)..(6)

<400> SEQUENCE: 7

Glu Glu Tyr Asp Thr Ser
1               5

<210> SEQ ID NO 8
<211> LENGTH: 6
<212> TYPE: PRT
<213> ORGANISM: Artificial Sequence
<220> FEATURE:
<223> OTHER INFORMATION: Example of variant L2 loop sequence for CH2
      molecule
<220> FEATURE:
<221> NAME/KEY: VARIANT
<222> LOCATION: (1)..(6)

<400> SEQUENCE: 8

Val Tyr Pro Gly Ser Ile
1               5

<210> SEQ ID NO 9
<211> LENGTH: 7
<212> TYPE: PRT
<213> ORGANISM: Artificial Sequence
<220> FEATURE:
<223> OTHER INFORMATION: Example of variant L2 loop sequence for CH2
      molecule
<220> FEATURE:
<221> NAME/KEY: VARIANT
<222> LOCATION: (1)..(7)

<400> SEQUENCE: 9

Ile Tyr Trp Asp Asp Lys
1               5

<210> SEQ ID NO 10
<211> LENGTH: 8
<212> TYPE: PRT
<213> ORGANISM: Artificial Sequence
<220> FEATURE:
<223> OTHER INFORMATION: Example of variant L2 loop sequence for CH2
      molecule
<220> FEATURE:
<221> NAME/KEY: VARIANT
<222> LOCATION: (1)..(8)

<400> SEQUENCE: 10

Ile Ser Ser Ser Gly Asp Pro Thr
```

```
<210> SEQ ID NO 11
<211> LENGTH: 10
<212> TYPE: PRT
<213> ORGANISM: Artificial Sequence
<220> FEATURE:
<223> OTHER INFORMATION: Example of variant L1 loop sequence for CH2
      molecule
<220> FEATURE:
<221> NAME/KEY: VARIANT
<222> LOCATION: (1)..(10)

<400> SEQUENCE: 11

Gly Phe Ser Leu Ser Thr Tyr Gly Met Gly
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Example of variant L1 loop sequence for CH2
      molecule
<220> FEATURE:
<221> NAME/KEY: VARIANT
<222> LOCATION: (1)..(10)

<400> SEQUENCE: 12

Lys Ser Val Ser Thr Ser Gly Tyr Ser Tyr
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Example of variant L1 loop sequence for CH2
      molecule
<220> FEATURE:
<221> NAME/KEY: VARIANT
<222> LOCATION: (1)..(10)

<400> SEQUENCE: 13

Gly Phe Ser Leu Ser Thr Ser Gly Met Gly
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Example of variant L1 loop sequence for CH2
      molecule
<220> FEATURE:
<221> NAME/KEY: VARIANT
<222> LOCATION: (1)..(10)

<400> SEQUENCE: 14

Gln Ser Val Asp Tyr Asn Gly Asp Ser Tyr
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Example of variant L1 loop sequence for CH2
      molecule
<220> FEATURE:
```

```
-continued

<221> NAME/KEY: VARIANT
<222> LOCATION: (1)..(10)

<400> SEQUENCE: 15

Gly Gly Ser Ile Arg Ser Gly Gly Tyr Tyr
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Example of variant L1 loop sequence for CH2
      molecule
<220> FEATURE:
<221> NAME/KEY: VARIANT
<222> LOCATION: (1)..(10)

<400> SEQUENCE: 16

Lys Ser Val Ser Thr Ser Gly Tyr Asn Tyr
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Example of variant L1 loop sequence for CH2
      molecule
<220> FEATURE:
<221> NAME/KEY: VARIANT
<222> LOCATION: (1)..(9)

<400> SEQUENCE: 17

Gly Tyr Ser Ile Thr Ser Asp Tyr Ala
1               5

<210> SEQ ID NO 18
<211> LENGTH: 9
<212> TYPE: PRT
<213> ORGANISM: Artificial Sequence
<220> FEATURE:
<223> OTHER INFORMATION: Example of variant L1 loop sequence for CH2
      molecule
<220> FEATURE:
<221> NAME/KEY: VARIANT
<222> LOCATION: (1)..(9)

<400> SEQUENCE: 18

Ser Arg Asp Val Gly Gly Tyr Asn Tyr
1               5

<210> SEQ ID NO 19
<211> LENGTH: 9
<212> TYPE: PRT
<213> ORGANISM: Artificial Sequence
<220> FEATURE:
<223> OTHER INFORMATION: Example of variant L1 loop sequence for CH2
      molecule
<220> FEATURE:
<221> NAME/KEY: VARIANT
<222> LOCATION: (1)..(9)

<400> SEQUENCE: 19

Gly Tyr Ser Ile Thr Ser Asp Phe Ala
1               5

<210> SEQ ID NO 20
<211> LENGTH: 9
```

```
<212> TYPE: PRT
<213> ORGANISM: Artificial Sequence
<220> FEATURE:
<223> OTHER INFORMATION: Example of variant L1 loop sequence for CH2
      molecule
<220> FEATURE:
<221> NAME/KEY: VARIANT
<222> LOCATION: (1)..(9)

<400> SEQUENCE: 20

Ser Ser Asn Ile Gly Ala Gly Tyr Asp
1               5

<210> SEQ ID NO 21
<211> LENGTH: 9
<212> TYPE: PRT
<213> ORGANISM: Artificial Sequence
<220> FEATURE:
<223> OTHER INFORMATION: Example of variant L1 loop sequence for CH2
      molecule
<220> FEATURE:
<221> NAME/KEY: VARIANT
<222> LOCATION: (1)..(9)

<400> SEQUENCE: 21

Gly Tyr Ser Ile Ser Ser Asp Tyr Ala
1               5

<210> SEQ ID NO 22
<211> LENGTH: 10
<212> TYPE: PRT
<213> ORGANISM: Artificial Sequence
<220> FEATURE:
<223> OTHER INFORMATION: Example of variant L1 loop sequence for CH2
      molecule
<220> FEATURE:
<221> NAME/KEY: VARIANT
<222> LOCATION: (1)..(10)

<400> SEQUENCE: 22

Gly Phe Ser Leu Ser Thr Ser Gly Met Ser
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Example of variant L1 loop sequence for CH2
      molecule
<220> FEATURE:
<221> NAME/KEY: VARIANT
<222> LOCATION: (1)..(10)

<400> SEQUENCE: 23

Gly Phe Ser Leu Ser Thr Tyr Gly Val Gly
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Example of variant L1 loop sequence for CH2
      molecule
<220> FEATURE:
<221> NAME/KEY: VARIANT
<222> LOCATION: (1)..(10)

<400> SEQUENCE: 24
```

```
Gly Phe Ser Leu Thr Thr Tyr Gly Met Gly
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Example of variant L1 loop sequence for CH2
      molecule
<220> FEATURE:
<221> NAME/KEY: VARIANT
<222> LOCATION: (1)..(10)

<400> SEQUENCE: 25

Gly Phe Ser Ile Arg Thr Ser Lys Val Gly
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Example of variant L1 loop sequence for CH2
      molecule
<220> FEATURE:
<221> NAME/KEY: VARIANT
<222> LOCATION: (1)..(10)

<400> SEQUENCE: 26

Gly Phe Ser Leu Ser Asp Phe Gly Val Gly
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Example of variant L1 loop sequence for CH2
      molecule
<220> FEATURE:
<221> NAME/KEY: VARIANT
<222> LOCATION: (1)..(12)

<400> SEQUENCE: 27

Ala Arg Arg Thr Thr Thr Ala Asp Tyr Phe Ala Tyr
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Example of variant L1 loop sequence for CH2
      molecule
<220> FEATURE:
<221> NAME/KEY: VARIANT
<222> LOCATION: (1)..(13)

<400> SEQUENCE: 28

Ala Arg Leu Gly Ser Asp Tyr Asp Val Trp Phe Asp Tyr
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Example of variant L1 loop sequence for CH2
      molecule
```

```
<220> FEATURE:
<221> NAME/KEY: VARIANT
<222> LOCATION: (1)..(14)

<400> SEQUENCE: 29

Ala Arg Arg Ala Pro Phe Tyr Gly Asn His Ala Met Asp Tyr
1               5                   10

<210> SEQ ID NO 30
<211> LENGTH: 15
<212> TYPE: PRT
<213> ORGANISM: Artificial Sequence
<220> FEATURE:
<223> OTHER INFORMATION: Example of variant L1 loop sequence for CH2
      molecule
<220> FEATURE:
<221> NAME/KEY: VARIANT
<222> LOCATION: (1)..(15)

<400> SEQUENCE: 30

Val Arg Arg Ala His Thr Thr Val Leu Gly Asp Trp Phe Ala Tyr
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Example of variant L1 loop sequence for CH2
      molecule
<220> FEATURE:
<221> NAME/KEY: VARIANT
<222> LOCATION: (1)..(16)

<400> SEQUENCE: 31

Ala Arg Thr Leu Arg Val Ser Gly Asp Tyr Val Arg Asp Phe Asp Leu
1               5                   10                  15

<210> SEQ ID NO 32
<211> LENGTH: 17
<212> TYPE: PRT
<213> ORGANISM: Artificial Sequence
<220> FEATURE:
<223> OTHER INFORMATION: Example of variant L1 loop sequence for CH2
      molecule
<220> FEATURE:
<221> NAME/KEY: VARIANT
<222> LOCATION: (1)..(17)

<400> SEQUENCE: 32

Ala Arg Arg Gly Phe Tyr Gly Arg Lys Tyr Glu Val Asn His Phe Asp
1               5                   10                  15

Tyr

<210> SEQ ID NO 33
<211> LENGTH: 18
<212> TYPE: PRT
<213> ORGANISM: Artificial Sequence
<220> FEATURE:
<223> OTHER INFORMATION: Example of variant L1 loop sequence for CH2
      molecule
<220> FEATURE:
<221> NAME/KEY: VARIANT
<222> LOCATION: (1)..(18)

<400> SEQUENCE: 33

Ala Arg Arg Thr Phe Ser Tyr Tyr Tyr Gly Ser Ser Phe Tyr Tyr Phe
1               5                   10                  15
```

Asp Asn

<210> SEQ ID NO 34
<211> LENGTH: 24
<212> TYPE: PRT
<213> ORGANISM: Artificial Sequence
<220> FEATURE:
<223> OTHER INFORMATION: Example of variant L1 loop sequence for CH2
      molecule
<220> FEATURE:
<221> NAME/KEY: VARIANT
<222> LOCATION: (1)..(24)

<400> SEQUENCE: 34

Ala His Arg Arg Gly Pro Thr Thr Leu Phe Gly Val Pro Ile Ala Arg
1               5                   10                  15

Gly Pro Val Asn Ala Met Asp Val
            20

<210> SEQ ID NO 35
<211> LENGTH: 7
<212> TYPE: PRT
<213> ORGANISM: Artificial Sequence
<220> FEATURE:
<223> OTHER INFORMATION: Example of variant L3 loop sequence for CH2
      molecule
<220> FEATURE:
<221> NAME/KEY: VARIANT
<222> LOCATION: (1)..(7)

<400> SEQUENCE: 35

Val Gln Glu Gly Tyr Ile Tyr
1               5

<210> SEQ ID NO 36
<211> LENGTH: 8
<212> TYPE: PRT
<213> ORGANISM: Artificial Sequence
<220> FEATURE:
<223> OTHER INFORMATION: Example of variant L3 loop sequence for CH2
      molecule
<220> FEATURE:
<221> NAME/KEY: VARIANT
<222> LOCATION: (1)..(8)

<400> SEQUENCE: 36

Gln His Ser Arg Glu Leu Leu Thr
1               5

<210> SEQ ID NO 37
<211> LENGTH: 9
<212> TYPE: PRT
<213> ORGANISM: Artificial Sequence
<220> FEATURE:
<223> OTHER INFORMATION: Example of variant L3 loop sequence for CH2
      molecule
<220> FEATURE:
<221> NAME/KEY: VARIANT
<222> LOCATION: (1)..(9)

<400> SEQUENCE: 37

Thr Leu Tyr Tyr Gly Ser Val Asp Tyr
1               5

<210> SEQ ID NO 38
<211> LENGTH: 9
<212> TYPE: PRT
<213> ORGANISM: Artificial Sequence
<220> FEATURE:

```
<223> OTHER INFORMATION: Example of variant L3 loop sequence for CH2
      molecule
<220> FEATURE:
<221> NAME/KEY: VARIANT
<222> LOCATION: (1)..(9)

<400> SEQUENCE: 38

Gln Gln Ser Asn Glu Asp Pro Phe Thr
1               5

<210> SEQ ID NO 39
<211> LENGTH: 10
<212> TYPE: PRT
<213> ORGANISM: Artificial Sequence
<220> FEATURE:
<223> OTHER INFORMATION: Example of variant L3 loop sequence for CH2
      molecule
<220> FEATURE:
<221> NAME/KEY: VARIANT
<222> LOCATION: (1)..(10)

<400> SEQUENCE: 39

Ala Arg Leu Asp Gly Tyr Thr Leu Asp Ile
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Example of variant L3 loop sequence for CH2
      molecule
<220> FEATURE:
<221> NAME/KEY: VARIANT
<222> LOCATION: (1)..(10)

<400> SEQUENCE: 40

Leu Tyr Ser Arg Glu Phe Pro Pro Trp Thr
1               5                   10

<210> SEQ ID NO 41
<211> LENGTH: 8
<212> TYPE: PRT
<213> ORGANISM: Artificial Sequence
<220> FEATURE:
<223> OTHER INFORMATION: Example of variant L3 loop sequence for CH2
      molecule
<220> FEATURE:
<221> NAME/KEY: VARIANT
<222> LOCATION: (1)..(8)

<400> SEQUENCE: 41

Ala Arg Gly Trp Pro Leu Ala Tyr
1               5

<210> SEQ ID NO 42
<211> LENGTH: 9
<212> TYPE: PRT
<213> ORGANISM: Artificial Sequence
<220> FEATURE:
<223> OTHER INFORMATION: Example of variant L3 loop sequence for CH2
      molecule
<220> FEATURE:
<221> NAME/KEY: VARIANT
<222> LOCATION: (1)..(9)

<400> SEQUENCE: 42

Trp Ser Phe Ala Gly Ser Tyr Tyr Val
1               5
```

```
<210> SEQ ID NO 43
<211> LENGTH: 9
<212> TYPE: PRT
<213> ORGANISM: Artificial Sequence
<220> FEATURE:
<223> OTHER INFORMATION: Example of variant L3 loop sequence for CH2
      molecule
<220> FEATURE:
<221> NAME/KEY: VARIANT
<222> LOCATION: (1)..(9)

<400> SEQUENCE: 43

Ala Thr Ala Gly Arg Gly Phe Pro Tyr
1               5

<210> SEQ ID NO 44
<211> LENGTH: 11
<212> TYPE: PRT
<213> ORGANISM: Artificial Sequence
<220> FEATURE:
<223> OTHER INFORMATION: Example of variant L3 loop sequence for CH2
      molecule
<220> FEATURE:
<221> NAME/KEY: VARIANT
<222> LOCATION: (1)..(11)

<400> SEQUENCE: 44

Gln Ser Tyr Asp Ser Ser Leu Ser Gly Ser Val
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Example of variant L3 loop sequence for CH2
      molecule
<220> FEATURE:
<221> NAME/KEY: VARIANT
<222> LOCATION: (1)..(11)

<400> SEQUENCE: 45

Ala Ser Tyr Asp Asp Tyr Thr Trp Phe Thr Tyr
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Example of variant L3 loop sequence for CH2
      molecule
<220> FEATURE:
<221> NAME/KEY: VARIANT
<222> LOCATION: (1)..(12)

<400> SEQUENCE: 46

Ala Arg Gly Tyr Tyr Gly Ser Ser His Ser Pro Val
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Example of variant L3 loop sequence for CH2
      molecule
<220> FEATURE:
<221> NAME/KEY: VARIANT
<222> LOCATION: (1)..(14)
```

<400> SEQUENCE: 47

Ala Arg Arg Ala Pro Phe Tyr Gly Asn His Ala Met Asp Tyr
1               5                   10

<210> SEQ ID NO 48
<211> LENGTH: 112
<212> TYPE: PRT
<213> ORGANISM: Artificial Sequence
<220> FEATURE:
<223> OTHER INFORMATION: CH2 domain molecule with additional disulfide
      bond
<220> FEATURE:
<221> NAME/KEY: DISULFID
<222> LOCATION: (10)..(102)

<400> SEQUENCE: 48

Ala Pro Glu Leu Leu Gly Gly Pro Ser Cys Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Cys Glu Lys Thr Ile Ser Lys Ala Lys Gly Gln
            100                 105                 110

<210> SEQ ID NO 49
<211> LENGTH: 112
<212> TYPE: PRT
<213> ORGANISM: Artificial Sequence
<220> FEATURE:
<223> OTHER INFORMATION: CH2 domain molecule with additional disulfide
      bond
<220> FEATURE:
<221> NAME/KEY: DISULFID
<222> LOCATION: (9)..(102)

<400> SEQUENCE: 49

Ala Pro Glu Leu Leu Gly Gly Pro Cys Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Cys Glu Lys Thr Ile Ser Lys Ala Lys Gly Gln
            100                 105                 110

<210> SEQ ID NO 50
<211> LENGTH: 112

```
<212> TYPE: PRT
<213> ORGANISM: Artificial Sequence
<220> FEATURE:
<223> OTHER INFORMATION: CH2 domain molecule with additional disulfide
      bond
<220> FEATURE:
<221> NAME/KEY: DISULFID
<222> LOCATION: (14)..(106)

<400> SEQUENCE: 50

Ala Pro Glu Leu Leu Gly Gly Pro Ser Val Phe Leu Phe Cys Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Cys Ser Lys Ala Lys Gly Gln
            100                 105                 110

<210> SEQ ID NO 51
<211> LENGTH: 112
<212> TYPE: PRT
<213> ORGANISM: Artificial Sequence
<220> FEATURE:
<223> OTHER INFORMATION: CH2 domain molecule with additional disulfide
      bond
<220> FEATURE:
<221> NAME/KEY: DISULFID
<222> LOCATION: (12)..(104)

<400> SEQUENCE: 51

Ala Pro Glu Leu Leu Gly Gly Pro Ser Val Phe Cys Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Cys Thr Ile Ser Lys Ala Lys Gly Gln
            100                 105                 110

<210> SEQ ID NO 52
<211> LENGTH: 112
<212> TYPE: PRT
<213> ORGANISM: Artificial Sequence
<220> FEATURE:
<223> OTHER INFORMATION: CH2 domain molecule with additional disulfide
      bond
<220> FEATURE:
<221> NAME/KEY: DISULFID
<222> LOCATION: (10)..(104)
```

```
<400> SEQUENCE: 52

Ala Pro Glu Leu Leu Gly Gly Pro Ser Cys Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Cys Thr Ile Ser Lys Ala Lys Gly Gln
            100                 105                 110

<210> SEQ ID NO 53
<211> LENGTH: 112
<212> TYPE: PRT
<213> ORGANISM: Artificial Sequence
<220> FEATURE:
<223> OTHER INFORMATION: CH2 domain molecule with additional disulfide
      bond
<220> FEATURE:
<221> NAME/KEY: DISULFID
<222> LOCATION: (63)..(71)

<400> SEQUENCE: 53

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Cys Glu
    50                  55                  60

Gln Tyr Asn Ser Thr Tyr Cys Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

<210> SEQ ID NO 54
<211> LENGTH: 105
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (60)..(61)

<400> SEQUENCE: 54

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Asp Val Ser
            20                  25                  30

His Glu Asp Pro Glu Val Lys Phe Asn Trp Tyr Val Asp Gly Val Glu
        35                  40                  45
```

```
Val His Asn Ala Lys Thr Lys Pro Arg Glu Glu His Asn Thr Tyr Arg
    50                  55                  60

Val Val Ser Val Leu Thr Val Leu His Gln Asp Trp Leu Asn Gly Lys
 65                  70                  75                  80

Glu Tyr Lys Cys Lys Val Ser Asn Lys Ala Leu Pro Ala Pro Ile Glu
                85                  90                  95

Lys Thr Ile Ser Lys Ala Lys Gly Gln
            100                 105

<210> SEQ ID NO 55
<211> LENGTH: 106
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (56)..(64)

<400> SEQUENCE: 55

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Asp Val Ser
                20                  25                  30

His Glu Asp Pro Glu Val Lys Phe Asn Trp Tyr Val Asp Gly Val Glu
            35                  40                  45

Val His Asn Ala Lys Thr Lys Pro Arg Glu Glu Ala Ala Ser Thr Tyr
 50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln
            100                 105

<210> SEQ ID NO 56
<211> LENGTH: 107
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (56)..(65)

<400> SEQUENCE: 56

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Asp Val Ser
                20                  25                  30

His Glu Asp Pro Glu Val Lys Phe Asn Trp Tyr Val Asp Gly Val Glu
            35                  40                  45

Val His Asn Ala Lys Thr Lys Pro Arg Glu Glu Tyr Asp Thr Ser Thr
 50                  55                  60

Tyr Arg Val Val Ser Val Leu Thr Val Leu His Gln Asp Trp Leu Asn
65                  70                  75                  80

Gly Lys Glu Tyr Lys Cys Lys Val Ser Asn Lys Ala Leu Pro Ala Pro
                85                  90                  95

Ile Glu Lys Thr Ile Ser Lys Ala Lys Gly Gln
            100                 105
```

<210> SEQ ID NO 57
<211> LENGTH: 107
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (56)..(65)

<400> SEQUENCE: 57

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Asp Val Ser
            20                  25                  30

His Glu Asp Pro Glu Val Lys Phe Asn Trp Tyr Val Asp Gly Val Glu
        35                  40                  45

Val His Asn Ala Lys Thr Lys Pro Arg Val Tyr Pro Gly Ser Ile Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Ser Asn Lys Ala Leu Pro Ala Pro
                85                  90                  95

Ile Glu Lys Thr Ile Ser Lys Ala Lys Gly Gln
            100                 105

<210> SEQ ID NO 58
<211> LENGTH: 108
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (56)..(66)

<400> SEQUENCE: 58

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Asp Val Ser
            20                  25                  30

His Glu Asp Pro Glu Val Lys Phe Asn Trp Tyr Val Asp Gly Val Glu
        35                  40                  45

Val His Asn Ala Lys Thr Lys Pro Arg Ile Tyr Trp Asp Asp Asp Lys
    50                  55                  60

Thr Tyr Arg Val Val Ser Val Leu Thr Val Leu His Gln Asp Trp Leu
65                  70                  75                  80

Asn Gly Lys Glu Tyr Lys Cys Lys Val Ser Asn Lys Ala Leu Pro Ala
                85                  90                  95

Pro Ile Glu Lys Thr Ile Ser Lys Ala Lys Gly Gln
            100                 105

<210> SEQ ID NO 59
<211> LENGTH: 109
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT

<222> LOCATION: (56)..(67)

<400> SEQUENCE: 59

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Asp Val Ser
            20                  25                  30

His Glu Asp Pro Glu Val Lys Phe Asn Trp Tyr Val Asp Gly Val Glu
        35                  40                  45

Val His Asn Ala Lys Thr Lys Pro Arg Ile Ser Ser Ser Gly Asp Pro
    50                  55                  60

Thr Thr Tyr Arg Val Val Ser Val Leu Thr Val Leu His Gln Asp Trp
65                  70                  75                  80

Leu Asn Gly Lys Glu Tyr Lys Cys Lys Val Ser Asn Lys Ala Leu Pro
                85                  90                  95

Ala Pro Ile Glu Lys Thr Ile Ser Lys Ala Lys Gly Gln
            100                 105

<210> SEQ ID NO 60
<211> LENGTH: 105
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (26)..(45)
<220> FEATURE:
<221> NAME/KEY: VARIANT
<222> LOCATION: (56)..(65)
<220> FEATURE:
<221> NAME/KEY: VARIANT
<222> LOCATION: (86)..(103)

<400> SEQUENCE: 60

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Gly Phe Ser
            20                  25                  30

Leu Ser Thr Tyr Gly Met Gly Phe Asn Trp Tyr Val Asp Gly Val Glu
        35                  40                  45

Val His Asn Ala Lys Thr Lys Pro Arg Glu Glu Gln Tyr Asn Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Val Gln Glu Gly Tyr Ile Tyr Glu
                85                  90                  95

Lys Thr Ile Ser Lys Ala Lys Gly Gln
            100                 105

<210> SEQ ID NO 61
<211> LENGTH: 106
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (26)..(45)
<220> FEATURE:
<221> NAME/KEY: VARIANT
<222> LOCATION: (56)..(65)
<220> FEATURE:

<221> NAME/KEY: VARIANT
<222> LOCATION: (86)..(104)

<400> SEQUENCE: 61

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Lys Ser Val
            20                  25                  30

Ser Thr Ser Gly Tyr Ser Tyr Phe Asn Trp Tyr Val Asp Gly Val Glu
        35                  40                  45

Val His Asn Ala Lys Thr Lys Pro Arg Glu Glu Gln Tyr Asn Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Gln His Ser Arg Glu Leu Leu Thr
                85                  90                  95

Glu Lys Thr Ile Ser Lys Ala Lys Gly Gln
            100                 105

<210> SEQ ID NO 62
<211> LENGTH: 107
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (26)..(45)
<220> FEATURE:
<221> NAME/KEY: VARIANT
<222> LOCATION: (56)..(65)
<220> FEATURE:
<221> NAME/KEY: VARIANT
<222> LOCATION: (86)..(105)

<400> SEQUENCE: 62

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Gly Phe Ser
            20                  25                  30

Leu Ser Thr Ser Gly Met Gly Phe Asn Trp Tyr Val Asp Gly Val Glu
        35                  40                  45

Val His Asn Ala Lys Thr Lys Pro Arg Glu Glu Gln Tyr Asn Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Thr Leu Tyr Tyr Gly Ser Val Asp
                85                  90                  95

Tyr Glu Lys Thr Ile Ser Lys Ala Lys Gly Gln
            100                 105

<210> SEQ ID NO 63
<211> LENGTH: 107
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (26)..(45)
<220> FEATURE:
<221> NAME/KEY: VARIANT
<222> LOCATION: (56)..(65)

```
<220> FEATURE:
<221> NAME/KEY: VARIANT
<222> LOCATION: (86)..(105)

<400> SEQUENCE: 63

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Gln Ser Val
            20                  25                  30

Asp Tyr Asn Gly Asp Ser Tyr Phe Asn Trp Tyr Val Asp Gly Val Glu
        35                  40                  45

Val His Asn Ala Lys Thr Lys Pro Arg Glu Glu Gln Tyr Asn Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Gln Gln Ser Asn Glu Asp Pro Phe
                85                  90                  95

Thr Glu Lys Thr Ile Ser Lys Ala Lys Gly Gln
            100                 105

<210> SEQ ID NO 64
<211> LENGTH: 108
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (26)..(45)
<220> FEATURE:
<221> NAME/KEY: VARIANT
<222> LOCATION: (56)..(65)
<220> FEATURE:
<221> NAME/KEY: VARIANT
<222> LOCATION: (86)..(106)

<400> SEQUENCE: 64

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Gly Gly Ser
            20                  25                  30

Ile Arg Ser Gly Gly Tyr Tyr Phe Asn Trp Tyr Val Asp Gly Val Glu
        35                  40                  45

Val His Asn Ala Lys Thr Lys Pro Arg Glu Glu Gln Tyr Asn Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Ala Arg Leu Asp Gly Tyr Thr Leu
                85                  90                  95

Asp Ile Glu Lys Thr Ile Ser Lys Ala Lys Gly Gln
            100                 105

<210> SEQ ID NO 65
<211> LENGTH: 108
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (26)..(45)
<220> FEATURE:
<221> NAME/KEY: VARIANT
```

```
<222> LOCATION: (56)..(65)
<220> FEATURE:
<221> NAME/KEY: VARIANT
<222> LOCATION: (86)..(106)

<400> SEQUENCE: 65

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Lys Ser Val
                20                  25                  30

Ser Thr Ser Gly Tyr Asn Tyr Phe Asn Trp Tyr Val Asp Gly Val Glu
            35                  40                  45

Val His Asn Ala Lys Thr Lys Pro Arg Glu Glu Gln Tyr Asn Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Leu Tyr Ser Arg Glu Phe Pro Pro
                85                  90                  95

Trp Thr Glu Lys Thr Ile Ser Lys Ala Lys Gly Gln
                100                 105

<210> SEQ ID NO 66
<211> LENGTH: 105
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (26)..(44)
<220> FEATURE:
<221> NAME/KEY: VARIANT
<222> LOCATION: (55)..(64)
<220> FEATURE:
<221> NAME/KEY: VARIANT
<222> LOCATION: (85)..(103)

<400> SEQUENCE: 66

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Gly Tyr Ser
                20                  25                  30

Ile Thr Ser Asp Tyr Ala Phe Asn Trp Tyr Val Asp Gly Val Glu Val
            35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ala Arg Gly Trp Pro Leu Ala Tyr Glu
                85                  90                  95

Lys Thr Ile Ser Lys Ala Lys Gly Gln
                100                 105

<210> SEQ ID NO 67
<211> LENGTH: 106
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (26)..(44)
<220> FEATURE:
```

-continued

```
<221> NAME/KEY: VARIANT
<222> LOCATION: (55)..(64)
<220> FEATURE:
<221> NAME/KEY: VARIANT
<222> LOCATION: (85)..(104)

<400> SEQUENCE: 67

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Ser Arg Asp
            20                  25                  30

Val Gly Gly Tyr Asn Tyr Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Trp Ser Phe Ala Gly Ser Tyr Tyr Val
                85                  90                  95

Glu Lys Thr Ile Ser Lys Ala Lys Gly Gln
            100                 105

<210> SEQ ID NO 68
<211> LENGTH: 106
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (26)..(44)
<220> FEATURE:
<221> NAME/KEY: VARIANT
<222> LOCATION: (55)..(64)
<220> FEATURE:
<221> NAME/KEY: VARIANT
<222> LOCATION: (85)..(104)

<400> SEQUENCE: 68

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Gly Tyr Ser
            20                  25                  30

Ile Thr Ser Asp Phe Ala Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ala Thr Ala Gly Arg Gly Phe Pro Tyr
                85                  90                  95

Glu Lys Thr Ile Ser Lys Ala Lys Gly Gln
            100                 105

<210> SEQ ID NO 69
<211> LENGTH: 108
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (26)..(44)
```

```
<220> FEATURE:
<221> NAME/KEY: VARIANT
<222> LOCATION: (55)..(64)
<220> FEATURE:
<221> NAME/KEY: VARIANT
<222> LOCATION: (85)..(107)

<400> SEQUENCE: 69

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Ser Ser Asn
            20                  25                  30

Ile Gly Ala Gly Tyr Asp Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Gln Ser Tyr Asp Ser Ser Leu Ser Gly
                85                  90                  95

Ser Val Glu Lys Thr Ile Ser Lys Ala Lys Gly Gln
            100                 105

<210> SEQ ID NO 70
<211> LENGTH: 108
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (26)..(44)
<220> FEATURE:
<221> NAME/KEY: VARIANT
<222> LOCATION: (55)..(64)
<220> FEATURE:
<221> NAME/KEY: VARIANT
<222> LOCATION: (85)..(107)

<400> SEQUENCE: 70

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Gly Tyr Ser
            20                  25                  30

Ile Thr Ser Asp Tyr Ala Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ala Ser Tyr Asp Asp Tyr Thr Trp Phe
                85                  90                  95

Thr Tyr Glu Lys Thr Ile Ser Lys Ala Lys Gly Gln
            100                 105

<210> SEQ ID NO 71
<211> LENGTH: 109
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
```

```
<222> LOCATION: (26)..(44)
<220> FEATURE:
<221> NAME/KEY: VARIANT
<222> LOCATION: (55)..(64)
<220> FEATURE:
<221> NAME/KEY: VARIANT
<222> LOCATION: (85)..(108)

<400> SEQUENCE: 71
```

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Gly Tyr Ser
            20                  25                  30

Ile Ser Asp Tyr Ala Phe Asn Trp Tyr Val Asp Gly Val Glu Val
        35                  40                  45

His Asn Ala Lys Thr Lys Pro Arg Glu Glu Gln Tyr Asn Ser Thr Tyr
 50                  55                  60

Arg Val Val Ser Val Leu Thr Val Leu His Gln Asp Trp Leu Asn Gly
65                  70                  75                  80

Lys Glu Tyr Lys Cys Lys Val Ala Arg Gly Tyr Tyr Gly Ser His
                85                  90                  95

Ser Pro Val Glu Lys Thr Ile Ser Lys Ala Lys Gly Gln
            100                 105

```
<210> SEQ ID NO 72
<211> LENGTH: 110
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (26)..(45)
<220> FEATURE:
<221> NAME/KEY: VARIANT
<222> LOCATION: (56)..(65)
<220> FEATURE:
<221> NAME/KEY: VARIANT
<222> LOCATION: (86)..(109)

<400> SEQUENCE: 72
```

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Gly Phe Ser
            20                  25                  30

Leu Ser Thr Ser Gly Met Ser Phe Asn Trp Tyr Val Asp Gly Val Glu
        35                  40                  45

Val His Asn Ala Lys Thr Lys Pro Arg Glu Glu Gln Tyr Asn Ser Thr
 50                  55                  60

Tyr Arg Val Val Ser Val Leu Thr Val Leu His Gln Asp Trp Leu Asn
65                  70                  75                  80

Gly Lys Glu Tyr Lys Cys Lys Val Ala Arg Arg Thr Thr Thr Ala Asp
                85                  90                  95

Tyr Phe Ala Tyr Glu Lys Thr Ile Ser Lys Ala Lys Gly Gln
            100                 105                 110

```
<210> SEQ ID NO 73
<211> LENGTH: 111
<212> TYPE: PRT
<213> ORGANISM: Artificial Sequence
<220> FEATURE:
<223> OTHER INFORMATION: Example of CH2 domain template molecule
<220> FEATURE:
```

```
<221> NAME/KEY: VARIANT
<222> LOCATION: (26)..(45)
<220> FEATURE:
<221> NAME/KEY: VARIANT
<222> LOCATION: (56)..(65)
<220> FEATURE:
<221> NAME/KEY: VARIANT
<222> LOCATION: (86)..(110)

<400> SEQUENCE: 73
```

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Gly Phe Ser
            20                  25                  30

Leu Ser Thr Tyr Gly Val Gly Phe Asn Trp Tyr Val Asp Gly Val Glu
                35                  40                  45

Val His Asn Ala Lys Thr Lys Pro Arg Glu Glu Gln Tyr Asn Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Ala Arg Leu Gly Ser Asp Tyr Asp
                85                  90                  95

Val Trp Phe Asp Tyr Glu Lys Thr Ile Ser Lys Ala Lys Gly Gln
            100                 105                 110

```
<210> SEQ ID NO 74
<211> LENGTH: 112
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (26)..(45)
<220> FEATURE:
<221> NAME/KEY: VARIANT
<222> LOCATION: (56)..(65)
<220> FEATURE:
<221> NAME/KEY: VARIANT
<222> LOCATION: (86)..(111)

<400> SEQUENCE: 74
```

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Gly Phe Ser
            20                  25                  30

Leu Thr Thr Tyr Gly Met Gly Phe Asn Trp Tyr Val Asp Gly Val Glu
                35                  40                  45

Val His Asn Ala Lys Thr Lys Pro Arg Glu Glu Gln Tyr Asn Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Ala Arg Arg Ala Pro Phe Tyr Gly
                85                  90                  95

Asn His Ala Met Asp Tyr Glu Lys Thr Ile Ser Lys Ala Lys Gly Gln
            100                 105                 110

```
<210> SEQ ID NO 75
<211> LENGTH: 113
<212> TYPE: PRT
<213> ORGANISM: Artificial Sequence
<220> FEATURE:
<223> OTHER INFORMATION: Example of CH2 domain template molecule
```

```
<220> FEATURE:
<221> NAME/KEY: VARIANT
<222> LOCATION: (26)..(45)
<220> FEATURE:
<221> NAME/KEY: VARIANT
<222> LOCATION: (56)..(65)
<220> FEATURE:
<221> NAME/KEY: VARIANT
<222> LOCATION: (86)..(112)

<400> SEQUENCE: 75

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Gly Phe Ser
            20                  25                  30

Leu Ser Thr Ser Gly Met Gly Phe Asn Trp Tyr Val Asp Gly Val Glu
        35                  40                  45

Val His Asn Ala Lys Thr Lys Pro Arg Glu Glu Gln Tyr Asn Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Val Arg Arg Ala His Thr Thr Val
                85                  90                  95

Leu Gly Asp Trp Phe Ala Tyr Glu Lys Thr Ile Ser Lys Ala Lys Gly
            100                 105                 110

Gln

<210> SEQ ID NO 76
<211> LENGTH: 114
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (26)..(45)
<220> FEATURE:
<221> NAME/KEY: VARIANT
<222> LOCATION: (56)..(65)
<220> FEATURE:
<221> NAME/KEY: VARIANT
<222> LOCATION: (86)..(113)

<400> SEQUENCE: 76

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Gly Phe Ser
            20                  25                  30

Leu Ser Thr Ser Gly Met Ser Phe Asn Trp Tyr Val Asp Gly Val Glu
        35                  40                  45

Val His Asn Ala Lys Thr Lys Pro Arg Glu Glu Gln Tyr Asn Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Ala Arg Thr Leu Arg Val Ser Gly
                85                  90                  95

Asp Tyr Val Arg Asp Phe Asp Leu Glu Lys Thr Ile Ser Lys Ala Lys
            100                 105                 110

Gly Gln

<210> SEQ ID NO 77
```

```
<211> LENGTH: 115
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (26)..(45)
<220> FEATURE:
<221> NAME/KEY: VARIANT
<222> LOCATION: (56)..(65)
<220> FEATURE:
<221> NAME/KEY: VARIANT
<222> LOCATION: (86)..(114)

<400> SEQUENCE: 77

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Gly Phe Ser
            20                  25                  30

Ile Arg Thr Ser Lys Val Gly Phe Asn Trp Tyr Val Asp Gly Val Glu
        35                  40                  45

Val His Asn Ala Lys Thr Lys Pro Arg Glu Glu Gln Tyr Asn Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Ala Arg Arg Gly Phe Tyr Gly Arg
                85                  90                  95

Lys Tyr Glu Val Asn His Phe Asp Tyr Glu Lys Thr Ile Ser Lys Ala
            100                 105                 110

Lys Gly Gln
        115

<210> SEQ ID NO 78
<211> LENGTH: 116
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (26)..(45)
<220> FEATURE:
<221> NAME/KEY: VARIANT
<222> LOCATION: (56)..(114)

<400> SEQUENCE: 78

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Gly Phe Ser
            20                  25                  30

Leu Ser Thr Ser Gly Met Gly Phe Asn Trp Tyr Val Asp Gly Val Glu
        35                  40                  45

Val His Asn Ala Lys Thr Lys Pro Arg Glu Glu Gln Tyr Asn Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Ala Arg Arg Thr Phe Ser Tyr Tyr
                85                  90                  95

Tyr Gly Ser Ser Phe Tyr Tyr Phe Asp Asn Glu Lys Thr Ile Ser Lys
            100                 105                 110

Ala Lys Gly Gln
```

```
<210> SEQ ID NO 79
<211> LENGTH: 122
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (26)..(45)
<220> FEATURE:
<221> NAME/KEY: VARIANT
<222> LOCATION: (56)..(65)
<220> FEATURE:
<221> NAME/KEY: VARIANT
<222> LOCATION: (86)..(120)

<400> SEQUENCE: 79

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Gly Phe Ser
            20                  25                  30

Leu Ser Asp Phe Gly Val Gly Phe Asn Trp Tyr Val Asp Gly Val Glu
        35                  40                  45

Val His Asn Ala Lys Thr Lys Pro Arg Glu Glu Gln Tyr Asn Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Ala His Arg Arg Gly Pro Thr Thr
                85                  90                  95

Leu Phe Gly Val Pro Ile Ala Arg Gly Pro Val Asn Ala Met Asp Val
            100                 105                 110

Glu Lys Thr Ile Ser Lys Ala Lys Gly Gln
            115                 120

<210> SEQ ID NO 80
<211> LENGTH: 110
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (26)..(47)
<220> FEATURE:
<221> NAME/KEY: VARIANT
<222> LOCATION: (58)..(67)
<220> FEATURE:
<221> NAME/KEY: VARIANT
<222> LOCATION: (88)..(108)

<400> SEQUENCE: 80

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Ala Arg Arg
            20                  25                  30

Thr Thr Thr Ala Asp Tyr Phe Ala Tyr Phe Asn Trp Tyr Val Asp Gly
        35                  40                  45

Val Glu Val His Asn Ala Lys Thr Lys Pro Arg Glu Glu Gln Tyr Asn
    50                  55                  60

Ser Thr Tyr Arg Val Val Ser Val Leu Thr Val Leu His Gln Asp Trp
65                  70                  75                  80
```

```
Leu Asn Gly Lys Glu Tyr Lys Cys Lys Val Gly Phe Ser Leu Ser Thr
                85                  90                  95

Ser Gly Met Ser Glu Lys Thr Ile Ser Lys Ala Lys Gly Gln
            100                 105                 110

<210> SEQ ID NO 81
<211> LENGTH: 111
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (26)..(48)
<220> FEATURE:
<221> NAME/KEY: VARIANT
<222> LOCATION: (59)..(68)
<220> FEATURE:
<221> NAME/KEY: VARIANT
<222> LOCATION: (89)..(109)

<400> SEQUENCE: 81

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Ala Arg Leu
            20                  25                  30

Gly Ser Asp Tyr Asp Val Trp Phe Asp Tyr Phe Asn Trp Tyr Val Asp
        35                  40                  45

Gly Val Glu Val His Asn Ala Lys Thr Lys Pro Arg Glu Glu Gln Tyr
    50                  55                  60

Asn Ser Thr Tyr Arg Val Val Ser Val Leu Thr Val Leu His Gln Asp
65                  70                  75                  80

Trp Leu Asn Gly Lys Glu Tyr Lys Cys Lys Val Gly Phe Ser Leu Ser
                85                  90                  95

Thr Tyr Gly Val Gly Glu Lys Thr Ile Ser Lys Ala Lys Gly Gln
            100                 105                 110

<210> SEQ ID NO 82
<211> LENGTH: 112
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (26)..(49)
<220> FEATURE:
<221> NAME/KEY: VARIANT
<222> LOCATION: (60)..(69)
<220> FEATURE:
<221> NAME/KEY: VARIANT
<222> LOCATION: (90)..(110)

<400> SEQUENCE: 82

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Ala Arg Arg
            20                  25                  30

Ala Pro Phe Tyr Gly Asn His Ala Met Asp Tyr Phe Asn Trp Tyr Val
        35                  40                  45

Asp Gly Val Glu Val His Asn Ala Lys Thr Lys Pro Arg Glu Glu Gln
    50                  55                  60

Tyr Asn Ser Thr Tyr Arg Val Val Ser Val Leu Thr Val Leu His Gln
65                  70                  75                  80
```

```
Asp Trp Leu Asn Gly Lys Glu Tyr Lys Cys Lys Val Gly Phe Ser Leu
            85                  90                  95

Thr Thr Tyr Gly Met Gly Glu Lys Thr Ile Ser Lys Ala Lys Gly Gln
            100                 105                 110

<210> SEQ ID NO 83
<211> LENGTH: 113
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (26)..(50)
<220> FEATURE:
<221> NAME/KEY: VARIANT
<222> LOCATION: (61)..(70)
<220> FEATURE:
<221> NAME/KEY: VARIANT
<222> LOCATION: (91)..(111)

<400> SEQUENCE: 83

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Arg Arg
            20                  25                  30

Ala His Thr Thr Val Leu Gly Asp Trp Phe Ala Tyr Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65              70                  75                  80

Gln Asp Trp Leu Asn Gly Lys Glu Tyr Lys Cys Lys Val Gly Phe Ser
            85                  90                  95

Leu Ser Thr Ser Gly Met Gly Glu Lys Thr Ile Ser Lys Ala Lys Gly
            100                 105                 110

Gln

<210> SEQ ID NO 84
<211> LENGTH: 114
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (26)..(51)
<220> FEATURE:
<221> NAME/KEY: VARIANT
<222> LOCATION: (62)..(71)
<220> FEATURE:
<221> NAME/KEY: VARIANT
<222> LOCATION: (92)..(112)

<400> SEQUENCE: 84

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Ala Arg Thr
            20                  25                  30

Leu Arg Val Ser Gly Asp Tyr Val Arg Asp Phe Asp Leu Phe Asn Trp
            35                  40                  45

Tyr Val Asp Gly Val Glu Val His Asn Ala Lys Thr Lys Pro Arg Glu
        50                  55                  60
```

```
Glu Gln Tyr Asn Ser Thr Tyr Arg Val Val Ser Val Leu Thr Val Leu
 65                  70                  75                  80

His Gln Asp Trp Leu Asn Gly Lys Glu Tyr Lys Cys Lys Val Gly Phe
                 85                  90                  95

Ser Leu Ser Thr Ser Gly Met Ser Glu Lys Thr Ile Ser Lys Ala Lys
            100                 105                 110

Gly Gln

<210> SEQ ID NO 85
<211> LENGTH: 115
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (26)..(52)
<220> FEATURE:
<221> NAME/KEY: VARIANT
<222> LOCATION: (63)..(72)
<220> FEATURE:
<221> NAME/KEY: VARIANT
<222> LOCATION: (93)..(113)

<400> SEQUENCE: 85

Gly Gly Pro Ser Val Phe Leu Phe Pro Pro Lys Pro Lys Asp Thr Leu
 1               5                  10                  15

Met Ile Ser Arg Thr Pro Glu Val Thr Cys Val Val Val Ala Arg Arg
             20                  25                  30

Gly Phe Tyr Gly Arg Lys Tyr Glu Val Asn His Phe Asp Tyr Phe Asn
             35                  40                  45

Trp Tyr Val Asp Gly Val Glu Val His Asn Ala Lys Thr Lys Pro Arg
 50                  55                  60

Glu Glu Gln Tyr Asn Ser Thr Tyr Arg Val Val Ser Val Leu Thr Val
 65                  70                  75                  80

Leu His Gln Asp Trp Leu Asn Gly Lys Glu Tyr Lys Cys Lys Val Gly
                 85                  90                  95

Phe Ser Ile Arg Thr Ser Lys Val Gly Glu Lys Thr Ile Ser Lys Ala
            100                 105                 110

Lys Gly Gln
        115

<210> SEQ ID NO 86
<211> LENGTH: 116
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (26)..(53)
<220> FEATURE:
<221> NAME/KEY: VARIANT
<222> LOCATION: (64)..(73)
<220> FEATURE:
<221> NAME/KEY: VARIANT
<222> LOCATION: (94)..(114)

<400> SEQUENCE: 86

Gly Gly Pro Ser Val Phe Leu Phe Pro Pro Lys Pro Lys Asp Thr Leu
 1               5                  10                  15

Met Ile Ser Arg Thr Pro Glu Val Thr Cys Val Val Val Ala Arg Arg
             20                  25                  30
```

```
Thr Phe Ser Tyr Tyr Tyr Gly Ser Phe Tyr Tyr Phe Asp Asn Phe
        35                  40                  45

Asn Trp Tyr Val Asp Gly Val Glu Val His Asn Ala Lys Thr Lys Pro
 50                  55                  60

Arg Glu Glu Gln Tyr Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                85                  90                  95

Gly Phe Ser Leu Ser Thr Ser Gly Met Gly Glu Lys Thr Ile Ser Lys
               100                 105                 110

Ala Lys Gly Gln
       115
```

```
<210> SEQ ID NO 87
<211> LENGTH: 122
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (26)..(59)
<220> FEATURE:
<221> NAME/KEY: VARIANT
<222> LOCATION: (70)..(79)
<220> FEATURE:
<221> NAME/KEY: VARIANT
<222> LOCATION: (100)..(120)

<400> SEQUENCE: 87
```

```
Gly Gly Pro Ser Val Phe Leu Phe Pro Pro Lys Pro Lys Asp Thr Leu
 1               5                  10                  15

Met Ile Ser Arg Thr Pro Glu Val Thr Cys Val Val Val Ala His Arg
                20                  25                  30

Arg Gly Pro Thr Thr Leu Phe Gly Val Pro Ile Ala Arg Gly Pro Val
                35                  40                  45

Asn Ala Met Asp Val Phe Asn Trp Tyr Val Asp Gly Val Glu Val His
 50                  55                  60

Asn Ala Lys Thr Lys Pro Arg Glu Glu Gln Tyr Asn Ser Thr Tyr Arg
 65                  70                  75                  80

Val Val Ser Val Leu Thr Val Leu His Gln Asp Trp Leu Asn Gly Lys
                85                  90                  95

Glu Tyr Lys Cys Lys Val Gly Phe Ser Leu Ser Asp Phe Gly Val Gly
               100                 105                 110

Glu Lys Thr Ile Ser Lys Ala Lys Gly Gln
       115                 120
```

```
<210> SEQ ID NO 88
<211> LENGTH: 107
<212> TYPE: PRT
<213> ORGANISM: Artificial Sequence
<220> FEATURE:
<223> OTHER INFORMATION: Example of CH2 domain template molecule
<220> FEATURE:
<221> NAME/KEY: VARIANT
<222> LOCATION: (26)..(44)
<220> FEATURE:
<221> NAME/KEY: VARIANT
<222> LOCATION: (55)..(64)
<220> FEATURE:
<221> NAME/KEY: VARIANT
<222> LOCATION: (85)..(105)
```

<400> SEQUENCE: 88

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Ser Asn Lys
            20                  25                  30

Ala Leu Pro Ala Pro Ile Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Asp Val Ser His Glu Asp Pro Glu Val
                85                  90                  95

Lys Glu Lys Thr Ile Ser Lys Ala Lys Gly Gln
            100                 105

<210> SEQ ID NO 89
<211> LENGTH: 116
<212> TYPE: PRT
<213> ORGANISM: Artificial Sequence
<220> FEATURE:
<223> OTHER INFORMATION: CH2D Wild type Monomer
<220> FEATURE:
<221> NAME/KEY: BINDING
<222> LOCATION: (1)..(6)

<400> SEQUENCE: 89

His His His His His His Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
                100                 105                 110

Ser Lys Ala Lys
        115

<210> SEQ ID NO 90
<211> LENGTH: 126
<212> TYPE: PRT
<213> ORGANISM: Artificial Sequence
<220> FEATURE:
<223> OTHER INFORMATION: CH2 domain wild type dimer
<220> FEATURE:
<221> NAME/KEY: BINDING
<222> LOCATION: (1)..(6)
<220> FEATURE:
<221> NAME/KEY: VARIANT
<222> LOCATION: (7)..(16)

<400> SEQUENCE: 90

His His His His His His Gly Ser Gly Ser Cys Asp Lys Thr His Thr
1               5                   10                  15

```
Ala Pro Glu Leu Leu Gly Gly Pro Ser Val Phe Leu Phe Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys
            115                 120                 125

<210> SEQ ID NO 91
<211> LENGTH: 108
<212> TYPE: PRT
<213> ORGANISM: Artificial Sequence
<220> FEATURE:
<223> OTHER INFORMATION: CH2 domain stabilized monomer
<220> FEATURE:
<221> NAME/KEY: BINDING
<222> LOCATION: (1)..(6)
<220> FEATURE:
<221> NAME/KEY: DISULFID
<222> LOCATION: (11)..(102)

<400> SEQUENCE: 91

His His His His His Pro Ser Val Phe Cys Phe Pro Pro Lys Pro Lys
1               5                   10                  15

Asp Thr Leu Met Ile Ser Arg Thr Pro Glu Val Thr Cys Val Val Val
            20                  25                  30

Asp Val Ser His Glu Asp Pro Glu Val Lys Phe Asn Trp Tyr Val Asp
        35                  40                  45

Gly Val Glu Val His Asn Ala Lys Thr Lys Pro Arg Glu Glu Gln Tyr
    50                  55                  60

Asn Ser Thr Tyr Arg Val Val Ser Val Leu Thr Val Leu His Gln Asp
65                  70                  75                  80

Trp Leu Asn Gly Lys Glu Tyr Lys Cys Lys Val Ser Asn Lys Ala Leu
                85                  90                  95

Pro Ala Pro Ile Glu Cys Thr Ile Ser Lys Ala Lys
            100                 105

<210> SEQ ID NO 92
<211> LENGTH: 145
<212> TYPE: PRT
<213> ORGANISM: Artificial Sequence
<220> FEATURE:
<223> OTHER INFORMATION: Example of CH2 molecule (parent molecule)
<220> FEATURE:
<221> NAME/KEY: BINDING
<222> LOCATION: (1)..(23)
<220> FEATURE:
<221> NAME/KEY: Binding
<222> LOCATION: (24)..(33)

<400> SEQUENCE: 92

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
            20                  25                  30
```

```
His Ala Pro Glu Leu Leu Gly Gly Pro Ser Val Phe Leu Phe Pro Pro
        35                  40                  45

Lys Pro Lys Asp Thr Leu Met Ile Ser Arg Thr Pro Glu Val Thr Cys
 50                  55                  60

Val Val Val Asp Val Ser His Glu Asp Pro Glu Val Lys Phe Asn Trp
 65                  70                  75                  80

Tyr Val Asp Gly Val Glu Val His Asn Ala Lys Thr Lys Pro Arg Glu
                 85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Cys Lys Val Ser Asn
            115                 120                 125

Lys Ala Leu Pro Ala Pro Ile Glu Lys Thr Ile Ser Lys Ala Lys Gly
        130                 135                 140

Gln
145

<210> SEQ ID NO 93
<211> LENGTH: 143
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: BINDING
<222> LOCATION: (24)..(33)
<220> FEATURE:
<221> NAME/KEY: Variant
<222> LOCATION: (94)..(101)

<400> SEQUENCE: 93

Met Lys Lys Ile Trp Leu Ala Leu Ala Gly Leu Val Leu Ala Phe Ser
 1               5                  10                  15

Ala Ser Ala Ala Gly Tyr Glu Asp Gly Lys Gly His His His His His
             20                  25                  30

His Ala Pro Glu Leu Leu Gly Gly Pro Ser Val Phe Leu Phe Pro Pro
        35                  40                  45

Lys Pro Lys Asp Thr Leu Met Ile Ser Arg Thr Pro Glu Val Thr Cys
 50                  55                  60

Val Val Val Asp Val Ser His Glu Asp Pro Glu Val Lys Phe Asn Trp
 65                  70                  75                  80

Tyr Val Asp Gly Val Glu Val His Asn Ala Lys Thr Lys Pro Arg Glu
                 85                  90                  95

Glu His Asn Thr Tyr Arg Val Val Ser Val Leu Thr Val Leu His Gln
            100                 105                 110

Asp Trp Leu Asn Gly Lys Glu Tyr Lys Cys Lys Val Ser Asn Lys Ala
        115                 120                 125

Leu Pro Ala Pro Ile Glu Lys Thr Ile Ser Lys Ala Lys Gly Gln
        130                 135                 140

<210> SEQ ID NO 94
<211> LENGTH: 144
<212> TYPE: PRT
<213> ORGANISM: Artificial Sequence
<220> FEATURE:
<223> OTHER INFORMATION: Example of variant CH2 molecule
<220> FEATURE:
```

```
<221> NAME/KEY: BINDING
<222> LOCATION: (1)..(23)
<220> FEATURE:
<221> NAME/KEY: BINDING
<222> LOCATION: (24)..(33)
<220> FEATURE:
<221> NAME/KEY: Variant
<222> LOCATION: (94)..(102)

<400> SEQUENCE: 94

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His His
            20                  25                  30

His Ala Pro Glu Leu Leu Gly Gly Pro Ser Val Phe Leu Phe Pro Pro
        35                  40                  45

Lys Pro Lys Asp Thr Leu Met Ile Ser Arg Thr Pro Glu Val Thr Cys
50                  55                  60

Val Val Val Asp Val Ser His Glu Asp Pro Glu Val Lys Phe Asn Trp
65                  70                  75                  80

Tyr Val Asp Gly Val Glu Val His Asn Ala Lys Thr Lys Pro Arg Glu
                85                  90                  95

Glu Ala Ala Ser Thr Tyr Arg Val Val Ser Val Leu Thr Val Leu His
                100                 105                 110

Gln Asp Trp Leu Asn Gly Lys Glu Tyr Lys Cys Lys Val Ser Asn Lys
            115                 120                 125

Ala Leu Pro Ala Pro Ile Glu Lys Thr Ile Ser Lys Ala Lys Gly Gln
        130                 135                 140

<210> SEQ ID NO 95
<211> LENGTH: 145
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (94)..(103)

<400> SEQUENCE: 95

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His His
            20                  25                  30

His Ala Pro Glu Leu Leu Gly Gly Pro Ser Val Phe Leu Phe Pro Pro
        35                  40                  45

Lys Pro Lys Asp Thr Leu Met Ile Ser Arg Thr Pro Glu Val Thr Cys
50                  55                  60

Val Val Val Asp Val Ser His Glu Asp Pro Glu Val Lys Phe Asn Trp
65                  70                  75                  80

Tyr Val Asp Gly Val Glu Val His Asn Ala Lys Thr Lys Pro Arg Glu
                85                  90                  95

Glu Tyr Asp Thr Ser Thr Tyr Arg Val Val Ser Val Leu Thr Val Leu
                100                 105                 110

His Gln Asp Trp Leu Asn Gly Lys Glu Tyr Lys Cys Lys Val Ser Asn
```

-continued

```
                115                 120                 125
Lys Ala Leu Pro Ala Pro Ile Glu Lys Thr Ile Ser Lys Ala Lys Gly
    130                 135                 140

Gln
145

<210> SEQ ID NO 96
<211> LENGTH: 145
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (94)..(103)

<400> SEQUENCE: 96

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
            20                  25                  30

His Ala Pro Glu Leu Leu Gly Gly Pro Ser Val Phe Leu Phe Pro Pro
        35                  40                  45

Lys Pro Lys Asp Thr Leu Met Ile Ser Arg Thr Pro Glu Val Thr Cys
50                  55                  60

Val Val Val Asp Val Ser His Glu Asp Pro Glu Val Lys Phe Asn Trp
65                  70                  75                  80

Tyr Val Asp Gly Val Glu Val His Asn Ala Lys Thr Lys Pro Arg Val
                85                  90                  95

Tyr Pro Gly Ser Ile Thr Tyr Arg Val Val Ser Val Leu Thr Val Leu
            100                 105                 110

His Gln Asp Trp Leu Asn Gly Lys Glu Tyr Lys Cys Lys Val Ser Asn
        115                 120                 125

Lys Ala Leu Pro Ala Pro Ile Glu Lys Thr Ile Ser Lys Ala Lys Gly
    130                 135                 140

Gln
145

<210> SEQ ID NO 97
<211> LENGTH: 146
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (94)..(104)

<400> SEQUENCE: 97

Met Lys Lys Ile Trp Leu Ala Leu Ala Gly Leu Val Leu Ala Phe Ser
1               5                   10                  15
```

```
Ala Ser Ala Ala Gly Tyr Glu Asp Gly Lys Gly His His His His
            20                  25                  30

His Ala Pro Glu Leu Leu Gly Gly Pro Ser Val Phe Leu Phe Pro Pro
        35                  40                  45

Lys Pro Lys Asp Thr Leu Met Ile Ser Arg Thr Pro Glu Val Thr Cys
 50                  55                  60

Val Val Val Asp Val Ser His Glu Asp Pro Glu Val Lys Phe Asn Trp
 65                  70                  75                  80

Tyr Val Asp Gly Val Glu Val His Asn Ala Lys Thr Lys Pro Arg Ile
                 85                  90                  95

Tyr Trp Asp Asp Asp Lys Thr Tyr Arg Val Val Ser Val Leu Thr Val
                100                 105                 110

Leu His Gln Asp Trp Leu Asn Gly Lys Glu Tyr Lys Cys Lys Val Ser
                115                 120                 125

Asn Lys Ala Leu Pro Ala Pro Ile Glu Lys Thr Ile Ser Lys Ala Lys
                130                 135                 140

Gly Gln
145
```

<210> SEQ ID NO 98
<211> LENGTH: 147
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (94)..(105)

<400> SEQUENCE: 98

```
Met Lys Lys Ile Trp Leu Ala Leu Ala Gly Leu Val Leu Ala Phe Ser
 1               5                  10                  15

Ala Ser Ala Ala Gly Tyr Glu Asp Gly Lys Gly His His His His
            20                  25                  30

His Ala Pro Glu Leu Leu Gly Gly Pro Ser Val Phe Leu Phe Pro Pro
        35                  40                  45

Lys Pro Lys Asp Thr Leu Met Ile Ser Arg Thr Pro Glu Val Thr Cys
 50                  55                  60

Val Val Val Asp Val Ser His Glu Asp Pro Glu Val Lys Phe Asn Trp
 65                  70                  75                  80

Tyr Val Asp Gly Val Glu Val His Asn Ala Lys Thr Lys Pro Arg Ile
                 85                  90                  95

Ser Ser Ser Gly Asp Pro Thr Thr Tyr Arg Val Val Ser Val Leu Thr
                100                 105                 110

Val Leu His Gln Asp Trp Leu Asn Gly Lys Glu Tyr Lys Cys Lys Val
                115                 120                 125

Ser Asn Lys Ala Leu Pro Ala Pro Ile Glu Lys Thr Ile Ser Lys Ala
                130                 135                 140

Lys Gly Gln
145
```

<210> SEQ ID NO 99
<211> LENGTH: 143

-continued

```
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (64)..(83)
<220> FEATURE:
<221> NAME/KEY: Variant
<222> LOCATION: (124)..(133)

<400> SEQUENCE: 99

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
            20                  25                  30

His Ala Pro Glu Leu Leu Gly Gly Pro Ser Val Phe Leu Phe Pro Pro
            35                  40                  45

Lys Pro Lys Asp Thr Leu Met Ile Ser Arg Thr Pro Glu Val Thr Cys
50                  55                  60

Val Val Val Gly Phe Ser Leu Ser Thr Tyr Gly Met Gly Phe Asn Trp
65                  70                  75                  80

Tyr Val Asp Gly Val Glu Val His Asn Ala Lys Thr Lys Pro Arg Glu
                85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Cys Lys Val Val Gln
            115                 120                 125

Glu Gly Tyr Ile Tyr Glu Lys Thr Ile Ser Lys Ala Lys Gly Gln
        130                 135                 140

<210> SEQ ID NO 100
<211> LENGTH: 144
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (64)..(83)
<220> FEATURE:
<221> NAME/KEY: Variant
<222> LOCATION: (124)..(142)

<400> SEQUENCE: 100

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
            20                  25                  30

His Ala Pro Glu Leu Leu Gly Gly Pro Ser Val Phe Leu Phe Pro Pro
            35                  40                  45

Lys Pro Lys Asp Thr Leu Met Ile Ser Arg Thr Pro Glu Val Thr Cys
50                  55                  60
```

```
Val Val Val Lys Ser Val Ser Thr Ser Gly Tyr Ser Tyr Phe Asn Trp
 65                  70                  75                  80

Tyr Val Asp Gly Val Glu Val His Asn Ala Lys Thr Lys Pro Arg Glu
                 85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Cys Lys Val Gln His
            115                 120                 125

Ser Arg Glu Leu Leu Thr Glu Lys Thr Ile Ser Lys Ala Lys Gly Gln
        130                 135                 140

<210> SEQ ID NO 101
<211> LENGTH: 145
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (64)..(83)
<220> FEATURE:
<221> NAME/KEY: Variant
<222> LOCATION: (124)..(143)

<400> SEQUENCE: 101

Met Lys Lys Ile Trp Leu Ala Leu Ala Gly Leu Val Leu Ala Phe Ser
 1               5                  10                  15

Ala Ser Ala Ala Gly Tyr Glu Asp Gly Lys Gly His His His His His
                 20                  25                  30

His Ala Pro Glu Leu Leu Gly Gly Pro Ser Val Phe Leu Phe Pro Pro
            35                  40                  45

Lys Pro Lys Asp Thr Leu Met Ile Ser Arg Thr Pro Glu Val Thr Cys
 50                  55                  60

Val Val Val Gly Phe Ser Leu Ser Thr Ser Gly Met Gly Phe Asn Trp
 65                  70                  75                  80

Tyr Val Asp Gly Val Glu Val His Asn Ala Lys Thr Lys Pro Arg Glu
                 85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Cys Lys Val Thr Leu
            115                 120                 125

Tyr Tyr Gly Ser Val Asp Tyr Glu Lys Thr Ile Ser Lys Ala Lys Gly
        130                 135                 140

Gln
145

<210> SEQ ID NO 102
<211> LENGTH: 145
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
```

```
<221> NAME/KEY: Binding
<222> LOCATION: (24)..(33)
<220> FEATURE:
<221> NAME/KEY: Variant
<222> LOCATION: (64)..(83)
<220> FEATURE:
<221> NAME/KEY: Variant
<222> LOCATION: (124)..(144)

<400> SEQUENCE: 102
```

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
            20                  25                  30

His Ala Pro Glu Leu Leu Gly Gly Pro Ser Val Phe Leu Phe Pro Pro
        35                  40                  45

Lys Pro Lys Asp Thr Leu Met Ile Ser Arg Thr Pro Glu Val Thr Cys
    50                  55                  60

Val Val Val Gln Ser Val Asp Tyr Asn Gly Asp Ser Tyr Phe Asn Trp
65                  70                  75                  80

Tyr Val Asp Gly Val Glu Val His Asn Ala Lys Thr Lys Pro Arg Glu
                85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Cys Lys Val Gln Gln
        115                 120                 125

Ser Asn Glu Asp Pro Phe Thr Glu Lys Thr Ile Ser Lys Ala Lys Gly
    130                 135                 140

Gln
145

```
<210> SEQ ID NO 103
<211> LENGTH: 146
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: VARIANT
<222> LOCATION: (64)..(83)
<220> FEATURE:
<221> NAME/KEY: VARIANT
<222> LOCATION: (124)..(144)

<400> SEQUENCE: 103
```

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
            20                  25                  30

His Ala Pro Glu Leu Leu Gly Gly Pro Ser Val Phe Leu Phe Pro Pro
        35                  40                  45

Lys Pro Lys Asp Thr Leu Met Ile Ser Arg Thr Pro Glu Val Thr Cys
    50                  55                  60

Val Val Val Gly Gly Ser Ile Arg Ser Gly Gly Tyr Tyr Phe Asn Trp
65                  70                  75                  80

Tyr Val Asp Gly Val Glu Val His Asn Ala Lys Thr Lys Pro Arg Glu

```
                85                  90                  95
Glu Gln Tyr Asn Ser Thr Tyr Arg Val Val Ser Val Leu Thr Val Leu
                100                 105                 110

His Gln Asp Trp Leu Asn Gly Lys Glu Tyr Lys Cys Lys Val Ala Arg
                115                 120                 125

Leu Asp Gly Tyr Thr Leu Asp Ile Glu Lys Thr Ile Ser Lys Ala Lys
            130                 135                 140

Gly Gln
145

<210> SEQ ID NO 104
<211> LENGTH: 146
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: VARIANT
<222> LOCATION: (64)..(83)
<220> FEATURE:
<221> NAME/KEY: VARIANT
<222> LOCATION: (124)..(144)

<400> SEQUENCE: 104

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
                20                  25                  30

His Ala Pro Glu Leu Leu Gly Gly Pro Ser Val Phe Leu Phe Pro Pro
            35                  40                  45

Lys Pro Lys Asp Thr Leu Met Ile Ser Arg Thr Pro Glu Val Thr Cys
50                  55                  60

Val Val Val Lys Ser Val Ser Thr Ser Gly Tyr Asn Tyr Phe Asn Trp
65                  70                  75                  80

Tyr Val Asp Gly Val Glu Val His Asn Ala Lys Thr Lys Pro Arg Glu
                85                  90                  95

Glu Gln Tyr Asn Ser Thr Tyr Arg Val Val Ser Val Leu Thr Val Leu
                100                 105                 110

His Gln Asp Trp Leu Asn Gly Lys Glu Tyr Lys Cys Lys Val Leu Tyr
                115                 120                 125

Ser Arg Glu Phe Pro Pro Trp Thr Glu Lys Thr Ile Ser Lys Ala Lys
            130                 135                 140

Gly Gln
145

<210> SEQ ID NO 105
<211> LENGTH: 143
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: binding
<222> LOCATION: (24)..(33)
```

```
-continued

<220> FEATURE:
<221> NAME/KEY: variant
<222> LOCATION: (64)..(94)
<220> FEATURE:
<221> NAME/KEY: variant
<222> LOCATION: (125)..(143)

<400> SEQUENCE: 105

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
            20                  25                  30

His Ala Pro Glu Leu Leu Gly Gly Pro Ser Val Phe Leu Phe Pro Pro
        35                  40                  45

Lys Pro Lys Asp Thr Leu Met Ile Ser Arg Thr Pro Glu Val Thr Cys
50                  55                  60

Val Val Val Gly Tyr Ser Ile Thr Ser Asp Tyr Ala Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ala Arg Gly
        115                 120                 125

Trp Pro Leu Ala Tyr Glu Lys Thr Ile Ser Lys Ala Lys Gly Gln
    130                 135                 140

<210> SEQ ID NO 106
<211> LENGTH: 144
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (64)..(82)
<220> FEATURE:
<221> NAME/KEY: Variant
<222> LOCATION: (123)..(142)

<400> SEQUENCE: 106

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
            20                  25                  30

His Ala Pro Glu Leu Leu Gly Gly Pro Ser Val Phe Leu Phe Pro Pro
        35                  40                  45

Lys Pro Lys Asp Thr Leu Met Ile Ser Arg Thr Pro Glu Val Thr Cys
50                  55                  60

Val Val Val Ser Arg Asp Val Gly Gly Tyr Asn Tyr Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110
```

-continued

Gln Asp Trp Leu Asn Gly Lys Glu Tyr Lys Cys Lys Val Trp Ser Phe
        115                 120                 125

Ala Gly Ser Tyr Tyr Val Glu Lys Thr Ile Ser Lys Ala Lys Gly Gln
    130                 135                 140

<210> SEQ ID NO 107
<211> LENGTH: 144
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (64)..(82)
<220> FEATURE:
<221> NAME/KEY: Variant
<222> LOCATION: (123)..(142)

<400> SEQUENCE: 107

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His His
            20                  25                  30

His Ala Pro Glu Leu Leu Gly Gly Pro Ser Val Phe Leu Phe Pro Pro
        35                  40                  45

Lys Pro Lys Asp Thr Leu Met Ile Ser Arg Thr Pro Glu Val Thr Cys
    50                  55                  60

Val Val Val Gly Tyr Ser Ile Thr Ser Asp Phe Ala Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ala Thr Ala
        115                 120                 125

Gly Arg Gly Phe Pro Tyr Glu Lys Thr Ile Ser Lys Ala Lys Gly Gln
    130                 135                 140

<210> SEQ ID NO 108
<211> LENGTH: 146
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (64)..(82)
<220> FEATURE:
<221> NAME/KEY: Variant
<222> LOCATION: (123)..(142)

<400> SEQUENCE: 108

Met Lys Lys Ile Trp Leu Ala Leu Ala Gly Leu Val Leu Ala Phe Ser
1               5                   10                  15

```
Ala Ser Ala Ala Gly Tyr Glu Asp Gly Lys Gly His His His His
            20                  25                  30
His Ala Pro Glu Leu Leu Gly Gly Pro Ser Val Phe Leu Phe Pro Pro
            35                  40                  45
Lys Pro Lys Asp Thr Leu Met Ile Ser Arg Thr Pro Glu Val Thr Cys
 50                  55                  60
Val Val Val Ser Ser Asn Ile Gly Ala Gly Tyr Asp Phe Asn Trp Tyr
 65                  70                  75                  80
Val Asp Gly Val Glu Val His Asn Ala Lys Thr Lys Pro Arg Glu Glu
                 85                  90                  95
Gln Tyr Asn Ser Thr Tyr Arg Val Val Ser Val Leu Thr Val Leu His
            100                 105                 110
Gln Asp Trp Leu Asn Gly Lys Glu Tyr Lys Cys Lys Val Gln Ser Tyr
            115                 120                 125
Asp Ser Ser Leu Ser Gly Ser Val Glu Lys Thr Ile Ser Lys Ala Lys
            130                 135                 140
Gly Gln
145
```

<210> SEQ ID NO 109
<211> LENGTH: 146
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (64)..(82)
<220> FEATURE:
<221> NAME/KEY: Variant
<222> LOCATION: (123)..(142)

<400> SEQUENCE: 109

```
Met Lys Lys Ile Trp Leu Ala Leu Ala Gly Leu Val Leu Ala Phe Ser
 1               5                  10                  15
Ala Ser Ala Ala Gly Tyr Glu Asp Gly Lys Gly His His His His
            20                  25                  30
His Ala Pro Glu Leu Leu Gly Gly Pro Ser Val Phe Leu Phe Pro Pro
            35                  40                  45
Lys Pro Lys Asp Thr Leu Met Ile Ser Arg Thr Pro Glu Val Thr Cys
 50                  55                  60
Val Val Val Gly Tyr Ser Ile Thr Ser Asp Tyr Ala Phe Asn Trp Tyr
 65                  70                  75                  80
Val Asp Gly Val Glu Val His Asn Ala Lys Thr Lys Pro Arg Glu Glu
                 85                  90                  95
Gln Tyr Asn Ser Thr Tyr Arg Val Val Ser Val Leu Thr Val Leu His
            100                 105                 110
Gln Asp Trp Leu Asn Gly Lys Glu Tyr Lys Cys Lys Val Ala Ser Tyr
            115                 120                 125
Asp Asp Tyr Thr Trp Phe Thr Tyr Glu Lys Thr Ile Ser Lys Ala Lys
            130                 135                 140
Gly Gln
145
```

```
<210> SEQ ID NO 110
<211> LENGTH: 147
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (64)..(82)
<220> FEATURE:
<221> NAME/KEY: Variant
<222> LOCATION: (123)..(142)

<400> SEQUENCE: 110

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His His
            20                  25                  30

His Ala Pro Glu Leu Leu Gly Gly Pro Ser Val Phe Leu Phe Pro Pro
        35                  40                  45

Lys Pro Lys Asp Thr Leu Met Ile Ser Arg Thr Pro Glu Val Thr Cys
50                  55                  60

Val Val Val Gly Tyr Ser Ile Ser Ser Asp Tyr Ala Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ala Arg Gly
        115                 120                 125

Tyr Tyr Gly Ser Ser His Ser Pro Val Glu Lys Thr Ile Ser Lys Ala
    130                 135                 140

Lys Gly Gln
145

<210> SEQ ID NO 111
<211> LENGTH: 148
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (64)..(83)
<220> FEATURE:
<221> NAME/KEY: Variant
<222> LOCATION: (124)..(143)

<400> SEQUENCE: 111

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His His
```

```
                  20                  25                  30
His Ala Pro Glu Leu Leu Gly Gly Pro Ser Val Phe Leu Phe Pro Pro
            35                  40                  45

Lys Pro Lys Asp Thr Leu Met Ile Ser Arg Thr Pro Glu Val Thr Cys
 50                  55                  60

Val Val Val Gly Phe Ser Leu Ser Thr Ser Gly Met Ser Phe Asn Trp
 65                  70                  75                  80

Tyr Val Asp Gly Val Glu Val His Asn Ala Lys Thr Lys Pro Arg Glu
                85                  90                  95

Glu Gln Tyr Asn Ser Thr Tyr Arg Val Val Ser Val Leu Thr Val Leu
                100                 105                 110

His Gln Asp Trp Leu Asn Gly Lys Glu Tyr Lys Cys Lys Val Ala Arg
            115                 120                 125

Arg Thr Thr Thr Ala Asp Tyr Phe Ala Tyr Glu Lys Thr Ile Ser Lys
            130                 135                 140

Ala Lys Gly Gln
145

<210> SEQ ID NO 112
<211> LENGTH: 149
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (64)..(83)
<220> FEATURE:
<221> NAME/KEY: Variant
<222> LOCATION: (124)..(143)

<400> SEQUENCE: 112

Met Lys Lys Ile Trp Leu Ala Leu Ala Gly Leu Val Leu Ala Phe Ser
 1               5                  10                  15

Ala Ser Ala Ala Gly Tyr Glu Asp Gly Lys Gly His His His His His
                20                  25                  30

His Ala Pro Glu Leu Leu Gly Gly Pro Ser Val Phe Leu Phe Pro Pro
            35                  40                  45

Lys Pro Lys Asp Thr Leu Met Ile Ser Arg Thr Pro Glu Val Thr Cys
 50                  55                  60

Val Val Val Gly Phe Ser Leu Ser Thr Tyr Gly Val Gly Phe Asn Trp
 65                  70                  75                  80

Tyr Val Asp Gly Val Glu Val His Asn Ala Lys Thr Lys Pro Arg Glu
                85                  90                  95

Glu Gln Tyr Asn Ser Thr Tyr Arg Val Val Ser Val Leu Thr Val Leu
                100                 105                 110

His Gln Asp Trp Leu Asn Gly Lys Glu Tyr Lys Cys Lys Val Ala Arg
            115                 120                 125

Leu Gly Ser Asp Tyr Asp Val Trp Phe Asp Tyr Glu Lys Thr Ile Ser
            130                 135                 140

Lys Ala Lys Gly Gln
145
```

```
<210> SEQ ID NO 113
<211> LENGTH: 150
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (64)..(83)
<220> FEATURE:
<221> NAME/KEY: Variant
<222> LOCATION: (124)..(143)

<400> SEQUENCE: 113

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
            20                  25                  30

His Ala Pro Glu Leu Leu Gly Gly Pro Ser Val Phe Leu Phe Pro Pro
        35                  40                  45

Lys Pro Lys Asp Thr Leu Met Ile Ser Arg Thr Pro Glu Val Thr Cys
    50                  55                  60

Val Val Val Gly Phe Ser Leu Thr Thr Tyr Gly Met Gly Phe Asn Trp
65                  70                  75                  80

Tyr Val Asp Gly Val Glu Val His Asn Ala Lys Thr Lys Pro Arg Glu
                85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Cys Lys Val Ala Arg
        115                 120                 125

Arg Ala Pro Phe Tyr Gly Asn His Ala Met Asp Tyr Glu Lys Thr Ile
    130                 135                 140

Ser Lys Ala Lys Gly Gln
145                 150

<210> SEQ ID NO 114
<211> LENGTH: 151
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (64)..(83)
<220> FEATURE:
<221> NAME/KEY: Variant
<222> LOCATION: (124)..(143)

<400> SEQUENCE: 114

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
            20                  25                  30
```

His Ala Pro Glu Leu Leu Gly Gly Pro Ser Val Phe Leu Phe Pro Pro
                35                  40                  45

Lys Pro Lys Asp Thr Leu Met Ile Ser Arg Thr Pro Glu Val Thr Cys
 50                  55                  60

Val Val Val Gly Phe Ser Leu Ser Thr Ser Gly Met Gly Phe Asn Trp
 65                  70                  75                  80

Tyr Val Asp Gly Val Glu Val His Asn Ala Lys Thr Lys Pro Arg Glu
                 85                  90                  95

Glu Gln Tyr Asn Ser Thr Tyr Arg Val Val Ser Val Leu Thr Val Leu
                100                 105                 110

His Gln Asp Trp Leu Asn Gly Lys Glu Tyr Lys Cys Lys Val Val Arg
            115                 120                 125

Arg Ala His Thr Thr Val Leu Gly Asp Trp Phe Ala Tyr Glu Lys Thr
130                 135                 140

Ile Ser Lys Ala Lys Gly Gln
145                 150

<210> SEQ ID NO 115
<211> LENGTH: 152
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (64)..(83)
<220> FEATURE:
<221> NAME/KEY: Variant
<222> LOCATION: (124)..(143)

<400> SEQUENCE: 115

Met Lys Lys Ile Trp Leu Ala Leu Ala Gly Leu Val Leu Ala Phe Ser
 1               5                  10                  15

Ala Ser Ala Ala Gly Tyr Glu Asp Gly Lys Gly His His His His His
                 20                  25                  30

His Ala Pro Glu Leu Leu Gly Gly Pro Ser Val Phe Leu Phe Pro Pro
                 35                  40                  45

Lys Pro Lys Asp Thr Leu Met Ile Ser Arg Thr Pro Glu Val Thr Cys
 50                  55                  60

Val Val Val Gly Phe Ser Leu Ser Thr Ser Gly Met Ser Phe Asn Trp
 65                  70                  75                  80

Tyr Val Asp Gly Val Glu Val His Asn Ala Lys Thr Lys Pro Arg Glu
                 85                  90                  95

Glu Gln Tyr Asn Ser Thr Tyr Arg Val Val Ser Val Leu Thr Val Leu
                100                 105                 110

His Gln Asp Trp Leu Asn Gly Lys Glu Tyr Lys Cys Lys Val Ala Arg
            115                 120                 125

Thr Leu Arg Val Ser Gly Asp Tyr Val Arg Asp Phe Asp Leu Glu Lys
130                 135                 140

Thr Ile Ser Lys Ala Lys Gly Gln
145                 150

<210> SEQ ID NO 116
<211> LENGTH: 153

```
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (64)..(83)
<220> FEATURE:
<221> NAME/KEY: Variant
<222> LOCATION: (124)..(143)

<400> SEQUENCE: 116

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
            20                  25                  30

His Ala Pro Glu Leu Leu Gly Gly Pro Ser Val Phe Leu Phe Pro Pro
        35                  40                  45

Lys Pro Lys Asp Thr Leu Met Ile Ser Arg Thr Pro Glu Val Thr Cys
50                  55                  60

Val Val Val Gly Phe Ser Ile Arg Thr Ser Lys Val Gly Phe Asn Trp
65                  70                  75                  80

Tyr Val Asp Gly Val Glu Val His Asn Ala Lys Thr Lys Pro Arg Glu
            85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Cys Lys Val Ala Arg
        115                 120                 125

Arg Gly Phe Tyr Gly Arg Lys Tyr Glu Val Asn His Phe Asp Tyr Glu
    130                 135                 140

Lys Thr Ile Ser Lys Ala Lys Gly Gln
145                 150

<210> SEQ ID NO 117
<211> LENGTH: 154
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (64)..(83)
<220> FEATURE:
<221> NAME/KEY: Variant
<222> LOCATION: (124)..(152)

<400> SEQUENCE: 117

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
            20                  25                  30

His Ala Pro Glu Leu Leu Gly Gly Pro Ser Val Phe Leu Phe Pro Pro
        35                  40                  45
```

```
Lys Pro Lys Asp Thr Leu Met Ile Ser Arg Thr Pro Glu Val Thr Cys
         50                  55                  60

Val Val Val Gly Phe Ser Leu Ser Thr Ser Gly Met Gly Phe Asn Trp
 65                  70                  75                  80

Tyr Val Asp Gly Val Glu Val His Asn Ala Lys Thr Lys Pro Arg Glu
                 85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Cys Lys Val Ala Arg
            115                 120                 125

Arg Thr Phe Ser Tyr Tyr Tyr Gly Ser Ser Phe Tyr Tyr Phe Asp Asn
            130                 135                 140

Glu Lys Thr Ile Ser Lys Ala Lys Gly Gln
145                 150

<210> SEQ ID NO 118
<211> LENGTH: 160
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (64)..(83)
<220> FEATURE:
<221> NAME/KEY: Variant
<222> LOCATION: (124)..(153)

<400> SEQUENCE: 118

Met Lys Lys Ile Trp Leu Ala Leu Ala Gly Leu Val Leu Ala Phe Ser
  1               5                  10                  15

Ala Ser Ala Ala Gly Tyr Glu Asp Gly Lys Gly His His His His His
                 20                  25                  30

His Ala Pro Glu Leu Leu Gly Gly Pro Ser Val Phe Leu Phe Pro Pro
             35                  40                  45

Lys Pro Lys Asp Thr Leu Met Ile Ser Arg Thr Pro Glu Val Thr Cys
         50                  55                  60

Val Val Val Gly Phe Ser Leu Ser Asp Phe Val Gly Phe Asn Trp
 65                  70                  75                  80

Tyr Val Asp Gly Val Glu Val His Asn Ala Lys Thr Lys Pro Arg Glu
                 85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Cys Lys Val Ala His
            115                 120                 125

Arg Arg Gly Pro Thr Thr Leu Phe Gly Val Pro Ile Ala Arg Gly Pro
            130                 135                 140

Val Asn Ala Met Asp Val Glu Leu Thr Ile Ser Lys Ala Lys Gly Gln
145                 150                 155                 160

<210> SEQ ID NO 119
<211> LENGTH: 148
<212> TYPE: PRT
<213> ORGANISM: Artificial Sequence
```

```
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (64)..(83)
<220> FEATURE:
<221> NAME/KEY: Variant
<222> LOCATION: (124)..(144)

<400> SEQUENCE: 119

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
            20                  25                  30

His Ala Pro Glu Leu Leu Gly Gly Pro Ser Val Phe Leu Phe Pro Pro
            35                  40                  45

Lys Pro Lys Asp Thr Leu Met Ile Ser Arg Thr Pro Glu Val Thr Cys
    50                  55                  60

Val Val Val Ala Arg Arg Thr Thr Thr Ala Asp Tyr Phe Ala Tyr Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Gly Phe Ser Leu Ser Thr Ser Gly Met Ser Glu Lys Thr Ile Ser Lys
    130                 135                 140

Ala Lys Gly Gln
145

<210> SEQ ID NO 120
<211> LENGTH: 149
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (64)..(83)
<220> FEATURE:
<221> NAME/KEY: Variant
<222> LOCATION: (124)..(144)

<400> SEQUENCE: 120

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
            20                  25                  30

His Ala Pro Glu Leu Leu Gly Gly Pro Ser Val Phe Leu Phe Pro Pro
            35                  40                  45

Lys Pro Lys Asp Thr Leu Met Ile Ser Arg Thr Pro Glu Val Thr Cys
```

```
                   50                  55                  60
Val Val Val Ala Arg Leu Gly Ser Asp Tyr Asp Val Trp Phe Asp Tyr
 65                  70                  75                  80

Phe Asn Trp Tyr Val Asp Gly Val Glu Val His Asn Ala Lys Thr Lys
                 85                  90                  95

Pro Arg Glu Glu Gln Tyr Asn Ser Thr Tyr Arg Val Val Ser Val Leu
                100                 105                 110

Thr Val Leu His Gln Asp Trp Leu Asn Gly Lys Glu Tyr Lys Cys Lys
            115                 120                 125

Val Gly Phe Ser Leu Ser Thr Tyr Gly Val Gly Glu Lys Thr Ile Ser
        130                 135                 140

Lys Ala Lys Gly Gln
145

<210> SEQ ID NO 121
<211> LENGTH: 150
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (64)..(82)
<220> FEATURE:
<221> NAME/KEY: Variant
<222> LOCATION: (128)..(148)

<400> SEQUENCE: 121

Met Lys Lys Ile Trp Leu Ala Leu Ala Gly Leu Val Leu Ala Phe Ser
  1               5                  10                  15

Ala Ser Ala Ala Gly Tyr Glu Asp Gly Lys Gly His His His His His
                 20                  25                  30

His Ala Pro Glu Leu Leu Gly Gly Pro Ser Val Phe Leu Phe Pro Pro
             35                  40                  45

Lys Pro Lys Asp Thr Leu Met Ile Ser Arg Thr Pro Glu Val Thr Cys
 50                  55                  60

Val Val Val Ala Arg Arg Ala Pro Phe Tyr Gly Asn His Ala Met Asp
 65                  70                  75                  80

Tyr Phe Asn Trp Tyr Val Asp Gly Val Glu Val His Asn Ala Lys Thr
                 85                  90                  95

Lys Pro Arg Glu Glu Gln Tyr Asn Ser Thr Tyr Arg Val Val Ser Val
                100                 105                 110

Leu Thr Val Leu His Gln Asp Trp Leu Asn Gly Lys Glu Tyr Lys Cys
            115                 120                 125

Lys Val Gly Phe Ser Leu Thr Thr Tyr Gly Met Gly Glu Lys Thr Ile
        130                 135                 140

Ser Lys Ala Lys Gly Gln
145                 150

<210> SEQ ID NO 122
<211> LENGTH: 151
<212> TYPE: PRT
<213> ORGANISM: Artificial Sequence
<220> FEATURE:
<223> OTHER INFORMATION: Example of variant CH2 molecule
```

```
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (64)..(83)
<220> FEATURE:
<221> NAME/KEY: Variant
<222> LOCATION: (129)..(139)

<400> SEQUENCE: 122

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
            20                  25                  30

His Ala Pro Glu Leu Leu Gly Gly Pro Ser Val Phe Leu Phe Pro Pro
            35                  40                  45

Lys Pro Lys Asp Thr Leu Met Ile Ser Arg Thr Pro Glu Val Thr Cys
    50                  55                  60

Val Val Val Val Arg Arg Ala His Thr Thr Val Leu Gly Asp Trp Phe
65                  70                  75                  80

Ala Tyr Phe Asn Trp Tyr Val Asp Gly Val Glu Val His Asn Ala Lys
                85                  90                  95

Thr Lys Pro Arg Glu Glu Gln Tyr Asn Ser Thr Tyr Arg Val Val Ser
            100                 105                 110

Val Leu Thr Val Leu His Gln Asp Trp Leu Asn Gly Lys Glu Tyr Lys
            115                 120                 125

Cys Lys Val Gly Phe Ser Leu Ser Thr Ser Gly Met Gly Glu Lys Thr
    130                 135                 140

Ile Ser Lys Ala Lys Gly Gln
145                 150

<210> SEQ ID NO 123
<211> LENGTH: 152
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (64)..(83)
<220> FEATURE:
<221> NAME/KEY: Variant
<222> LOCATION: (130)..(150)

<400> SEQUENCE: 123

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
            20                  25                  30

His Ala Pro Glu Leu Leu Gly Gly Pro Ser Val Phe Leu Phe Pro Pro
            35                  40                  45

Lys Pro Lys Asp Thr Leu Met Ile Ser Arg Thr Pro Glu Val Thr Cys
    50                  55                  60
```

```
Val Val Val Ala Arg Thr Leu Arg Val Ser Gly Asp Tyr Val Arg Asp
 65                  70                  75                  80

Phe Asp Leu Phe Asn Trp Tyr Val Asp Gly Val Glu Val His Asn Ala
                 85                  90                  95

Lys Thr Lys Pro Arg Glu Glu Gln Tyr Asn Ser Thr Tyr Arg Val Val
                100                 105                 110

Ser Val Leu Thr Val Leu His Gln Asp Trp Leu Asn Gly Lys Glu Tyr
            115                 120                 125

Lys Cys Lys Val Gly Phe Ser Leu Ser Thr Ser Gly Met Ser Glu Lys
        130                 135                 140

Thr Ile Ser Lys Ala Lys Gly Gln
145                 150
```

<210> SEQ ID NO 124
<211> LENGTH: 153
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (64)..(90)
<220> FEATURE:
<221> NAME/KEY: Variant
<222> LOCATION: (131)..(151)

<400> SEQUENCE: 124

```
Met Lys Lys Ile Trp Leu Ala Leu Ala Gly Leu Val Leu Ala Phe Ser
 1               5                  10                  15

Ala Ser Ala Ala Gly Tyr Glu Asp Gly Lys Gly His His His His His
                 20                  25                  30

His Ala Pro Glu Leu Leu Gly Gly Pro Ser Val Phe Leu Phe Pro Pro
             35                  40                  45

Lys Pro Lys Asp Thr Leu Met Ile Ser Arg Thr Pro Glu Val Thr Cys
         50                  55                  60

Val Val Val Ala Arg Arg Gly Phe Tyr Gly Arg Lys Tyr Glu Val Asn
 65                  70                  75                  80

His Phe Asp Tyr Phe Asn Trp Tyr Val Asp Gly Val Glu Val His Asn
                 85                  90                  95

Ala Lys Thr Lys Pro Arg Glu Glu Gln Tyr Asn Ser Thr Tyr Arg Val
                100                 105                 110

Val Ser Val Leu Thr Val Leu His Gln Asp Trp Leu Asn Gly Lys Glu
            115                 120                 125

Tyr Lys Cys Lys Val Gly Phe Ser Ile Arg Thr Ser Lys Val Gly Glu
        130                 135                 140

Lys Thr Ile Ser Lys Ala Lys Gly Gln
145                 150
```

<210> SEQ ID NO 125
<211> LENGTH: 154
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING

```
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (64)..(91)
<220> FEATURE:
<221> NAME/KEY: Variant
<222> LOCATION: (132)..(152)

<400> SEQUENCE: 125

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
            20                  25                  30

His Ala Pro Glu Leu Leu Gly Gly Pro Ser Val Phe Leu Phe Pro Pro
        35                  40                  45

Lys Pro Lys Asp Thr Leu Met Ile Ser Arg Thr Pro Glu Val Thr Cys
50                  55                  60

Val Val Val Ala Arg Arg Thr Phe Ser Tyr Tyr Tyr Gly Ser Ser Phe
65                  70                  75                  80

Tyr Tyr Phe Asp Asn Phe Asn Trp Tyr Val Asp Gly Val Glu Val His
                85                  90                  95

Asn Ala Lys Thr Lys Pro Arg Glu Glu Gln Tyr Asn Ser Thr Tyr Arg
            100                 105                 110

Val Val Ser Val Leu Thr Val Leu His Gln Asp Trp Leu Asn Gly Lys
        115                 120                 125

Glu Tyr Lys Cys Lys Val Gly Phe Ser Leu Ser Thr Ser Gly Met Gly
    130                 135                 140

Glu Lys Thr Ile Ser Lys Ala Lys Gly Gln
145                 150

<210> SEQ ID NO 126
<211> LENGTH: 160
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (64)..(93)
<220> FEATURE:
<221> NAME/KEY: Variant
<222> LOCATION: (138)..(158)

<400> SEQUENCE: 126

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
            20                  25                  30

His Ala Pro Glu Leu Leu Gly Gly Pro Ser Val Phe Leu Phe Pro Pro
        35                  40                  45

Lys Pro Lys Asp Thr Leu Met Ile Ser Arg Thr Pro Glu Val Thr Cys
50                  55                  60

Val Val Val Ala His Arg Gly Pro Thr Thr Leu Phe Gly Val Pro
65                  70                  75                  80
```

```
Ile Ala Arg Gly Pro Val Asn Ala Met Asp Val Phe Asn Trp Tyr Val
                85                  90                  95

Asp Gly Val Glu Val His Asn Ala Lys Thr Lys Pro Arg Glu Glu Gln
            100                 105                 110

Tyr Asn Ser Thr Tyr Arg Val Val Ser Val Leu Thr Val Leu His Gln
        115                 120                 125

Asp Trp Leu Asn Gly Lys Glu Tyr Lys Cys Lys Val Gly Phe Ser Leu
130                 135                 140

Ser Asp Phe Gly Val Gly Glu Lys Thr Ile Ser Lys Ala Lys Gly Gln
145                 150                 155                 160

<210> SEQ ID NO 127
<211> LENGTH: 145
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (64)..(82)
<220> FEATURE:
<221> NAME/KEY: Variant
<222> LOCATION: (93)..(112)
<220> FEATURE:
<221> NAME/KEY: Variant
<222> LOCATION: (123)..(143)

<400> SEQUENCE: 127

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His His
            20                  25                  30

His Ala Pro Glu Leu Leu Gly Gly Pro Ser Val Phe Leu Phe Pro Pro
        35                  40                  45

Lys Pro Lys Asp Thr Leu Met Ile Ser Arg Thr Pro Glu Val Thr Cys
50                  55                  60

Val Val Val Ser Asn Lys Ala Leu Pro Ala Pro Ile Phe Asn Trp Tyr
65                  70                  75                  80

Val Asp Gly Val Glu Val His Asn Ala Lys Thr Lys Pro Arg Cys Glu
            85                  90                  95

Gln Tyr Asn Ser Thr Tyr Cys Val Val Ser Val Leu Thr Val Leu His
        100                 105                 110

Gln Asp Trp Leu Asn Gly Lys Glu Tyr Lys Cys Lys Val Asp Val Ser
        115                 120                 125

His Glu Asp Pro Glu Val Lys Glu Lys Thr Ile Ser Lys Ala Lys Gly
        130                 135                 140

Gln
145

<210> SEQ ID NO 128
<211> LENGTH: 145
<212> TYPE: PRT
<213> ORGANISM: Artificial Sequence
<220> FEATURE:
<223> OTHER INFORMATION: Example of variant CH2 molecule
<220> FEATURE:
```

```
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (64)..(82)
<220> FEATURE:
<221> NAME/KEY: Variant
<222> LOCATION: (123)..(143)

<400> SEQUENCE: 128

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
            20                  25                  30

His Ala Pro Glu Leu Leu Gly Gly Pro Ser Val Phe Leu Phe Pro Pro
            35                  40                  45

Lys Pro Lys Asp Thr Leu Met Ile Ser Arg Thr Pro Glu Val Thr Cys
50                  55                  60

Val Val Val Ser Asn Lys Ala Leu Pro Ala Pro Ile Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Asp Val Ser
            115                 120                 125

His Glu Asp Pro Glu Val Lys Glu Lys Thr Ile Ser Lys Ala Lys Gly
            130                 135                 140

Gln
145

<210> SEQ ID NO 129
<211> LENGTH: 146
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (34)..(43)
<220> FEATURE:
<221> NAME/KEY: Variant
<222> LOCATION: (134)..(144)

<400> SEQUENCE: 129

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
            20                  25                  30

His Ala Pro Glu Leu Leu Gly Gly Pro Ser Cys Phe Leu Phe Pro Pro
            35                  40                  45

Lys Pro Lys Asp Thr Leu Met Ile Ser Arg Thr Pro Glu Val Thr Cys
50                  55                  60

Val Val Val Asp Val Ser His Glu Asp Pro Glu Val Lys Phe Asn Trp
```

```
                65                  70                  75                  80
Tyr Val Asp Gly Val Glu Val His Asn Ala Lys Thr Lys Pro Arg Glu
                    85                  90                  95

Glu Gln Tyr Asn Ser Thr Tyr Arg Val Val Ser Val Leu Thr Val Leu
                100                 105                 110

His Gln Asp Trp Leu Asn Gly Lys Glu Tyr Lys Cys Lys Val Ser Asn
            115                 120                 125

Lys Ala Leu Pro Ala Pro Ile Cys Glu Lys Thr Ile Ser Lys Ala Lys
        130                 135                 140

Gly Gln
145

<210> SEQ ID NO 130
<211> LENGTH: 145
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (34)..(43)
<220> FEATURE:
<221> NAME/KEY: Variant
<222> LOCATION: (134)..(143)

<400> SEQUENCE: 130

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His His
                20                  25                  30

His Ala Pro Glu Leu Leu Gly Gly Pro Ser Cys Phe Leu Phe Pro Pro
            35                  40                  45

Lys Pro Lys Asp Thr Leu Met Ile Ser Arg Thr Pro Glu Val Thr Cys
50                  55                  60

Val Val Val Asp Val Ser His Glu Asp Pro Glu Val Lys Phe Asn Trp
65                  70                  75                  80

Tyr Val Asp Gly Val Glu Val His Asn Ala Lys Thr Lys Pro Arg Glu
                    85                  90                  95

Glu Gln Tyr Asn Ser Thr Tyr Arg Val Val Ser Val Leu Thr Val Leu
                100                 105                 110

His Gln Asp Trp Leu Asn Gly Lys Glu Tyr Lys Cys Lys Val Ser Asn
            115                 120                 125

Lys Ala Leu Pro Ala Pro Cys Glu Lys Thr Ile Ser Lys Ala Lys Gly
        130                 135                 140

Gln
145

<210> SEQ ID NO 131
<211> LENGTH: 146
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
```

```
<220> FEATURE:
<221> NAME/KEY: Binding
<222> LOCATION: (24)..(33)
<220> FEATURE:
<221> NAME/KEY: Variant
<222> LOCATION: (34)..(43)
<220> FEATURE:
<221> NAME/KEY: Variant
<222> LOCATION: (134)..(144)

<400> SEQUENCE: 131

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
            20                  25                  30

His Ala Pro Glu Leu Leu Gly Gly Pro Cys Val Phe Leu Phe Pro Pro
            35                  40                  45

Lys Pro Lys Asp Thr Leu Met Ile Ser Arg Thr Pro Glu Val Thr Cys
50                  55                  60

Val Val Val Asp Val Ser His Glu Asp Pro Glu Val Lys Phe Asn Trp
65                  70                  75                  80

Tyr Val Asp Gly Val Glu Val His Asn Ala Lys Thr Lys Pro Arg Glu
                85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Cys Lys Val Ser Asn
        115                 120                 125

Lys Ala Leu Pro Ala Pro Ile Cys Glu Lys Thr Ile Ser Lys Ala Lys
130                 135                 140

Gly Gln
145

<210> SEQ ID NO 132
<211> LENGTH: 145
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (34)..(43)
<220> FEATURE:
<221> NAME/KEY: Variant
<222> LOCATION: (134)..(143)

<400> SEQUENCE: 132

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
            20                  25                  30

His Ala Pro Glu Leu Leu Gly Gly Pro Cys Val Phe Leu Phe Pro Pro
            35                  40                  45

Lys Pro Lys Asp Thr Leu Met Ile Ser Arg Thr Pro Glu Val Thr Cys
50                  55                  60

Val Val Val Asp Val Ser His Glu Asp Pro Glu Val Lys Phe Asn Trp
65                  70                  75                  80
```

```
Tyr Val Asp Gly Val Glu Val His Asn Ala Lys Thr Lys Pro Arg Glu
                85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Cys Lys Val Ser Asn
        115                 120                 125

Lys Ala Leu Pro Ala Pro Cys Glu Lys Thr Ile Ser Lys Ala Lys Gly
    130                 135                 140

Gln
145

<210> SEQ ID NO 133
<211> LENGTH: 146
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (44)..(53)
<220> FEATURE:
<221> NAME/KEY: Variant
<222> LOCATION: (134)..(144)

<400> SEQUENCE: 133

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
            20                  25                  30

His Ala Pro Glu Leu Leu Gly Gly Pro Ser Val Phe Leu Phe Cys Pro
        35                  40                  45

Lys Pro Lys Asp Thr Leu Met Ile Ser Arg Thr Pro Glu Val Thr Cys
    50                  55                  60

Val Val Val Asp Val Ser His Glu Asp Pro Glu Val Lys Phe Asn Trp
65                  70                  75                  80

Tyr Val Asp Gly Val Glu Val His Asn Ala Lys Thr Lys Pro Arg Glu
                85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Cys Lys Val Ser Asn
        115                 120                 125

Lys Ala Leu Pro Ala Pro Ile Glu Lys Thr Ile Cys Ser Lys Ala Lys
    130                 135                 140

Gly Gln
145

<210> SEQ ID NO 134
<211> LENGTH: 145
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
```

```
<222> LOCATION: (24)..(33)
<220> FEATURE:
<221> NAME/KEY: Variant
<222> LOCATION: (44)..(53)
<220> FEATURE:
<221> NAME/KEY: Variant
<222> LOCATION: (134)..(143)

<400> SEQUENCE: 134
```

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
            20                  25                  30

His Ala Pro Glu Leu Leu Gly Gly Pro Ser Val Phe Leu Phe Cys Pro
            35                  40                  45

Lys Pro Lys Asp Thr Leu Met Ile Ser Arg Thr Pro Glu Val Thr Cys
50                  55                  60

Val Val Val Asp Val Ser His Glu Asp Pro Glu Val Lys Phe Asn Trp
65                  70                  75                  80

Tyr Val Asp Gly Val Glu Val His Asn Ala Lys Thr Lys Pro Arg Glu
            85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Cys Lys Val Ser Asn
            115                 120                 125

Lys Ala Leu Pro Ala Pro Ile Glu Lys Thr Cys Ser Lys Ala Lys Gly
            130                 135                 140

Gln
145

```
<210> SEQ ID NO 135
<211> LENGTH: 145
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (94)..(134)

<400> SEQUENCE: 135
```

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
            20                  25                  30

His Ala Pro Glu Leu Leu Gly Gly Pro Ser Val Phe Leu Phe Pro Pro
            35                  40                  45

Lys Pro Lys Asp Thr Leu Met Ile Ser Arg Thr Pro Glu Val Thr Cys
50                  55                  60

Val Val Val Asp Val Ser His Glu Asp Pro Glu Val Lys Phe Asn Trp
65                  70                  75                  80

Tyr Val Asp Gly Val Glu Val His Asn Ala Lys Thr Lys Pro Arg Cys
            85                  90                  95

Glu Gln Tyr Asn Ser Thr Tyr Cys Val Val Ser Val Leu Thr Val Leu
            100                 105                 110

-continued

His Gln Asp Trp Leu Asn Gly Lys Glu Tyr Lys Cys Lys Val Ser Asn
        115                 120                 125

Lys Ala Leu Pro Ala Pro Ile Glu Lys Thr Ile Ser Lys Ala Lys Gly
        130                 135                 140

Gln
145

<210> SEQ ID NO 136
<211> LENGTH: 145
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (44)..(53)
<220> FEATURE:
<221> NAME/KEY: Variant
<222> LOCATION: (134)..(143)

<400> SEQUENCE: 136

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His His
            20                  25                  30

His Ala Pro Glu Leu Leu Gly Gly Pro Ser Val Phe Cys Phe Pro Pro
        35                  40                  45

Lys Pro Lys Asp Thr Leu Met Ile Ser Arg Thr Pro Glu Val Thr Cys
        50                  55                  60

Val Val Val Asp Val Ser His Glu Asp Pro Glu Val Lys Phe Asn Trp
65                  70                  75                  80

Tyr Val Asp Gly Val Glu Val His Asn Ala Lys Thr Lys Pro Arg Glu
                85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Cys Lys Val Ser Asn
        115                 120                 125

Lys Ala Leu Pro Ala Pro Ile Glu Cys Thr Ile Ser Lys Ala Lys Gly
        130                 135                 140

Gln
145

<210> SEQ ID NO 137
<211> LENGTH: 145
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (64)..(73)
<220> FEATURE:

-continued

```
<221> NAME/KEY: Variant
<222> LOCATION: (124)..(133)

<400> SEQUENCE: 137

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
            20                  25                  30

His Ala Pro Glu Leu Leu Gly Gly Pro Ser Val Phe Leu Phe Pro Pro
        35                  40                  45

Lys Pro Lys Asp Thr Leu Met Ile Ser Arg Thr Pro Glu Val Thr Ala
    50                  55                  60

Val Val Val Asp Val Ser His Glu Asp Pro Glu Val Lys Phe Asn Trp
65                  70                  75                  80

Tyr Val Asp Gly Val Glu Val His Asn Ala Lys Thr Lys Pro Arg Glu
                85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Ala Lys Val Ser Asn
        115                 120                 125

Lys Ala Leu Pro Ala Pro Ile Glu Lys Thr Ile Ser Lys Ala Lys Gly
    130                 135                 140

Gln
145

<210> SEQ ID NO 138
<211> LENGTH: 145
<212> TYPE: PRT
<213> ORGANISM: Artificial Sequence
<220> FEATURE:
<223> OTHER INFORMATION: Example of variant CH2 molecule
<220> FEATURE:
<221> NAME/KEY: BINDING
<222> LOCATION: (1)..(23)
<220> FEATURE:
<221> NAME/KEY: Binding
<222> LOCATION: (24)..(33)
<220> FEATURE:
<221> NAME/KEY: Variant
<222> LOCATION: (44)..(63)
<220> FEATURE:
<221> NAME/KEY: Variant
<222> LOCATION: (104)..(113)
<220> FEATURE:
<221> NAME/KEY: Variant
<222> LOCATION: (134)..(143)

<400> SEQUENCE: 138

Met Lys Lys Ile Trp Leu Ala Leu Ala Gly Leu Val Leu Ala Phe Ser
1               5                   10                  15

Ala Ser Ala Ala Gly Tyr Glu Asp Gly Lys Gly His His His His
            20                  25                  30

His Ala Pro Glu Leu Leu Gly Gly Pro Ser Val Phe Cys Phe Pro Pro
        35                  40                  45

Lys Pro Lys Asp Thr Leu Tyr Ile Thr Arg Glu Pro Glu Val Thr Cys
    50                  55                  60

Val Val Val Asp Val Ser His Glu Asp Pro Glu Val Lys Phe Asn Trp
65                  70                  75                  80

Tyr Val Asp Gly Val Glu Val His Asn Ala Lys Thr Lys Pro Arg Glu
                85                  90                  95

Glu Gln Tyr Asn Ser Thr Tyr Arg Val Val Ser Val Leu Ala Val Leu
```

```
                100             105             110
His Gln Asp Trp Leu Asn Gly Lys Glu Tyr Lys Cys Lys Val Ser Asn
        115                 120                 125

Lys Ala Leu Pro Ala Pro Ile Glu Cys Thr Ile Ser Lys Ala Lys Gly
        130                 135                 140

Gln
145
```

<210> SEQ ID NO 139
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 139

```
Gln Tyr Asn Ser
1
```

<210> SEQ ID NO 140
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 140

```
Gly Ser Gly Ser
1
```

<210> SEQ ID NO 141
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 141

```
Met Lys Lys Ile Trp Leu Ala Leu Ala Gly Leu Val Leu Ala Phe Ser
1               5                   10                  15

Ala Ser Ala Ala Gly Tyr Glu
            20
```

<210> SEQ ID NO 142
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 142

```
Asp Gly Lys Gly His His His His His His Ala Pro Glu Leu Leu
1               5                   10                  15
```

<210> SEQ ID NO 143
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 143

```
Gly Gly Pro Ser Val Phe Leu Phe Pro Pro Lys Pro Lys Asp Thr Leu
1               5                   10                  15
```

```
Met Ile Ser Arg Thr Pro Glu Val Thr Cys Val Val Val
            20                  25
```

<210> SEQ ID NO 144
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 144

```
Phe Asn Trp Tyr Val Asp Gly Val Glu Val His Asn Ala Lys Thr Lys
1               5                   10                  15

Pro Arg
```

<210> SEQ ID NO 145
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 145

```
Thr Tyr Arg Val Val Ser Val Leu Thr Val Leu His Gln Asp Trp Leu
1               5                   10                  15

Asn Gly Lys Glu Tyr Lys Cys Lys Val
            20                  25
```

<210> SEQ ID NO 146
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 146

```
Glu Lys Thr Ile Ser Lys Ala Lys Gly Gln
1               5                   10
```

<210> SEQ ID NO 147
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 147

```
Cys Glu Gln Tyr Asn Ser
1               5
```

<210> SEQ ID NO 148
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 148

```
Thr Tyr Cys Val Val Ser Val Leu Thr Val Leu His Gln Asp Trp Leu
1               5                   10                  15

Asn Gly Lys Glu Tyr Lys Cys Lys Val
            20                  25
```

<210> SEQ ID NO 149
<211> LENGTH: 29

<212> TYPE: PRT
<213> ORGANISM: Artificial Sequence
<220> FEATURE:
<223> OTHER INFORMATION: Synthetic Peptide

<400> SEQUENCE: 149

Gly Gly Pro Ser Cys Phe Leu Phe Pro Lys Pro Lys Asp Thr Leu
1               5                   10                  15

Met Ile Ser Arg Thr Pro Glu Val Thr Cys Val Val Val
            20                  25

<210> SEQ ID NO 150
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 150

Ser Asn Lys Ala Leu Pro Ala Pro Cys
1               5

<210> SEQ ID NO 151
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 151

Gly Gly Pro Cys Val Phe Leu Phe Pro Lys Pro Lys Asp Thr Leu
1               5                   10                  15

Met Ile Ser Arg Thr Pro Glu Val Thr Cys Val Val Val
            20                  25

<210> SEQ ID NO 152
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 152

Gly Gly Pro Ser Val Phe Leu Phe Cys Pro Lys Pro Lys Asp Thr Leu
1               5                   10                  15

Met Ile Ser Arg Thr Pro Glu Val Thr Cys Val Val Val
            20                  25

<210> SEQ ID NO 153
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 153

Glu Lys Thr Ile Cys Ser Lys Ala Lys Gly Gln
1               5                   10

<210> SEQ ID NO 154
<211> LENGTH: 10
<212> TYPE: PRT
<213> ORGANISM: Artificial Sequence
<220> FEATURE:
<223> OTHER INFORMATION: Synthetic Peptide

```
<400> SEQUENCE: 154

Glu Lys Thr Cys Ser Lys Ala Lys Gly Gln
1               5                   10

<210> SEQ ID NO 155
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 155

Gly Gly Pro Ser Val Phe Cys Phe Pro Pro Lys Pro Lys Asp Thr Leu
1               5                   10                  15

Met Ile Ser Arg Thr Pro Glu Val Thr Cys Val Val Val
            20                  25

<210> SEQ ID NO 156
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 156

Glu Cys Thr Ile Ser Lys Ala Lys Gly Gln
1               5                   10

<210> SEQ ID NO 157
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 157

Gly Gly Pro Ser Val Phe Leu Phe Pro Pro Lys Pro Lys Asp Thr Leu
1               5                   10                  15

Met Ile Ser Arg Thr Pro Glu Val Thr Ala Val Val Val
            20                  25

<210> SEQ ID NO 158
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 158

Thr Tyr Arg Val Val Ser Val Leu Thr Val Leu His Gln Asp Trp Leu
1               5                   10                  15

Asn Gly Lys Glu Tyr Lys Ala Lys Val
            20                  25

<210> SEQ ID NO 159
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 159

Gly Gly Pro Ser Val Phe Cys Phe Pro Pro Lys Pro Lys Asp Thr Leu
1               5                   10                  15
```

```
Tyr Ile Thr Arg Glu Pro Glu Val Thr Cys Val Val Val
            20                  25

<210> SEQ ID NO 160
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 160

Thr Tyr Arg Val Val Ser Val Leu Ala Val Leu His Gln Asp Trp Leu
1               5                   10                  15

Asn Gly Lys Glu Tyr Lys Cys Lys Val
            20                  25
```

US 9,156,917 B2

CH2 DOMAIN TEMPLATE MOLECULES DERIVED FROM RATIONAL GRAFTING OF DONOR LOOPS ONTO CH2 SCAFFOLDS

CROSS-REFERENCE TO RELATED APPLICATIONS

The present application is a non-provisional application that claims priority to U.S. Provisional Patent Application Ser. No. 61/441,967 filed Feb. 11, 2011, the disclosure of which is incorporated in its entirety herein by reference.

INCORPORATION BY REFERENCE OF SEQUENCE LISTING

The Sequence Listing in an ASCII text file, named 29643_SubstituteSEQ051415.txt of 143 KB, created May 18, 2015, and submitted to the United States Patent and Trademark Office via EFS-Web, is incorporated herein by reference.

FIELD OF THE INVENTION

The present invention is directed to the field of immunology, particularly to CH2 domains or equivalent CH2-like domains of immunoglobulins used as scaffolds onto which donor loops are grafted to replace the loops of the scaffold, the donor loops having lengths identical or similar to the loops of the CH2 domain scaffold.

BACKGROUND OF THE INVENTION

Immunoglobulins (antibodies) in adult humans are categorized into five different isotypes: IgA, IgD, IgE, IgG, and IgM. The isotypes vary in size and sequence. On average, each immunoglobulin has a molecular weight of about 150 kDa. It is well known that each immunoglobulin comprises two heavy chains (H) and two light chains (L), which are arranged to form a Y-shaped molecule. The Y-shape can be conceptually divided into the $F_{ab}$ region, which represents the top portion of the Y-shaped molecule, and the $F_c$ region, which represents the bottom portion of the Y-shaped molecule.

The heavy chains in IgG, IgA, and IgD each have a variable domain (VH) at one end followed by three constant domains: CH1, CH2, and CH3. The CH1 and CH2 regions are joined by a distinct hinge region. A CH2 domain may or may not include the hinge region. The heavy chains in IgM and IgE each have a variable domain (VH) at one end followed by four constant domains: CH1, CH2, CH3, and CH4. Sequences of the variable domains vary, but the constant domains are generally conserved among all antibodies in the same isotype.

The $F_{ab}$ region of immunoglobulins contains the variable (V) domain and the CH1 domain; the $F_c$ region of immunoglobulins contains the hinge region and the remaining constant domains, either CH2 and CH3 in IgG, IgA, and IgD, or CH2, CH3, and CH4 in IgM and IgE.

Target antigen specificity of the immunoglobulins is conferred by the paratope in the $F_{ab}$ region. Effector functions (e.g., complement activation, interaction with $F_c$ receptors such as pro-inflammatory $F_c\gamma$ receptors, binding to various immune cells such as phagocytes, lymphocytes, platelets, mast cells, and the like) of the immunoglobulins are conferred by the $F_c$ region. The $F_c$ region is also important for maintaining serum half-life. Serum half-life of an immunoglobulin is mediated by the binding of the $F_c$ region to the neonatal receptor FcRn. The alpha domain is the portion of FcRn that interacts with the CH2 domain (and possibly CH3 domain) of IgG, and possibly IgA, and IgD or with the CH3 domain (and possibly CH4 domain) of IgM and IgE.

Examining the constant domains of the immunoglobulin heavy chains more closely, the CH3 domains of IgM and IgE are closely related to the CH2 domain in terms of sequence and function. Without wishing to limit the present invention to any theory or mechanism, it is believed that the CH2 domain (or the equivalent CH3 domain of IgM or IgE) is responsible for all or most of the interaction with $F_c$ receptors (e.g., $F_c\gamma$ receptors), and contains histidine (His) residues important for serum half-life maintenance. The CH2 domain (or the equivalent CH3 domain of IgM or IgE) also has binding sites for complement. The CH2/CH3 domain's retention of functional characteristics of the antibody from which it is derived (e.g., interaction with $F_c\gamma$ receptors, binding sites for complement, solubility, stability/half-life, etc.) is discussed in Dimitrov (2009) mAbs 1:1-3 and Dimitrov (2009) mAbs 1:26-28 and Prabakaran et al. (2008, Biological Crystallography 64:1062-1067). Consequently, CH2 domains have been used as scaffolds as alternatives to full-length antibodies.

Without wishing to limit the present invention to any theory or mechanisms, it is believed that some modifications to the CH2 domain may have only small effects on the overall structure of the CH2 domain (or CH2-like domain), and it is likely that in cases where the modified CH2 structure was similar to the wild-type CH2 structure the modified CH2 domain would confer the same functional characteristics as the wild-type CH2 domain possessed in the full immunoglobulin molecule.

It is known that efficacy of a therapeutic antibody (or fragment thereof) can be limited by an immune reaction. To address such issues, many methods have been used to humanize antibodies derived from a non-human source with the aim of reducing the human anti-murine antibody (HAMA) response, for example. One such method includes CDR grafting wherein CDRs from a non-human antibody are transferred to a human antibody scaffold. This method, however, may result in a reduction in binding to the target antigen, which may be a consequence of the imperfect fit between the antibody scaffold and the CDRs that results in a loss in molecular recognition between the antigen and the "antibody."

Some methods are used with the aim of preserving the surface recognition features of the antigen-antibody interface (Raghunathan, 2009). Rather than simply transferring a CDR amino acid sequence from one antigen binding molecule to replace a structural loop in another immunoglobulin scaffold, these methods take other characteristics of the antigen binding molecule being transferred into account to preserve the three dimensional orientation of the amino acids and their interactions with framework region amino acids. For example, when constructing a humanized antibody, human frameworks are selected based on sequence similarity of the non-human and human frameworks, length of the 3 "CDR" loops, and the sequence similarity of the loop residues.

The present invention features novel CH2 domain template molecules and methods of design of such CH2 domain templates wherein loops from a database of domains (the "donor loops") are transferred to a CH2 domain scaffold ("the acceptor"). The donor loops may be chosen based on length, for example the chosen donor loop may have a length that is similar (but not necessarily identical) to that of a structural loop in the CH2 domain scaffold. The CH2 domain scaffold may be derived from a CH2 domain of human IgG or from a CH2 domain of a different Ig or from a CH2 domain of a different mammal, e.g., macaque.

The CH2 domain has a traditional Ig-fold with a β sheet sandwich comprising 3 pairs of β strands. A disulfide bond connects the middle 13 strands. The strands are denoted by A, B, C, D, E, F and G. Intervening loops (sometimes called structural loops) are denoted as BC, DE and FG. As used herein, loops BC, DE and FG will be referred to as L1, L2 and L3 respectively. These three loops bind to the Fc-Gamma receptor when present as part of the Fc dimer. The other three loops, AB, CD and EF bind to the Fc-Rn receptor when present as part of the Fc dimer. While the CH2 domain scaffold is broadly similar to that of an Ig domain, there are variations both in the sequence signatures and structure. One distinct difference in structure is the D strand. This region is a typical beta strand in most Ig domains, but it is a coil in the CH2 domain. This structural difference in the D region may have entropic effects on the L2 loop. The transfer of loops to the CH2 domain can have an effect on the binding and stability of the engineered molecule. Thus, the present invention is different from traditional methods of antibody engineering involving loop grafting (e.g., traditional humanizing of antibodies) and transferring a loop to a variable domain. Referring to the loop transfer from donor molecules to the CH2 domain scaffolds of the present invention, it is difficult to predict what would be a good loop match based on the amino acid sequence of a loop in a typical immunoglobulin antigen binding region (e.g., since there are significant differences in the sequence patterns and structure). The transfer of loops from a donor to an acceptor molecule would affect the binding and stability of the molecule.

In the present invention at least one or up to three loops (e.g., L1, L2, L3, L1 and L2, L1 and L3, L2 and L3, or L1 and L2 and L3) from a donor are transferred to the CH2 domain. Without wishing to limit the present invention to any theory or mechanism, we believe that a careful rational transfer of such compatible structural loops from a selected donor may ensure preservation of the stereochemistry and surface topology of the antigen binding region of the donor molecule. Also, we believe that preservation of interactions among the loops and between the loops and the proximal β strands may lead to molecules that have desirable biophysical and biochemical properties (e.g., stability, solubility). While we believe that compatible loops may help to maintain affinity with the target, we believe variations in loop lengths may provide recognition with different types of antigens.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description.

SUMMARY

The present invention features novel CH2 domain template molecules and methods of design of such CH2 domain templates wherein loops from a database of domains (the "donor loops") are transferred to a CH2 domain scaffold ("the acceptor"). The donor loops may be chosen based on length, for example the chosen donor loop may have a length that is similar (but not necessarily identical) to that of a structural loop in the CH2 domain scaffold.

In some embodiments, the CH2 domain template molecule comprises a CH2 domain scaffold of IgG, IgA, IgD, or a CH3 domain scaffold of IgE, or IgM, having a L1 loop, a L2 loop, and a L3 loop, wherein the L1 loop is replaced with a donor L1 loop of a donor molecule, the donor molecule further comprising a donor L2 loop and a donor L3 loop, wherein the donor L2 loop of the donor molecule has a first length and the donor L3 loop of the donor molecule has a second length, the first length closely matching a length of the L2 loop of the CH2 domain scaffold and the second length closely matching a length of the L3 loop of the CH2 domain scaffold.

In some embodiments, the CH2 domain template molecule comprises a CH2 domain scaffold of IgG, IgA, IgD, or a CH3 domain scaffold of IgE, or IgM, having a L1 loop, a L2 loop, and a L3 loop, wherein the L2 loop is replaced with a donor L2 loop of a donor molecule, the donor molecule further comprising a donor L1 loop and a donor L3 loop, wherein the donor L1 loop of the donor molecule has a first length and the donor L3 loop of the donor molecule has a second length, the first length closely matching a length of the L1 loop of the CH2 domain scaffold and the second length closely matching a length of the L3 loop of the CH2 domain scaffold.

In some embodiments, the CH2 domain template molecule comprises a CH2 domain scaffold of IgG, IgA, IgD, or a CH3 domain scaffold of IgE, or IgM, having a L1 loop, a L2 loop, and a L3 loop, wherein the L3 loop is replaced with a donor L3 loop of a donor molecule, the donor molecule further comprising a donor L1 loop and a donor L2 loop, wherein the donor L1 loop of the donor molecule has a first length and the donor L2 loop of the donor molecule has a second length, the first length closely matching a length of the L1 loop of the CH2 domain scaffold and the second length closely matching a length of the L2 loop of the CH2 domain scaffold.

In some embodiments, the CH2 domain template molecule comprises a CH2 domain scaffold of IgG, IgA, IgD, or a CH3 domain scaffold of IgE, or IgM, having a L1 loop, a L2 loop, and a L3 loop, wherein the L1 loop and the L2 loop are replaced with either (i) a donor L1 loop and a donor L2 loop of a donor molecule, respectively, or (ii) the donor L2 loop and the donor L1 loop of the donor molecule, respectively, wherein the donor molecule further comprises a donor L3 loop having a first length, the first length closely matching a length of the L3 loop of the CH2 domain scaffold.

In some embodiments, the CH2 domain template molecule comprises a CH2 domain scaffold of IgG, IgA, IgD, or a CH3 domain scaffold of IgE, or IgM, having a L1 loop, a L2 loop, and a L3 loop, wherein the L1 loop and the L3 loop are replaced with either (i) a donor L1 loop and a donor L3 loop of a donor molecule, respectively, or (ii) the donor L3 loop and the donor L1 loop of the donor molecule, respectively; wherein the donor molecule further comprises a donor L2 loop having a first length, the first length closely matching a length of the L2 loop of the CH2 domain scaffold.

In some embodiments, the CH2 domain template molecule comprises a CH2 domain scaffold of IgG, IgA, IgD, or a CH3 domain scaffold of IgE, or IgM, having a L1 loop, a L2 loop, and a L3 loop, wherein the L2 loop and the L3 loop are replaced with either (i) a donor L2 loop and a donor L3 loop of a donor molecule, respectively, or (ii) the donor L3 loop and the donor L2 loop of the donor molecule, respectively; wherein the donor molecule further comprises a donor L1 loop having a first length, the first length closely matching a length of the L1 loop of the CH2 domain scaffold.

In some embodiments, the CH2 domain template molecule comprises a CH2 domain scaffold of IgG, IgA, IgD, or a CH3 domain scaffold of IgE, or IgM, having a L1 loop, a L2 loop, and a L3 loop, wherein the L1 loop, the L2 loop, and the L3 loop are replaced with any of (a) a donor L1 loop, a donor L2 loop, and a donor L3 loop of a donor molecule, respectively;

(b) a donor L1 loop, a donor L3 loop, and a donor L2 loop of a donor molecule, respectively; (c) a donor L2 loop, a donor L1 loop, and a donor L3 loop of a donor molecule, respectively; (d) a donor L2 loop, a donor L3 loop, and a donor L1 loop of a donor molecule, respectively; (e) a donor L3 loop, a donor L1 loop, and a donor L2 loop of a donor molecule, respectively; or (f) a donor L3 loop, a donor L2 loop, and a donor L1 loop of a donor molecule, respectively; the donor molecule comprising a donor L1 loop, a donor L2 loop, and a donor L3 loop.

In some embodiments, "closely matching" refers to an exact match or a length plus or minus one amino acid. In some embodiments, "closely matching" refers to an exact match, a length plus or minus one amino acid, a length plus or minus two amino acids, a length plus or minus three amino acids, or a length plus or minus four amino acids. In some embodiments, "closely matching" refers to an exact match, a length plus or minus one amino acid, a length plus or minus two amino acids, a length plus or minus three amino acids, a length plus or minus four amino acids, or a length plus or minus five or more amino acids.

In some embodiments, the length of the L2 loop of the CH2 domain scaffold is 6 amino acids. In some embodiments, the length of the L3 loop of the CH2 domain scaffold is 9 amino acids.

In some embodiments, the donor molecule is selected from a database of crystal structures of molecules, each molecule having a L1 loop, a L2 loop, and a L3 loop. In some embodiments, the donor molecule is selected from a database of crystal structures of Ig-like molecules, each molecule having a L1 loop, a L2 loop, and a L3 loop. In some embodiments, the donor molecule is selected from a database of crystal structures of V-like domains from Ig molecules, each molecule having a L1 loop, a L2 loop, and a L3 loop.

In some embodiments, the CH2 domain template comprises an antigen binding region or epitope.

In some embodiments, the CH2 domain template molecule has a molecular weight less than about 20 kDa.

In some embodiments, the CH2 domain template molecule has a melting temperature that is at least 40° C. In some embodiments, the CH2 domain template molecule has a melting temperature that is at least 50° C. In some embodiments, the CH2 domain template molecule has a melting temperature that is at least 60° C. In some embodiments, the CH2 domain template molecule has a melting temperature that is at least 65° C. In some embodiments, the CH2 domain template molecule has a melting temperature that is at least 70° C. In some embodiments, the CH2 domain template molecule has a melting temperature that is at least 80° C.

In some embodiments, the CH2 domain template molecule has an amino acid truncation. In some embodiments, the CH2 domain template molecule has an amino acid truncation at its N-terminus. In some embodiments, the CH2 domain template molecule has an amino acid truncation at its C-terminus. In some embodiments, the CH2 domain template molecule has an amino acid truncation at its N-terminus and at its C-terminus. In some embodiments, the amino acid truncation is a 1 amino acid truncation, a 2 amino acid truncation, a 3 amino acid truncation, a 4 amino acid truncation, a 5 amino acid truncation, 6 amino acid truncation, or a 7 amino acid truncation.

In some embodiments, the CH2 domain template molecule has an amino acid addition. In some embodiments, the CH2 domain template molecule has an amino acid addition at its N-terminus. In some embodiments, the CH2 domain template molecule has an amino acid addition at its C-terminus. In some embodiments, the CH2 domain template molecule has an amino acid addition at its N-terminus and at its C-terminus.

In some embodiments, the amino acid addition is a 1 amino acid addition, a 2 amino acid addition, a 3 amino acid addition, a 4 amino acid addition, a 5 amino acid addition, 6 amino acid addition, a 7 amino acid addition, an 8 amino acid addition, a nine amino acid addition, or a 10 amino acid addition.

In some embodiments, the CH2 domain template molecule comprises an additional disulfide bond created from a cysteine substitution at position 240 and at position 332. In some embodiments, the CH2 domain template molecule comprises an additional disulfide bond created from a cysteine substitution at position 239 and at position 332. In some embodiments, the CH2 domain template molecule comprises an additional disulfide bond created from a cysteine substitution at position 244 and at position 336. In some embodiments, the CH2 domain template molecule comprises an additional disulfide bond created from a cysteine substitution at position 293 and 301. In some embodiments, the CH2 domain template molecule comprises an additional disulfide bond created from a cysteine substitution at position 242 and 334. In some embodiments, the CH2 domain template molecule comprises an additional disulfide bond created from a cysteine substitution at position 240 and 334.

In some embodiments, the CH2 domain template molecule comprises both an amino acid truncation and an additional disulfide bond. In some embodiments, the CH2 domain template molecule comprises both an amino acid truncation at its N-terminus and an additional disulfide bond. In some embodiments, the CH2 domain template molecule comprises both an amino acid truncation at its C-terminus and an additional disulfide bond. In some embodiments, the CH2 domain template molecule comprises both an amino acid truncation at both its N-terminus and C-terminus and an additional disulfide bond.

In some embodiments, the CH2 domain template molecule comprises both an amino acid addition and an additional disulfide bond. In some embodiments, the CH2 domain template molecule comprises both an amino acid addition at its N-terminus and an additional disulfide bond. In some embodiments, the CH2 domain template molecule comprises both an amino acid addition at its C-terminus and an additional disulfide bond. In some embodiments, the CH2 domain template molecule comprises both an amino acid addition at both its N-terminus and C-terminus and an additional disulfide bond. In some embodiments, the CH2 domain template molecule comprises both an amino acid addition within the CH2 domain template molecule and an additional disulfide bond.

In some embodiments, the donor loop has an amino acid addition or deletion. In some embodiments, the donor L1 loop has between 5 to 24 amino acids.

In some embodiments, the CH2 domain template molecule is expressed in a bacterial system, a phage system, a yeast system, an insect system, or a mammalian system.

In some embodiments, the CH2 domain template molecule is linked to an immunoconjugate, toxin, immunotoxin, a drug, an isotope, or an imaging reagent.

In some embodiments, the CH2 domain template molecule comprises a leader sequence.

In some embodiments, the CH2 domain template molecule comprises an amino acid substitution. In some embodiments, the CH2 domain template molecule comprises an amino acid substitution, the amino acid substitution being M252Y, S254T, T256E, T307A, or a combination thereof.

In some embodiments, the CH2 domain template molecule retains binding to FcRn. In some embodiments, the CH2 domain template molecule comprises at least one functional FcRn binding site. In some embodiments, the CH2 domain template molecule comprises at least one functional FcRn binding site, the FcRn binding site being modified to enhance serum half life.

In some embodiments, the CH2 domain template molecule comprises at least one FcR binding site.

In some embodiments, the CH2 domain template molecule comprises a binding site able to bind complement. In some embodiments, the CH2 domain template molecule has reduced or absent activation of complement.

In some embodiments, the CH2 domain template molecule comprises a pharmaceutical carrier.

In some embodiments, the L2 loop and the L3 loop are replaced with a donor L2 loop and a donor L3 loop, respectively, or the L2 loop and the L3 loop are replaced with a donor L3 loop and a donor L2 loop, respectively. In some embodiments, the L1 loop and the L3 loop are replaced with a donor L1 loop and a donor L3 loop, respectively, or the L1 loop and the L3 loop are replaced with a donor L3 loop and a donor L1 loop, respectively. In some embodiments, the L1 loop and the L2 loop are replaced with a donor L1 loop and a donor L2 loop, respectively, or the L1 loop and the L2 loop are replaced with a donor L3 loop and a donor L2 loop, respectively. In some embodiments, the L3 loop is replaced with a donor L3 loop. In some embodiments, the L2 loop is replaced with a donor L2 loop. In some embodiments, the L1 loop is replaced with a donor L1 loop.

The present invention also features methods of generating CH2 domain template molecules. In some embodiments, the method comprises (a) providing a CH2 domain scaffold of IgG, IgA, IgD, or a CH3 domain scaffold of IgE, or IgM, having a L1 loop, a L2 loop, and a L3 loop; (b) providing a donor L1 loop from a donor molecule, the donor molecule further comprising a donor L2 loop and a donor L3 loop, wherein the donor L2 loop of the donor molecule has a first length and the donor L3 loop of the donor molecule has a second length, the first length closely matching a length of the L2 loop of the CH2 domain scaffold and the second length closely matching a length of the L3 loop of the CH2 domain scaffold; and (c) replacing the L1 loop of the CH2 domain scaffold with the donor L1 loop.

In some embodiments, the method comprises (a) providing a CH2 domain scaffold of IgG, IgA, IgD, or a CH3 domain scaffold of IgE, or IgM, having a L1 loop, a L2 loop, and a L3 loop; (b) providing a donor L2 loop from a donor molecule, the donor molecule further comprising a donor L1 loop and a donor L3 loop, wherein the donor L1 loop of the donor molecule has a first length and the donor L3 loop of the donor molecule has a second length, the first length closely matching a length of the L1 loop of the CH2 domain scaffold and the second length closely matching a length of the L3 loop of the CH2 domain scaffold; and (c) replacing the L2 loop of the CH2 domain scaffold with the donor L2 loop.

In some embodiments, the method comprises (a) providing a CH2 domain scaffold of IgG, IgA, IgD, or a CH3 domain scaffold of IgE, or IgM, having a L1 loop, a L2 loop, and a L3 loop; (b) providing a donor L3 loop from a donor molecule, the donor molecule further comprising a donor L1 loop and a donor L2 loop, wherein the donor L1 loop of the donor molecule has a first length and the donor L2 loop of the donor molecule has a second length, the first length closely matching a length of the L1 loop of the CH2 domain scaffold and the second length closely matching a length of the L2 loop of the CH2 domain scaffold; and (c) replacing the L3 loop of the CH2 domain scaffold with the donor L3 loop.

In some embodiments, the method comprises (a) providing a CH2 domain scaffold of IgG, IgA, IgD, or a CH3 domain scaffold of IgE, or IgM, having a L1 loop, a L2 loop, and a L3 loop; (b) providing a donor L1 loop and a donor L2 loop from a donor molecule, the donor molecule further comprising a donor L3 loop having a first length, the first length closely matching a length of the L3 loop of the CH2 domain scaffold; and (c) either (i) replacing the L1 loop of the CH2 domain scaffold with the donor L1 loop and replacing the L2 loop of the CH2 domain scaffold with the donor L2 loop; or (ii) replacing the L1 loop of the CH2 domain scaffold with the donor L2 loop and replacing the L2 loop of the CH2 domain scaffold with the donor L1 loop.

In some embodiments, the method comprises (a) providing a CH2 domain scaffold of IgG, IgA, IgD, or a CH3 domain scaffold of IgE, or IgM, having a L1 loop, a L2 loop, and a L3 loop; (b) providing a donor L1 loop and a donor L3 loop from a donor molecule, the donor molecule further comprising a donor L2 loop having a first length, the first length closely matching a length of the L2 loop of the CH2 domain scaffold; and (c) either (i) replacing the L1 loop of the CH2 domain scaffold with the donor L1 loop and replacing the L3 loop of the CH2 domain scaffold with the donor L3 loop; or (ii) replacing the L1 loop of the CH2 domain scaffold with the donor L3 loop and replacing the L3 loop of the CH2 domain scaffold with the donor L1 loop.

In some embodiments, the method comprises (a) providing a CH2 domain scaffold of IgG, IgA, IgD, or a CH3 domain scaffold of IgE, or IgM, having a L1 loop, a L2 loop, and a L3 loop; (b) providing a donor L2 loop and a donor L3 loop from a donor molecule, the donor molecule further comprising a donor L1 loop having a first length, the first length closely matching a length of the L1 loop of the CH2 domain scaffold; and (c) either (i) replacing the L2 loop of the CH2 domain scaffold with the donor L2 loop and replacing the L3 loop of the CH2 domain scaffold with the donor L3 loop; or (ii) replacing the L2 loop of the CH2 domain scaffold with the donor L3 loop and replacing the L3 loop of the CH2 domain scaffold with the donor L2 loop.

In some embodiments, the method further comprises replacing the L2 loop and the L3 loop with a donor L2 loop and a donor L3 loop respectively, or replacing the L2 loop and the L3 loop with a donor L3 loop and a donor L2 loop, respectively. In some embodiments, the method further comprises replacing the L1 loop and the L3 loop with a donor L1 loop and a donor L3 loop respectively, or replacing the L1 loop and the L3 loop with a donor L3 loop and a donor L1 loop, respectively. In some embodiments, the method further comprises replacing the L1 loop and the L2 loop with a donor L1 loop and a donor L2 loop respectively, or replacing the L1 loop and the L2 loop with a donor L2 loop and a donor L1 loop, respectively. In some embodiments, the method further comprises replacing the L3 loop with a donor L3 loop. In some embodiments, the method further comprises replacing the L2 loop with a donor L2 loop. In some embodiments, the method further comprises replacing the L1 loop with a donor L1 loop.

In some embodiments, the CH2 domain template molecule is displayed on a surface of any cell, phage, vector, or displayed in vitro. In some embodiments, the CH2 domain template molecule is expressed in a bacterial system, a cis display system, a yeast system, a phage display system, or a ribosomal display system.

The present invention also features CH2 domain template molecules generated from methods comprising (a) providing a CH2 domain scaffold of IgG, IgA, IgD, or a CH3 domain scaffold of IgE, or IgM, having a L1 loop, a L2 loop, and a L3 loop; (b) providing a donor L1 loop from a donor molecule, the donor molecule further comprising a donor L2 loop and a donor L3 loop, wherein the donor L2 loop of the donor molecule has a first length and the donor L3 loop of the donor molecule has a second length, the first length closely matching a length of the L2 loop of the CH2 domain scaffold and the second length closely matching a length of the L3 loop of the CH2 domain scaffold; and (c) replacing the L1 loop of the CH2 domain scaffold with the donor L1 loop.

The present invention also features CH2 domain template molecules generated from methods comprising (a) providing a CH2 domain scaffold of IgG, IgA, IgD, or a CH3 domain scaffold of IgE, or IgM, having a L1 loop, a L2 loop, and a L3 loop; (b) providing a donor L2 loop from a donor molecule, the donor molecule further comprising a donor L1 loop and a donor L3 loop, wherein the donor L1 loop of the donor molecule has a first length and the donor L3 loop of the donor molecule has a second length, the first length closely matching a length of the L1 loop of the CH2 domain scaffold and the second length closely matching a length of the L3 loop of the CH2 domain scaffold; and (c) replacing the L2 loop of the CH2 domain scaffold with the donor L2 loop.

The present invention also features CH2 domain template molecules generated from methods comprising (a) providing a CH2 domain scaffold of IgG, IgA, IgD, or a CH3 domain scaffold of IgE, or IgM, having a L1 loop, a L2 loop, and a L3 loop; (b) providing a donor L3 loop from a donor molecule, the donor molecule further comprising a donor L1 loop and a donor L2 loop, wherein the donor L1 loop of the donor molecule has a first length and the donor L2 loop of the donor molecule has a second length, the first length closely matching a length of the L1 loop of the CH2 domain scaffold and the second length closely matching a length of the L2 loop of the CH2 domain scaffold; and (c) replacing the L3 loop of the CH2 domain scaffold with the donor L3 loop.

The present invention also features CH2 domain template molecules generated from methods comprising (a) providing a CH2 domain scaffold of IgG, IgA, IgD, or a CH3 domain scaffold of IgE, or IgM, having a L1 loop, a L2 loop, and a L3 loop; (b) providing a donor L1 loop and a donor L2 loop from a donor molecule, the donor molecule further comprising a donor L3 loop having a first length, the first length closely matching a length of the L3 loop of the CH2 domain scaffold; and (c) either (i) replacing the L1 loop of the CH2 domain scaffold with the donor L1 loop and replacing the L2 loop of the CH2 domain scaffold with the donor L2 loop; or (ii) replacing the L1 loop of the CH2 domain scaffold with the donor L2 loop and replacing the L2 loop of the CH2 domain scaffold with the donor L1 loop.

The present invention also features CH2 domain template molecules generated from methods comprising (a) providing a CH2 domain scaffold of IgG, IgA, IgD, or a CH3 domain scaffold of IgE, or IgM, having a L1 loop, a L2 loop, and a L3 loop; (b) providing a donor L1 loop and a donor L3 loop from a donor molecule, the donor molecule further comprising a donor L2 loop having a first length, the first length closely matching a length of the L2 loop of the CH2 domain scaffold; and (c) either (i) replacing the L1 loop of the CH2 domain scaffold with the donor L1 loop and replacing the L3 loop of the CH2 domain scaffold with the donor L3 loop; or (ii) replacing the L1 loop of the CH2 domain scaffold with the donor L3 loop and replacing the L3 loop of the CH2 domain scaffold with the donor L1 loop.

The present invention also features CH2 domain template molecules generated from methods comprising (a) providing a CH2 domain scaffold of IgG, IgA, IgD, or a CH3 domain scaffold of IgE, or IgM, having a L1 loop, a L2 loop, and a L3 loop; (b) providing a donor L2 loop and a donor L3 loop from a donor molecule, the donor molecule further comprising a donor L1 loop having a first length, the first length closely matching a length of the L1 loop of the CH2 domain scaffold; and (c) either (i) replacing the L2 loop of the CH2 domain scaffold with the donor L2 loop and replacing the L3 loop of the CH2 domain scaffold with the donor L3 loop; or (ii) replacing the L2 loop of the CH2 domain scaffold with the donor L3 loop and replacing the L3 loop of the CH2 domain scaffold with the donor L2 loop.

The present invention also features multimeric CH2 proteins. In some embodiments, the multimeric CH2 protein comprises a first portion and a second portion, the first portion and the second portion being either: (i) a CH2 domain scaffold of IgG, IgA, IgD, or a CH3 domain scaffold of IgE, or IgM, having a L1 loop, a L2 loop, and a L3 loop, wherein the L1 loop is replaced with a donor L1 loop of a donor molecule, the donor molecule further comprising a donor L2 loop and a donor L3 loop, wherein the donor L2 loop of the donor molecule has a first length and the donor L3 loop of the donor molecule has a second length, the first length closely matching a length of the L2 loop of the CH2 domain scaffold and the second length closely matching a length of the L3 loop of the CH2 domain scaffold; (ii) a CH2 domain scaffold of IgG, IgA, IgD, or a CH3 domain scaffold of IgE, or IgM, having a L1 loop, a L2 loop, and a L3 loop, wherein the L2 loop is replaced with a donor L2 loop of a donor molecule, the donor molecule further comprising a donor L1 loop and a donor L3 loop, wherein the donor L1 loop of the donor molecule has a first length and the donor L3 loop of the donor molecule has a second length, the first length closely matching a length of the L1 loop of the CH2 domain scaffold and the second length closely matching a length of the L3 loop of the CH2 domain scaffold; (iii) a CH2 domain scaffold of IgG, IgA, IgD, or a CH3 domain scaffold of IgE, or IgM, having a L1 loop, a L2 loop, and a L3 loop, wherein the L3 loop is replaced with a donor L3 loop of a donor molecule, the donor molecule further comprising a donor L1 loop and a donor L2 loop, wherein the donor L1 loop of the donor molecule has a first length and the donor L2 loop of the donor molecule has a second length, the first length closely matching a length of the L1 loop of the CH2 domain scaffold and the second length closely matching a length of the L2 loop of the CH2 domain scaffold; (iv) a CH2 domain scaffold of IgG, IgA, IgD, or a CH3 domain scaffold of IgE, or IgM, having a L1 loop, a L2 loop, and a L3 loop, wherein the L1 loop and the L2 loop are replaced with either (a) a donor L1 loop and a donor L2 loop of a donor molecule, respectively, or (b) the donor L2 loop and the donor L1 loop of the donor molecule, respectively, wherein the donor molecule further comprises a donor L3 loop having a first length, the first length closely matching a length of the L3 loop of the CH2 domain scaffold; (v) a CH2 domain scaffold of IgG, IgA, IgD, or a CH3 domain scaffold of IgE, or IgM, having a L1 loop, a L2 loop, and a L3 loop, wherein the L1 loop and the L3 loop are replaced with either (a) a donor L1 loop and a donor L3 loop of a donor molecule, respectively, or (b) the donor L3 loop and the donor L1 loop of the donor molecule, respectively, wherein the donor molecule further comprises a donor L2 loop having a first length, the first length closely matching a length of the L2 loop of the CH2 domain scaffold; (vi) a CH2 domain scaffold of IgG, IgA, IgD, or a CH3 domain scaffold of IgE, or IgM, having a L1 loop, a L2 loop, and a L3 loop, wherein the L2 loop and the L3 loop are replaced with either (a) a donor L2 loop and a donor L3 loop of a donor molecule, respectively, or (b) the donor L3 loop and the donor L2 loop of the donor molecule, respectively, wherein the donor molecule further comprises a donor L1 loop having a first length, the first length closely matching a length of the L1 loop of the CH2 domain scaffold;

or (vii) a CH2 domain scaffold of IgG, IgA, IgD, or a CH3 domain scaffold of IgE, or IgM, having a L1 loop, a L2 loop, and a L3 loop, wherein the L1 loop, the L2 loop, and the L3 loop are replaced with any of (a) a donor L1 loop, a donor L2 loop, and a donor L3 loop of a donor molecule, respectively; (b) a donor L1 loop, a donor L3 loop, and a donor L2 loop of a donor molecule, respectively; (c) a donor L2 loop, a donor L1 loop, and a donor L3 loop of a donor molecule, respectively; (d) a donor L2 loop, a donor L3 loop, and a donor L1 loop of a donor molecule, respectively; (e) a donor L3 loop, a donor L1 loop, and a donor L2 loop of a donor molecule, respectively; or (f) a donor L3 loop, a donor L2 loop, and a donor L1 loop of a donor molecule, respectively; the donor molecule comprising a donor L1 loop, a donor L2 loop, and a donor L3 loop.

The present invention also features a library of CH2 domain template molecules. In some embodiments, each CH2 domain template molecule comprises either: (i) a CH2 domain scaffold of IgG, IgA, IgD, or a CH3 domain scaffold of IgE, or IgM, having a L1 loop, a L2 loop, and a L3 loop, wherein the L1 loop is replaced with a donor L1 loop of a donor molecule, the donor molecule further comprising a donor L2 loop and a donor L3 loop, wherein the donor L2 loop of the donor molecule has a first length and the donor L3 loop of the donor molecule has a second length, the first length closely matching a length of the L2 loop of the CH2 domain scaffold and the second length closely matching a length of the L3 loop of the CH2 domain scaffold; (ii) a CH2 domain scaffold of IgG, IgA, IgD, or a CH3 domain scaffold of IgE, or IgM, having a L1 loop, a L2 loop, and a L3 loop, wherein the L2 loop is replaced with a donor L2 loop of a donor molecule, the donor molecule further comprising a donor L1 loop and a donor L3 loop, wherein the donor L1 loop of the donor molecule has a first length and the donor L3 loop of the donor molecule has a second length, the first length closely matching a length of the L1 loop of the CH2 domain scaffold and the second length closely matching a length of the L3 loop of the CH2 domain scaffold; (iii) a CH2 domain scaffold of IgG, IgA, IgD, or a CH3 domain scaffold of IgE, or IgM, having a L1 loop, a L2 loop, and a L3 loop, wherein the L3 loop is replaced with a donor L3 loop of a donor molecule, the donor molecule further comprising a donor L1 loop and a donor L2 loop, wherein the donor L1 loop of the donor molecule has a first length and the donor L2 loop of the donor molecule has a second length, the first length closely matching a length of the L1 loop of the CH2 domain scaffold and the second length closely matching a length of the L2 loop of the CH2 domain scaffold; (iv) a CH2 domain scaffold of IgG, IgA, IgD, or a CH3 domain scaffold of IgE, or IgM, having a L1 loop, a L2 loop, and a L3 loop, wherein the L1 loop and the L2 loop are replaced with either (a) a donor L1 loop and a donor L2 loop of a donor molecule, respectively, or (b) the donor L2 loop and the donor L1 loop of the donor molecule, respectively, wherein the donor molecule further comprises a donor L3 loop having a first length, the first length closely matching a length of the L3 loop of the CH2 domain scaffold; (v) a CH2 domain scaffold of IgG, IgA, IgD, or a CH3 domain scaffold of IgE, or IgM, having a L1 loop, a L2 loop, and a L3 loop, wherein the L1 loop and the L3 loop are replaced with either (a) a donor L1 loop and a donor L3 loop of a donor molecule, respectively, or (b) the donor L3 loop and the donor L1 loop of the donor molecule, respectively, wherein the donor molecule further comprises a donor L2 loop having a first length, the first length closely matching a length of the L2 loop of the CH2 domain scaffold; (vi) a CH2 domain scaffold of IgG, IgA, IgD, or a CH3 domain scaffold of IgE, or IgM, having a L1 loop, a L2 loop, and a L3 loop, wherein the L2 loop and the L3 loop are replaced with either (a) a donor L2 loop and a donor L3 loop of a donor molecule, respectively, or (b) the donor L3 loop and the donor L2 loop of the donor molecule, respectively, wherein the donor molecule further comprises a donor L1 loop having a first length, the first length closely matching a length of the L1 loop of the CH2 domain scaffold; or (vii) a CH2 domain scaffold of IgG, IgA, IgD, or a CH3 domain scaffold of IgE, or IgM, having a L1 loop, a L2 loop, and a L3 loop, wherein the L1 loop, the L2 loop, and the L3 loop are replaced with any of (a) a donor L1 loop, a donor L2 loop, and a donor L3 loop of a donor molecule, respectively; (b) a donor L1 loop, a donor L3 loop, and a donor L2 loop of a donor molecule, respectively; (c) a donor L2 loop, a donor L1 loop, and a donor L3 loop of a donor molecule, respectively; (d) a donor L2 loop, a donor L3 loop, and a donor L1 loop of a donor molecule, respectively; (e) a donor L3 loop, a donor L1 loop, and a donor L2 loop of a donor molecule, respectively; or (f) a donor L3 loop, a donor L2 loop, and a donor L1 loop of a donor molecule, respectively; the donor molecule comprising a donor L1 loop, a donor L2 loop, and a donor L3 loop.

In some embodiments, the library may comprise variant molecules derived from any individual CH2D template of the CH2D templates as described herein, wherein the library has members with at least one amino acid change (substituted, deleted or inserted) compared with the starting CH2D template.

In some embodiments, the library is derived from random mutagenesis of the CH2D template. In some embodiments, the library is designed and synthesized to contain all 20 natural amino acids at any point of substitution or insertion. In some embodiments, the library is designed to have fewer than all 20 natural amino acids at each position of variation.

The present invention also features DNA sequences (e.g., isolated DNA sequences) encoding the members of the library.

The present invention also features a method of constructing a library. In some embodiments, the method comprises (a) providing a DNA construct having a sequence corresponding to a CH2 domain scaffold of IgG, IgA, IgD, or a CH3 domain scaffold of IgE, or IgM, having a L1 loop, a L2 loop, and a L3 loop; and (b) any of: (i) replacing a sequence corresponding to the L1 loop of the scaffold with a sequence corresponding to a donor L1 loop of a donor molecule, the donor molecule further comprising a donor L2 loop and a donor L3 loop, wherein the donor L2 loop of the donor molecule has a first amino acid length and the donor L3 loop of the donor molecule has a second amino acid length, the first amino acid length closely matching an amino acid length of the L2 loop of the scaffold and the second length closely matching an amino acid length of the L3 loop of the scaffold; (ii) replacing a sequence corresponding to the L2 loop of the scaffold with a sequence corresponding to a donor L2 loop of a donor molecule, the donor molecule further comprising a donor L1 loop and a donor L3 loop, wherein the donor L1 loop of the donor molecule has a first length and the donor L3 loop of the donor molecule has a second length, the first length closely matching a length of the L1 loop of the scaffold and the second length closely matching a length of the L3 loop of the scaffold; (iii) replacing a sequence corresponding to the L3 loop of the scaffold with a sequence corresponding to a donor L3 loop of a donor molecule, the donor molecule further comprising a donor L1 loop and a donor L2 loop, wherein the donor L1 loop of the donor molecule has a first length and the donor L2 loop of the donor molecule has a second length, the first length closely matching a length of the L1 loop of the scaffold and the second length closely matching a length of the L2 loop of the scaffold; (iv) replacing a sequence corresponding to the L1 loop and a sequence corresponding to the L2 loop of the scaffold with either (a) a sequence corresponding to a donor L1 loop and a sequence corresponding to a donor L2 loop of a donor molecule, respectively, or (b) a sequence corresponding to a donor L2 loop and a sequence corresponding to a donor L2 loop of a donor molecule, respectively, wherein the donor molecule further comprises a donor L3 loop having a first length, the first length closely matching a length of the L3 loop of the scaffold; (v) replacing a sequence corresponding to the L1 loop and a sequence corresponding to the L3 loop of the scaffold with either (a) a sequence corresponding to a donor L1 loop and a sequence corresponding to a donor L3 loop of a donor molecule, respectively, or (b) a sequence corresponding to a donor L3 loop and a sequence corresponding to a donor L1 loop of a donor molecule, respectively, wherein the donor molecule further comprises a donor L2 loop having a first length, the first length closely matching a length of the L2 loop of the scaffold; (vi) replacing a sequence corresponding to the L2 loop and a sequence corresponding to the L3 loop of the scaffold with either (a) a sequence corresponding to a donor L2 loop and a sequence corresponding to a donor L3 loop of a donor molecule, respectively, or (b) a sequence corresponding to a donor L3 loop and a sequence corresponding to a donor L2 loop of a donor molecule, respectively, wherein the donor molecule further comprises a donor L1 loop having a first length, the first length closely matching a length of the L1 loop of the scaffold; or (vii) replacing a sequence corresponding to the L1 loop, a sequence corresponding to the L2 loop, and a sequence corresponding to the L3 loop of the scaffold with either (a) a sequence corresponding to a donor L1 loop, a sequence corresponding to a donor L2 loop, and a sequence corresponding to a donor L3 loop, respectively; (b) a sequence corresponding to a donor L1 loop, a sequence corresponding to a donor L3 loop, and a sequence corresponding to a donor L2 loop, respectively; (c) a sequence corresponding to a donor L2 loop, a sequence corresponding to a donor L1 loop, and a sequence corresponding to a donor L3 loop, respectively; (d) a sequence corresponding to a donor L2 loop, a sequence corresponding to a donor L3 loop, and a sequence corresponding to a donor L1 loop, respectively; (e) a sequence corresponding to a donor L3 loop, a sequence corresponding to a donor L1 loop, and a sequence corresponding to a donor L2 loop, respectively; or (f) a sequence corresponding to a donor L3 loop, a sequence corresponding to a donor L2 loop, and a sequence corresponding to a donor L1 loop, respectively. In some embodiments, the library design will include altering the amino acid sequence of the new loop(s) to provide a variety of different amino acids at all or a few of the positions in the loop. Some positions, such as ligand contact residue or specificity determining residues, may not be altered in the design. In some embodiments, the method further comprises repeating steps (a) and (b) to create a library of CH2 domain template molecules.

The present invention also features a method of identifying a CH2 domain template molecule that specifically binds a target. In some embodiments, the method comprises: (a) providing a library of particles displaying on their surface a CH2 domain template molecule comprising either: (i) a CH2 domain scaffold of IgG, IgA, IgD, or a CH3 domain scaffold of IgE, or IgM, having a L1 loop, a L2 loop, and a L3 loop, wherein the L1 loop is replaced with a donor L1 loop of a donor molecule, the donor molecule further comprising a donor L2 loop and a donor L3 loop, wherein the donor L2 loop of the donor molecule has a first length and the donor L3 loop of the donor molecule has a second length, the first length closely matching a length of the L2 loop of the CH2 domain scaffold and the second length closely matching a length of the L3 loop of the CH2 domain scaffold; (ii) a CH2 domain scaffold of IgG, IgA, IgD, or a CH3 domain scaffold of IgE, or IgM, having a L1 loop, a L2 loop, and a L3 loop, wherein the L2 loop is replaced with a donor L2 loop of a donor molecule, the donor molecule further comprising a donor L1 loop and a donor L3 loop, wherein the donor L1 loop of the donor molecule has a first length and the donor L3 loop of the donor molecule has a second length, the first length closely matching a length of the L1 loop of the CH2 domain scaffold and the second length closely matching a length of the L3 loop of the CH2 domain scaffold; (iii) a CH2 domain scaffold of IgG, IgA, IgD, or a CH3 domain scaffold of IgE, or IgM, having a L1 loop, a L2 loop, and a L3 loop, wherein the L3 loop is replaced with a donor L3 loop of a donor molecule, the donor molecule further comprising a donor L1 loop and a donor L2 loop, wherein the donor L1 loop of the donor molecule has a first length and the donor L2 loop of the donor molecule has a second length, the first length closely matching a length of the L1 loop of the CH2 domain scaffold and the second length closely matching a length of the L2 loop of the CH2 domain scaffold; (iv) a CH2 domain scaffold of IgG, IgA, IgD, or a CH3 domain scaffold of IgE, or IgM, having a L1 loop, a L2 loop, and a L3 loop, wherein the L1 loop and the L2 loop are replaced with either (a) a donor L1 loop and a donor L2 loop of a donor molecule, respectively, or (b) the donor L2 loop and the donor L1 loop of the donor molecule, respectively, wherein the donor molecule further comprises a donor L3 loop having a first length, the first length closely matching a length of the L3 loop of the CH2 domain scaffold; (v) a CH2 domain scaffold of IgG, IgA, IgD, or a CH3 domain scaffold of IgE, or IgM, having a L1 loop, a L2 loop, and a L3 loop, wherein the L1 loop and the L3 loop are replaced with either (a) a donor L1 loop and a donor L3 loop of a donor molecule, respectively, or (b) the donor L3 loop and the donor L1 loop of the donor molecule, respectively, wherein the donor molecule further comprises a donor L2 loop having a first length, the first length closely matching a length of the L2 loop of the CH2 domain scaffold; (vi) a CH2 domain scaffold of IgG, IgA, IgD, or a CH3 domain scaffold of IgE, or IgM, having a L1 loop, a L2 loop, and a L3 loop, wherein the L2 loop and the L3 loop are replaced with either (a) a donor L2 loop and a donor L3 loop of a donor molecule, respectively, or (b) the donor L3 loop and the donor L2 loop of the donor molecule, respectively, wherein the donor molecule further comprises a donor L1 loop having a first length, the first length closely matching a length of the L1 loop of the CH2 domain scaffold; or (vii) a CH2 domain scaffold of IgG, IgA, IgD, or a CH3 domain scaffold of IgE, or IgM, having a L1 loop, a L2 loop, and a L3 loop, wherein the L1 loop, the L2 loop, and the L3 loop are replaced with any of (a) a donor L1 loop, a donor L2 loop, and a donor L3 loop of a donor molecule, respectively; (b) a donor L1 loop, a donor L3 loop, and a donor L2 loop of a donor molecule, respectively; (c) a donor L2 loop, a donor L1 loop, and a donor L3 loop of a donor molecule, respectively; (d) a donor L2 loop, a donor L3 loop, and a donor L1 loop of a donor molecule, respectively; (e) a donor L3 loop, a donor L1 loop, and a donor L2 loop of a donor molecule, respectively; or (f) a donor L3 loop, a donor L2 loop, and a donor L1 loop of a donor molecule, respectively; the donor molecule comprising a donor L1 loop, a donor L2 loop, and a donor L3 loop; (b) introducing the target to the library of particles; and (c) selecting particles from the library that specifically bind to the target.

In some embodiments, the particles that display on their surface the CH2 domain template molecule include cells, particles, or molecules. In some embodiments, the particles include phage, DNA, and ribosomes.

The present invention also features a CH2 domain template molecule comprising a first CH2 domain scaffold of IgG, IgA, IgD, or a first CH3 domain scaffold of IgE, or IgM, having a L1 loop [BC], a L2 loop [DE], and a L3 loop [FG], wherein the CH2 domain template molecule comprises an additional disulfide bond.

In some embodiments, the CH2 domain template molecule comprises a second CH2 domain scaffold of IgG, IgA, IgD, or a second CH3 domain scaffold of IgE or IgM, having a L1 loop, a L2 loop, and a L3 loop, wherein the second CH2 domain scaffold or second CH3 domain scaffold comprises an additional disulfide bond.

In some embodiments, the additional disulfide bond is created from a cysteine substitution at position 240 and at position 332. In some embodiments, the additional disulfide bond is created from a cysteine substitution at position 239 and at position 332. In some embodiments, the additional disulfide bond is created from a cysteine substitution at position 244 and at position 336. In some embodiments, the additional disulfide bond is created from a cysteine substitution at position 293 and 301.

In some embodiments, the first CH2 domain scaffold or the first CH3 domain scaffold and the second CH2 domain or the second CH3 domain scaffold are linked by a linker.

The present invention also features an isolated nucleic acid sequence. In some embodiments, the isolated nucleic acid sequence encodes: a CH2 domain template molecule comprising a CH2 domain scaffold of IgG, IgA, IgD, or a CH3 domain scaffold of IgE, or IgM, having a L1 loop, a L2 loop, and a L3 loop, wherein the L1 loop is replaced with a donor L1 loop of a donor molecule, the donor molecule further comprising a donor L2 loop and a donor L3 loop, wherein the donor L2 loop of the donor molecule has a first length and the donor L3 loop of the donor molecule has a second length, the first length closely matching a length of the L2 loop of the CH2 domain scaffold and the second length closely matching a length of the L3 loop of the CH2 domain scaffold.

In some embodiments, the isolated nucleic acid sequence encodes: a CH2 domain template molecule comprising a CH2 domain scaffold of IgG, IgA, IgD, or a CH3 domain scaffold of IgE, or IgM, having a L1 loop, a L2 loop, and a L3 loop, wherein the L2 loop is replaced with a donor L2 loop of a donor molecule, the donor molecule further comprising a donor L1 loop and a donor L3 loop, wherein the donor L1 loop of the donor molecule has a first length and the donor L3 loop of the donor molecule has a second length, the first length closely matching a length of the L1 loop of the CH2 domain scaffold and the second length closely matching a length of the L3 loop of the CH2 domain scaffold.

In some embodiments, the isolated nucleic acid sequence encodes: a CH2 domain template molecule comprising a CH2 domain scaffold of IgG, IgA, IgD, or a CH3 domain scaffold of IgE, or IgM, having a L1 loop, a L2 loop, and a L3 loop; wherein the L3 loop is replaced with a donor L3 loop of a donor molecule, the donor molecule further comprising a donor L1 loop and a donor L2 loop, wherein the donor L1 loop of the donor molecule has a first length and the donor L2 loop of the donor molecule has a second length, the first length closely matching a length of the L1 loop of the CH2 domain scaffold and the second length closely matching a length of the L2 loop of the CH2 domain scaffold.

In some embodiments, the isolated nucleic acid sequence encodes: a CH2 domain template molecule comprising a CH2 domain scaffold of IgG, IgA, IgD, or a CH3 domain scaffold of IgE, or IgM, having a L1 loop, a L2 loop, and a L3 loop, wherein the L1 loop and the L2 loop are replaced with either (i) a donor L1 loop and a donor L2 loop of a donor molecule, respectively, or (ii) the donor L2 loop and the donor L1 loop of the donor molecule, respectively, wherein the donor molecule further comprises a donor L3 loop having a first length, the first length closely matching a length of the L3 loop of the CH2 domain scaffold.

In some embodiments, the isolated nucleic acid sequence encodes: a CH2 domain template molecule comprising a CH2 domain scaffold of IgG, IgA, IgD, or a CH3 domain scaffold of IgE, or IgM, having a L1 loop, a L2 loop, and a L3 loop, wherein the L1 loop and the L3 loop are replaced with either (i) a donor L1 loop and a donor L3 loop of a donor molecule, respectively, or (ii) the donor L3 loop and the donor L1 loop of the donor molecule, respectively; wherein the donor molecule further comprises a donor L2 loop having a first length, the first length closely matching a length of the L2 loop of the CH2 domain scaffold.

In some embodiments, the isolated nucleic acid sequence encodes: a CH2 domain template molecule comprising a CH2 domain scaffold of IgG, IgA, IgD, or a CH3 domain scaffold of IgE, or IgM, having a L1 loop, a L2 loop, and a L3 loop; wherein the L2 loop and the L3 loop are replaced with either (i) a donor L2 loop and a donor L3 loop of a donor molecule, respectively, or (ii) the donor L3 loop and the donor L2 loop of the donor molecule, respectively; wherein the donor molecule further comprises a donor L1 loop having a first length, the first length closely matching a length of the L1 loop of the scaffold.

In some embodiments, the isolated nucleic acid sequence encodes: a CH2 domain template molecule comprising a CH2 domain scaffold of IgG, IgA, IgD, or a CH3 domain scaffold of IgE, or IgM, having a L1 loop, a L2 loop, and a L3 loop, wherein the L1 loop, the L2 loop, and the L3 loop are replaced with any of (a) a donor L1 loop, a donor L2 loop, and a donor L3 loop of a donor molecule, respectively; (b) a donor L1 loop, a donor L3 loop, and a donor L2 loop of a donor molecule, respectively; (c) a donor L2 loop, a donor L1 loop, and a donor L3 loop of a donor molecule, respectively; (d) a donor L2 loop, a donor L3 loop, and a donor L1 loop of a donor molecule, respectively; (e) a donor L3 loop, a donor L1 loop, and a donor L2 loop of a donor molecule, respectively; or (f) a donor L3 loop, a donor L2 loop, and a donor L1 loop of a donor molecule, respectively; the donor molecule comprising a donor L1 loop, a donor L2 loop, and a donor L3 loop.

In some embodiments, a vector comprises the isolated nucleic acid sequence. In some embodiments, an isolated host cell comprises the vector.

DEFINITIONS

In order to facilitate the review of the various embodiments of the invention, the following explanations of specific terms are provided:

Definitions of common terms in molecular biology, cell biology, and immunology may be found in *Kuby Immunology*, Thomas J. Kindt, Richard A. Goldsby, Barbara Anne Osborne, Janis Kuby, published by W.H. Freeman, 2007 (ISBN 1429202114); and *Genes IX*, Benjamin Lewin, published by Jones & Bartlett Publishers, 2007 (ISBN-10: 0763740632).

Antibody: A protein (or complex) that includes one or more polypeptides substantially encoded by immunoglobulin genes or fragments of immunoglobulin genes. The immunoglobulin genes may include the kappa, lambda, alpha, gamma, delta, epsilon, and mu constant region genes, as well as the myriad of immunoglobulin variable region genes. Light chains may be classified as either kappa or lambda. Heavy chains may be classified as gamma, mu, alpha, delta, or epsilon, which in turn define the immunoglobulin classes IgG, IgM, IgA, IgD, and IgE, respectively.

As used herein, the term "antibodies" includes intact immunoglobulins as well as fragments (e.g., having a molecular weight between about 10 kDa to 100 kDa). Antibody fragments may include: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with the enzyme pepsin, followed by reduction, to yield an intact light chain and a portion of the heavy chain; two Fab' fragments are obtained per antibody molecule; (3) (Fab')2, the fragment of the antibody obtained by treating whole antibody with the enzyme pepsin without subsequent reduction; (4) F(ab')2, a dimer of two Fab' fragments held together by two disulfide bonds; (5) Fv, a genetically engineered fragment containing the variable region of the light chain and the variable region of the heavy chain expressed as two chains; and (6) scFv, single chain antibody, a genetically engineered molecule containing the variable region of the light chain, the variable region of the heavy chain, linked by a suitable polypeptide linker as a genetically fused single chain molecule. Methods of making antibody fragments are routine (see, for example, Harlow and Lane, *Using Antibodies: A Laboratory Manual*, CSHL, New York, 1999).

Antibodies can be monoclonal or polyclonal. Merely by way of example, monoclonal antibodies can be prepared from murine hybridomas according to classical methods such as Kohler and Milstein (*Nature* 256:495-97, 1975) or derivative methods thereof. Examples of detailed procedures for monoclonal antibody production are described in Harlow and Lane, *Using Antibodies: A Laboratory Manual*, CSHL, New York, 1999.

A standard "humanized" immunoglobulin, such as a humanized antibody, is an immunoglobulin including a human framework region and one or more CDRs from a non-human (e.g., mouse, rat, synthetic, etc.) immunoglobulin. A humanized antibody binds to the same or similar antigen as the donor antibody that provides the CDRs. The molecules can be constructed by means of genetic engineering (see, for example, U.S. Pat. No. 5,585,089).

Antigen: A compound, composition, or substance that can stimulate the production of antibodies or a T-cell response, including compositions that are injected or absorbed. An antigen (Ag) reacts with the products of specific humoral or cellular immunity. In some embodiments, an antigen also may be the specific binding target of the engineered CH2 scaffolds or binding moieties whether or not such interaction could produce an immunological response.

Avidity: binding affinity (e.g., increased) as a result from bivalent or multivalent binding sites that may simultaneously bind to a multivalent target antigen or receptor that is either itself multimeric or is present on the surface of a cell or virus such that it can be organized into a multimeric form. For example, the two Fab arms of an immunoglobulin can provide such avidity increase for an antigen compared with the binding of a single Fab arm, since both sites must be unbound for the immunoglobulin to dissociate.

Binding affinity: The strength of binding between a binding site and a ligand (e.g., between an antibody, a CH2 domain, or a CH3 domain and an antigen or epitope). The affinity of a binding site X for a ligand Y is represented by the dissociation constant (Kd), which is the concentration of Y that is required to occupy half of the binding sites of X present in a solution. A lower (Kd) indicates a stronger or higher-affinity interaction between X and Y and a lower concentration of ligand is needed to occupy the sites. In general, binding affinity can be affected by the alteration, modification and/or substitution of one or more amino acids in the epitope recognized by the paratope (portion of the molecule that recognizes the epitope). Binding affinity can also be affected by the alteration, modification and/or substitution of one or more amino acids in the paratope. Binding affinity can be the affinity of antibody binding an antigen.

In one example, binding affinity can be measured by end-point titration in an Ag-ELISA assay. Binding affinity can be substantially lowered (or measurably reduced) by the modification and/or substitution of one or more amino acids in the epitope recognized by the antibody paratope if the end-point titer of a specific antibody for the modified/substituted epitope differs by at least 4-fold, such as at least 10-fold, at least 100-fold or greater, as compared to the unaltered epitope.

CH2 or CH3 domain molecule: A polypeptide (or nucleic acid encoding a polypeptide) derived from an immunoglobulin CH2 or CH3 domain. Unless noted otherwise, the immunoglobulin can be IgG, IgA, IgD, IgE or IgM. The CH2 or CH3 molecule is composed of a number of parallel β-strands connected by loops of unstructured amino acid sequence. The CH2 or CH3 domain molecule can further comprise an additional amino acid sequence(s), such as a complete hypervariable loop. In some embodiments described herein, the CH2 or CH3 domains comprise one or more mutations in a loop region of the molecule. In some embodiments described herein, the CH2 or CH3 domains comprise one or more mutations in a scaffold region (e.g., for stabilization, etc.). A "loop region" of a CH2 or CH3 domain refers to the portion of the protein located between regions of β-sheet (for example, each CH2 domain comprises seven β-sheets, A to G, oriented from the N- to C-terminus). A CH2 domain comprises six loop regions: Loop 1, Loop 2, Loop 3, Loop A-B, Loop C-D and Loop E-F. Loops A-B, C-D and E-F are located between β-sheets A and B, C and D, and E and F, respectively. Loops 1, 2 and 3 are located between β-sheets B and C, D and E, and F and G, respectively. These loops in the natural CH2 domain are often referred to as structural loops.

The engineered CH2 and CH3 domain molecules disclosed herein can also comprise an N-terminal deletion, such as (but not limited to) a deletion of between about 1 to about 7 amino acids, for example, the N-terminal deletion is 1, 2, 3, 4, 5, 6 or 7 amino acids in length. The CH2 and CH3 domain molecules disclosed herein can also comprise a C-terminal deletion, such as (but not limited to) a deletion of about 1 to about 4 amino acid, for example the C-terminal deletion is 1, 2, 3 or 4 amino acids in length.

Naturally occurring CH2 and CH3 domain molecules are small in size, usually less than 15 kD. Engineered CH2 and CH3 domain molecules can vary in size depending on the length of donor loops inserted in the loop regions, how many donor loops are inserted and whether another molecule (such as a binding moiety, an effector molecule, or a label) is conjugated or linked to the CH2 or CH3 domain. In some embodiments, the CH2 or CH3 domain molecules do not comprise additional constant domains (e.g. CH1 or another CH2 or CH3 domain). In some embodiments, the CH2 domain is from IgG, IgA or IgD. In some embodiments, the "CH2 domain" is a CH3 domain from IgE or IgM, which is homologous to the CH2 domains of IgG, IgA or IgD.

The CH2 and CH3 domain molecules provided herein can be glycosylated or unglycosylated. For example, a recombinant CH2 or CH3 domain can be expressed in an appropriate yeast, insect, plant or mammalian cell to allow glycosylation of the molecule at one or more natural or engineered glycosylation sites in the protein. The recombinant CH2 or CH3 domains can be expressed with a mixture of glycosylation patterns as typically results from the production in a mammalian cell line like CHO (Schroder et al., Glycobiol 20(2): 248-259, 2010; Hossler et al., Glycobiol 19(9):936-949, 2009) or the CH2 domains can be made with substantially homogeneous (greater than 50% of one type) glycopatterns. A method of homogenously or nearly homogenously glycosylating recombinant proteins has been developed in genetically-engineered yeast (Jacobs et al., Nature Protocols 1(4): 58-70, 2009). The glycans added to the protein may be the same as occur naturally or may be forms not usually found on human glycoproteins. Non-limiting examples include Man5, GnMan5, GalGnMan5 GnMan3, GalGnMan3, Gn2Man3, Gal2Gn2Man3. In vitro reactions may be used to add additional components (such as sialic acid) to the glycans added in the recombinant production of the glycoprotein. Addition of different glycans may provide for improvements in half-life, stability, and other pharmaceutical properties, for example it is well known the presence of fucose in the usual N-glycans of the CH2 domain of antibodies affects ADCC (antibody dependent cellular cytotoxicity).

The CH2 and CH3 domain molecules provided herein can be stabilized or native molecules. Stabilized CH2Ds have certain alterations in their amino acid sequence to allow additional disulfide bonds to be formed without noticeable alteration of the protein's functions, e.g., see WO 2009/099961A2.

CH2D: A CH2 or CH3 domain molecule. The CH2 or CH3 domain molecule may be engineered such that the molecule specifically binds antigen. The CH2 and CH3 domain molecules engineered to bind antigen are among the smallest known antigen-specific binding antibody domain-based molecules that can retain Fc receptor binding.

Complementarity determining region (CDR): A short amino acid sequence found in the variable domains of antigen receptor (such as immunoglobulin and T cell receptor) proteins that provides the receptor with contact sites for antigen and its specificity for a particular antigen. Each polypeptide chain of an antigen receptor in an antibody contains three CDRs (CDR1, CDR2 and CDR3). Antigen receptors are typically composed of two polypeptide chains (a heavy chain and a light chain), therefore there are six CDRs for each antigen receptor that can come into contact with the antigen. Since most sequence variation associated with antigen receptors are found in the CDRs, these regions are sometimes referred to as hypervariable domains. In the present invention, the loops that are grafted onto L1, L2, and/or L3 loops of the CH2 domain scaffold (e.g., the loops used to replace either L1, L2, L3, both L1 and L2, both L1 and L3, both L2 and L3, or L1 and L2 and L3 of the CH2 domain scaffold) are not CDRs.

CDRs are found within loop regions of an antigen receptor (usually between regions of β-sheet structure). These loop regions are typically referred to as hypervariable loops. Each antigen receptor comprises six hypervariable loops: H1, H2, H3, L1, L2 and L3. For example, the H1 loop comprises CDR1 of the heavy chain and the L3 loop comprises CDR3 of the light chain. The CH2 domain scaffolds (or equivalent CH3 domain scaffolds) described herein may comprise engrafted amino acids sequences from a variable domain of an antibody, the engrafted amino acids comprising at least a portion of a CDR. The engrafted amino acids can also include additional amino acid sequence, such as a complete hypervariable loop. As used herein, a "functional fragment" of a CDR is at least a portion of a CDR that retains the capacity to bind a specific antigen. The loops may be mutated or rationally designed.

A numbering convention locating CDRs is described by Kabat et al. 1991, *Sequences of Proteins of Immunological Interest,* 5$^{th}$ Edition, U.S. Department of Health and Human Services, Public Health Service, National Institutes of Health, Bethesda, Md. (NIH Publication No. 91-3242).

Contacting: Placement in direct physical association, which includes both in solid and in liquid form.

Degenerate variant: As used herein, a "degenerate variant" of a CH2 or CH3 domain molecule is a polynucleotide encoding a CH2 or CH3 domain molecule that includes a sequence that is degenerate as a result of redundancies in the genetic code. There are 20 natural amino acids, most of which are specified by more than one codon. Therefore, all degenerate nucleotide sequences are included as long as the amino acid sequence of the CH2 or CH3 domain molecule encoded by the nucleotide sequence is unchanged.

The use of degenerate variant sequences that encode the same polypeptide is of great utility in the expression of recombinant multimeric forms of CH2Ds (CH2 domains). Linear gene constructs that use extensive repeats of the same DNA sequence are prone to deletion due to recombination. This can be minimized by the selection of codons that encode the same amino acids yet differ in sequence, designing the gene to avoid repeated DNA elements even though it encodes a repeated amino acid sequence, such as a linear dimer CH2D comprising two identical CH2Ds. Even if a dimer has different CH2Ds, much or all of the scaffold amino acid sequence may be identical, and certain trimeric CH2Ds may have identical linkers. Similar codon selection principles can be used to reduce repeats in a gene encoding any linear repeated domains, such as variable heavy chain multimers, Fibronectin domain multimers, ankyrin repeat proteins or other scaffold multimers. Preferably, the codons are well expressed in the selected host organism. Another use of the degenerate versions of the encoding nucleic acids may be to optimize expression in different expression systems. For example, *E. coli* expression systems may prefer one codon for an amino acid while a *Pichia* protein expression system may prefer a different codon for the same amino acid in that position of the protein.

Domain: A protein structure that retains its tertiary structure independently of the remainder of the protein. In some cases, domains have discrete functional properties and can be added, removed or transferred to another protein without a loss of function.

Effector molecule: A molecule, or the portion of a chimeric molecule, that is intended to have a desired effect on a cell to which the molecule or chimeric molecule is targeted. An effector molecule is also known as an effector moiety (EM), therapeutic agent, or diagnostic agent, or similar terms.

Epitope: An antigenic determinant. These are particular chemical groups or contiguous or non-contiguous peptide sequences on a molecule that are antigenic, that is, that elicit a specific immune response. An antibody binds a particular antigenic epitope based on the three dimensional structure of the antibody and the matching (or cognate) epitope.

Expression: The translation of a nucleic acid sequence into a protein. Proteins may be expressed and remain intracellular, become a component of the cell surface membrane, or be secreted into the extracellular matrix or medium.

Expression control sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (e.g., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is an array of nucleic acid control sequences that directs transcription of a nucleic acid. A promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. Both constitutive and inducible promoters are included (see, for example, Bitter et al. (1987) Methods in Enzymology 153:516-544).

Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see, for example, Bitter et al. (1987) Methods in Enzymology 153:516-544). For example, when cloning in bacterial systems, inducible promoters such as pL of bacteriophage lambda, plac, ptrp, ptac (ptrp-lac hybrid promoter) and the like may be used. In some embodiments, when cloning in mammalian cell systems, promoters derived from the genome of mammalian cells (such as the metallothionein promoter) or from mammalian viruses (such as the retrovirus long terminal repeat; the adenovirus late promoter; the vaccinia virus 7.5 K promoter, etc.) can be used. Promoters produced by recombinant DNA or synthetic techniques may also be used to provide for transcription of the nucleic acid sequences.

A polynucleotide can be inserted into an expression vector that contains a promoter sequence that facilitates the efficient transcription of the inserted genetic sequence of the host. The expression vector typically contains an origin of replication, a promoter, as well as specific nucleic acid sequences that allow phenotypic selection of the transformed cells.

Expression system: A system for expressing a gene product, e.g., a protein. Expression systems may be cell-based or cell-free. Examples of expression systems include but are not limited to bacterial systems (e.g., E. coli, B. subtilis), yeast systems (e.g., Pichia, S. cerevisiae), an insect system, a eukaryotic system, viral systems (e.g., baculovirus, lambda, retrovirus), and the like.

Fc binding regions: The FcRn binding region of the CH2 region is known to comprise the amino acid residues M252, I253, S254, T256, V259, V308, H310, Q311 (Kabat numbering of IgG). These amino acid residues have been identified from studies of the full IgG molecule and/or the Fc fragment to locate the residues of the CH2 domain that directly affect the interaction with FcRn. Three lines of investigation have been particularly illuminating: (a) crystallographic studies of the complexes of FcRn bound to Fc, (b) comparisons of the various human isotypes (IgG1, IgG2, IgG3 and IgG4) with each other and with IgGs from other species that exhibit differences in FcRn binding and serum half-life, correlating the variation in properties to specific amino acid residue differences, and (c) mutation analysis, particularly the isolation of mutations that show enhanced binding to FcRn, yet retain the pH-dependence of FcRn interaction. All three approaches highlight the same regions of CH2 region as crucial to the interaction with FcRn. The CH3 domain of IgG also contributes to the interaction with FcRn, but the protonation/deprotonation of H310 is thought to be primarily responsible and sufficient for the pH dependence of the interaction.

Fc Receptor and Complement Binding Regions of CH2D: Apart from FcRn, the CH2 domain is involved in binding other Fc receptors and also complement. The region of the CH2D involved in these interactions comprises the amino acid residues E233, L234, L235, G236, G237, P238, Y296, N297, E318, K320, K322, N327, (Kabat numbering of IgG). These amino acid residues have been identified from studies of the full IgG molecule and/or the Fc fragment to locate the residues of the CH2 domain that directly affect the interaction with Fc receptors and with complement. Three lines of investigation have been useful: (a) crystallographic studies of the complexes of a receptor (e.g. FcγRIIIa) bound to Fc, (b) sequence comparisons of the various human IgG isotypes (IgG1, IgG2, IgG3 and IgG4) and other immunoglobulin classes that exhibit differences in Fc Receptor binding, binding to complement or induction of pro-inflammatory or anti-inflammatory signals, correlating the variation in properties to specific amino acid residue differences, and (c) the isolation of mutations that show reduced or enhanced binding to Fc receptors or complement. The CH3 domain of IgG may contribute to the interaction with some Fc receptors (e.g. FcγRIa); however, the CH1-proximal end of the CH2 in the IgG molecule is the primary region of interaction, and the mutations in the CH3 domain of IgG may enhance Fc interaction with FcγRIa indirectly, perhaps by altering the orientation or the accessibility of certain residues of the CH2 domain. Additionally, though the residues are very close to the FcγRIIIa interaction site of CH2 revealed in the crystal structure, N297 may affect binding because it is the site of N-linked glycosylation of the CH2 domain. The state and nature of the N-linked glycan affect binding to Fc receptors (apart from FcRn); for example, glycosylated IgG binds better than unglycosylated IgG, especially when the glycoform lacks fucose. Greenwood J, Clark M, Waldmann H. Structural motifs involved in human IgG antibody effector functions Eur J Immunol 1993; 5: 1098-1104

Framework region: Amino acid sequences interposed between CDRs (or hypervariable regions). Framework regions include variable light and variable heavy framework regions. Each variable domain comprises four framework regions, often referred to as FR1, FR2, FR3 and FR4. The framework regions serve to hold the CDRs in an appropriate orientation for antigen binding. Framework regions typically form β-sheet structures. Framework regions are generally defined like CDRs with reference to certain amino acids in the Kabat numbering system. For example, Kabat numbering for antibodies assigns portions of the beta sheet framework to be included as part of a CDR.

Heterologous: A heterologous polypeptide or polynucleotide refers to a polypeptide or polynucleotide derived from a different source or species.

Hypervariable region: Regions of particularly high sequence variability within an antibody variable domain. The hypervariable regions form loop structures between the β-sheets of the framework regions. Thus, hypervariable regions are also referred to as "hypervariable loops." Each variable domain comprises three hypervariable regions, often referred to as HI, H2 and H3 in the heavy chain, and L1, L2 and L3 in the light chain.

Immune response: A response of a cell of the immune system, such as a B-cell, T-cell, macrophage or polymorphonucleocyte, to a stimulus such as an antigen. An immune response can include any cell of the body involved in a host defense response for example, an epithelial cell that secretes an interferon or a cytokine. An immune response includes, but is not limited to, an innate immune response or inflammation.

Immunoconjugate: A covalent linkage of an effector molecule to an antibody or a CH2 or CH3 domain molecule. The effector molecule can be a detectable label, biologically active protein, drug, cytotoxic molecule, or toxin (cytotoxic molecule).

Specific, non-limiting examples of toxins include, but are not limited to, abrin, ricin, *Pseudomonas* exotoxin (PE, such as PE35, PE37, PE38, and PE40), diphtheria toxin (DT), botulinum toxin, small molecule toxins, saporin, restrictocin or gelonin, or modified toxins thereof. Other cytotoxic agents that may be attached to an antibody or CH2 or CH3 domain include auristatin, maytansinoids, and cytolytic peptides. Other immunoconjugates may be composed of antibodies or CH2 or CH3 domains linked to drug molecules (ADC or "antibody drug conjugates"; Ducry and Stump, Bioconj Chem 21: 5-13, 2010; Erikson et al., Bioconj Chem 21: 84-92, 2010) or imaging agents. These toxins/immunotoxins may directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as domain la of PE and the B chain of DT) and replacing it with a different targeting moiety, such as a CH2 or CH3 domain molecule. In some embodiments, a CH2 or CH3 domain molecule is joined to an effector molecule (EM). Antibody drug conjugates (ADCs), which are drugs (e.g., cytotoxic agents) conjugated to antibodies (or fragments thereof), deliver therapeutic molecules to their conjugate binding partners. The effector molecule may be a small molecule drug or biologically active protein, such as erythropoietin. In some embodiments, the effector molecule may be another immunoglobulin domain, such as a VH or CH1 domain. In some embodiments, a CH2 (or CH3) domain joined to an effector molecule is further joined to a lipid or other molecule to a protein or peptide to increase its half-life. The linkage can be either by chemical or recombinant means. "Chemical means" refers to a reaction between the CH2 or CH3 domain molecule and the effector molecule such that there is a covalent bond formed between the two molecules to form one molecule. A peptide linker (short peptide sequence) can optionally be included between the CH2 or CH3 domain molecule and the effector molecule. Such a linker may be subject to proteolysis by an endogenous or exogenous linker to release the effector molecule at a desired site of action. Because immunoconjugates were originally prepared from two molecules with separate functionalities, such as an antibody and an effector molecule, they are also sometimes referred to as "chimeric molecules." The term "chimeric molecule," as used herein, therefore refers to a targeting moiety, such as a ligand, antibody or CH2 or CH3 domain molecule, conjugated (coupled) to an effector molecule.

The terms "conjugating," "joining," "bonding" or "linking" refer to making two polypeptides into one contiguous polypeptide molecule, or to covalently attaching a radionucleotide or other molecule to a polypeptide, such as a CH2 or CH3 domain molecule. In the specific context, the terms can in some embodiments refer to joining a ligand, such as an antibody moiety, to an effector molecule ("EM"). The terms "conjugating," "joining," "bonding" or "linking" may also refer to attaching a first CH2 (or CH3) domain to a second CH2 (or CH3) domain.

Immunogen: A compound, composition, or substance that is capable, under appropriate conditions, of stimulating an immune response, such as the production of antibodies or a T-cell response in an animal, including compositions that are injected or absorbed into an animal.

Isolated: An "isolated" biological component (such as a nucleic acid molecule or protein) that has been substantially separated or purified away from other biological components from which the component naturally occurs (for example, other biological components of a cell), such as other chromosomal and extra-chromosomal DNA and RNA and proteins, including other antibodies. Nucleic acids and proteins that have been "isolated" include nucleic acids and proteins purified by standard purification methods. An "isolated antibody" is an antibody that has been substantially separated or purified away from other proteins or biological components such that its antigen specificity is maintained. The term also embraces nucleic acids and proteins (including CH2 and CH3 domain molecules) prepared by recombinant expression in a host cell, as well as chemically synthesized nucleic acids or proteins, or fragments thereof.

Label: A detectable compound or composition that is conjugated directly or indirectly to another molecule, such as an antibody or CH2 or CH3 domain molecule, to facilitate detection of that molecule. Specific, non-limiting examples of labels include fluorescent tags, enzymatic linkages, and radioactive isotopes.

Library: A collection of multiple and varied molecules, for example a collection of multiple and varied CH2 domains (or CH3 domains) of the present invention. As an example, library members may be a collection of CH2 scaffolds with various different L1 loops. A library of CH2 molecules can include a collection of multiple and varied CH2 domain template molecules derived from methods described herein, wherein one or more loops of a CH2 domain scaffold are replaced with a donor loop. As an example, library members may be a collection of CH2 domain template molecules each with a different L1 loop (derived from a donor molecule), or each with a different L2 loop, a different L3 loop, different L1 and L2 loops, different L1 and L3 loops, different L2 and L3 loops, etc. In some embodiments, the library is a collection of varied CH2 domain template molecules with one or more loops having been replaced.

Ligand contact residue or Specificity Determining Residue (SDR): An amino acid residue within a donor molecule (or CDR) that participates in contacting a ligand or antigen. A ligand contact residue is also known as a specificity determining residue (SDR). A non-ligand contact residue is a residue in a CDR that does not participate in contacting a ligand. A non-ligand contact residue can also be a framework residue.

Linkers: covalent or very tight non-covalent linkages; chemical conjugation or direct gene fusions of various amino acid sequences, especially those rich in Glycine Serine, Proline, Alanine, or variants of naturally occurring linking amino acid sequences that connect immunoglobulin domains, and/or carbohydrates including but not limited to polyethylene glycols (PEGs), e.g., discrete PEGs (dPEGs). Typical lengths may range from 5 up to 20 or more amino acids, however the present invention is not limited to these lengths (e.g., the linker may be a peptide between 0 and 20 amino acids). The optimal lengths may vary to match the spacing and orientation of the specific target antigen(s), minimizing entropy but allowing effective binding of multiple antigens.

Modification: changes to a protein sequence, structure, etc., or changes to a nucleic acid sequence, etc. As used herein, the term "modified" or "modification," can include one or more mutations, deletions, substitutions, physical alteration (e.g., cross-linking modification, covalent bonding of a component, post-translational modification, e.g., acetylation, glycosylation, the like, or a combination thereof), the like, or a combination thereof. Modification, e.g., mutation, is not limited to random modification (e.g., random mutagenesis) but includes rational design as well.

Multimerizing Domain. Many domains within proteins are known that form a very tight non-covalent dimer or multimer by associating with other protein domain(s). Some of the smallest examples are the so-called leucine zipper motifs, which are compact domains comprising heptad repeats that can either self-associate to form a homodimer (e.g. GCN4); alternatively, they may associate preferentially with another leucine zipper to form a heterodimer (e.g. myc/max dimers) or more complex tetramers (Chem Biol. 2008 Sep. 22; 15(9): 908-19. A heterospecific leucine zipper tetramer. Deng Y, Liu J, Zheng Q, Li Q, Kallenbach N R, Lu M.). Closely related domains that have isoleucine in place of leucine in the heptad repeats form trimeric "coiled coil" assemblies (e.g. HIV gp41). Substitution of isoleucine for leucine in the heptad repeats of a dimer can alter the favoured structure to a trimer. Small domains have advantages for manufacture and maintain a small size for the whole protein molecule, but larger domains can be useful for multimer formation. Any domains that form non-covalent multimers could be employed. For example, the CH3 domains of IgG form homodimers, while CH1 and CL domains of IgG form heterodimers.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2'-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes a complementary RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form. "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together and can be made by artificially combining two otherwise separated segments of sequence. This artificial combination is often accomplished by chemical synthesis or, more commonly, by the artificial manipulation of isolated segments of nucleic acids, for example, by genetic engineering techniques. Recombinant nucleic acids include nucleic acid vectors comprising an amplified or assembled nucleic acid, which can be used to transform or transfect a suitable host cell. A host cell that comprises the recombinant nucleic acid is referred to as a "recombinant host cell." The gene is then expressed in the recombinant host cell to produce a "recombinant polypeptide." A recombinant nucleic acid can also serve a non-coding function (for example, promoter, origin of replication, ribosome-binding site and the like).

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable vehicles: The pharmaceutically acceptable carriers (vehicles) useful in this disclosure may be conventional but are not limited to conventional vehicles. For example, E. W. Martin, *Remington's Pharmaceutical Sciences*, Mack Publishing Co., Easton, Pa., 15th Edition (1975) and D. B. Troy, ed. Remington: The Science and Practice of Pharmacy, Lippincott Williams & Wilkins, Baltimore Md. and Philadelphia, Pa., 21$^{st}$ Edition (2006) describe compositions and formulations suitable for pharmaceutical delivery of one or more therapeutic compounds or molecules, such as one or more antibodies, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. As a non-limiting example, the formulation for injectable trastuzumab includes L-histidine HCl, L-histidine, trehalose dihydrate and polysorbate 20 as a dry powder in a glass vial that is reconstituted with sterile water prior to injection. Other formulations of antibodies and proteins for parenteral or subcutaneous use are well known in the art. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues that are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those that are recombinantly or synthetically produced. The term "residue" or "amino acid residue" includes reference to an amino acid that is incorporated into a protein, polypeptide, or peptide.

"Conservative" amino acid substitutions are those substitutions that do not substantially affect or decrease an activity or antigenicity of a polypeptide. For example, a polypeptide can include at most about 1, at most about 2, at most about 5, at most about 10, or at most about 15 conservative substitutions and specifically bind an antibody that binds the original polypeptide. The term conservative variation also includes the use of a substituted amino acid in place of an unsubstituted parent amino acid, provided that antibodies raised antibodies raised to the substituted polypeptide also immunoreact with the unsubstituted polypeptide. Examples of conservative substitutions include: (i) Ala-Ser; (ii) Arg-Lys; (iii) Asn-Gln or His; (iv) Asp-Glu; (v) Cys-Ser; (vi) Gin-Asn; (vii) Glu-Asp; (viii) His-Asn or Gln; (ix) Ile-Leu or Val; (x) Leu-Ile or Val; (xi) Lys-Arg, Gln, or Glu; (xii) Met-Leu or Ile; (xiii) Phe-Met, Leu, or Tyr; (xiv) Ser-Thr; (xv) Thr-Ser; (xvi) Trp-Tyr; (xvii) Tyr-Trp or Phe; (xviii) Val-Ile or Leu.

Conservative substitutions generally maintain (a) the structure of the polypeptide backbone in the area of the substitution, for example, as a sheet or helical conformation, (b) the charge or hydrophobicity of the molecule at the target site, and/or (c) the bulk of the side chain. The substitutions which in general are expected to produce the greatest changes in protein properties will be non-conservative, for instance changes in which (a) a hydrophilic residue, for example, serine or threonine, is substituted for (or by) a hydrophobic residue, for example, leucine, isoleucine, phenylalanine, valine or alanine; (b) a cysteine or proline is substituted for (or by) any other residue; (c) a residue having an electropositive side chain, for example, lysine, arginine, or histidine, is substituted for (or by) an electronegative residue, for example, glutamate or aspartate; or (d) a residue having a bulky side chain, for example, phenylalanine, is substituted for (or by) one not having a side chain, for example, glycine.

Preventing, treating, managing, or ameliorating a disease: "Preventing" a disease refers to inhibiting the full development of a disease. "Treating" refers to a therapeutic intervention that ameliorates a sign or symptom of a disease or pathological condition after it has begun to develop. "Managing" refers to a therapeutic intervention that does not allow the signs or symptoms of a disease to worsen. "Ameliorating" refers to the reduction in the number or severity of signs or symptoms of a disease.

Probes and primers: A probe comprises an isolated nucleic acid attached to a detectable label or reporter molecule. Primers are short nucleic acids, and can be DNA oligonucleotides 15 nucleotides or more in length, for example. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, for example, by the polymerase chain reaction (PCR) or other nucleic-acid amplification methods known in the art. One of skill in the art will appreciate that the specificity of a particular probe or primer increases with its length. Thus, for example, a primer comprising 20 consecutive nucleotides will anneal to a target with a higher specificity than a corresponding primer of only 15 nucleotides. Thus, in order to obtain greater specificity, probes and primers may be selected that comprise 20, 25, 30, 35, 40, 50 or more consecutive nucleotides.

Purified: The term purified does not require absolute purity; rather, it is intended as a relative term. Thus, for example, a purified CH2 or CH3 domain molecule is one that is isolated in whole or in part from naturally associated proteins and other contaminants in which the molecule is purified to a measurable degree relative to its naturally occurring state, for example, relative to its purity within a cell extract or biological fluid.

The term "purified" includes such desired products as analogs or mimetics or other biologically active compounds wherein additional compounds or moieties are bound to the CH2 or CH3 domain molecule in order to allow for the attachment of other compounds and/or provide for formulations useful in therapeutic treatment or diagnostic procedures.

Generally, substantially purified CH2 or CH3 domain molecules include more than 80% of all macromolecular species present in a preparation prior to admixture or formulation of the respective compound with additional ingredients in a complete pharmaceutical formulation for therapeutic administration. Additional ingredients can include a pharmaceutical carrier, excipient, buffer, absorption enhancing agent, stabilizer, preservative, adjuvant or other like co-ingredients. More typically, the CH2 or CH3 domain molecule is purified to represent greater than 90%, often greater than 95% of all macromolecular species present in a purified preparation prior to admixture with other formulation ingredients. In other cases, the purified preparation may be essentially homogeneous, wherein other macromolecular species are less than 1%.

Recombinant protein: For a recombinant nucleic acid, see "Recombinant Nucleic Acid" above. A recombinant protein or polypeptide is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques. Recombinant proteins may be made in cells transduced, transfected, or transformed with genetic elements to direct the synthesis of the heterologous protein. They may also be made in cell-free systems. Host cells that are particularly useful include mammalian cells such as CHO and HEK 293, insect cells, yeast such as *Pichia pastoris* or *Saccharomyces*, or bacterial cells such as *E. coli* or *Pseudomonas*.

Sample: A portion, piece, or segment that is representative of a whole. This term encompasses any material, including for instance samples obtained from a subject.

A "biological sample" is a sample obtained from a subject including, but not limited to, cells, tissues and bodily fluids. Bodily fluids include, for example, saliva, sputum, spinal fluid, urine, blood and derivatives and fractions of blood, including serum and lymphocytes (such as B cells, T cells and subfractions thereof). Tissues include those from biopsies, autopsies and pathology specimens, as well as biopsied or surgically removed tissue, including tissues that are, for example, unfixed, frozen, fixed in formalin and/or embedded in paraffin.

In some embodiments, a biological sample is obtained from a subject, such as blood or serum. A biological sample is typically obtained from a mammal, such as a rat, mouse, cow, dog, guinea pig, rabbit, or primate. In some embodiments, the primate is macaque, chimpanzee, or a human.

Scaffold: In some embodiments, a CH2 or CH3 domain scaffold is a CH2 or CH3 domain that can be used as a platform to introduce donor loops and/or mutations (such as into the loop regions) in order to confer antigen binding to the CH2 or CH3 domain. In some embodiments, the scaffold is altered to exhibit increased stability compared with the native CH2 or CH3 domain. In particular examples, the scaffold is mutated to introduce pairs of cysteine residues to allow formation of one or more non-native disulfide bonds. In some cases, the scaffold is a CH2 or CH3 domain having an N-terminal deletion, such as a deletion of about 1 to about 7 amino acids. Scaffolds are not limited to these definitions.

Sequence identity: The similarity between nucleotide or amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants will possess a relatively high degree of sequence identity overall or in certain regions when aligned using standard methods.

Methods of alignment of sequences for comparison are well known in the art. Various programs and alignment algorithms are described in: Smith and Waterman, Adv. Appl. Math. 2:482, 1981; Needleman and Wunsch, Journal of Molecular Biol. 48:443, 1970; Pearson and Lipman, Proc. Natl. Acad. Sci. U.S.A. 85:2444, 1988; Higgins and Sharp, Gene 73:237-244, 1988; Higgins and Sharp, CABIOS 5:151-153, 1989; Corpet et al., Nucleic Acids Research 16:10881-10890, 1988; and Pearson and Lipman, Proc. Natl. Acad. Sci. U.S.A. 85:2444, 1988. Altschul et al., Nature Genetics 6:119-129, 1994.

The NCBI Basic Local Alignment Search Tool (BLAST™) (Altschul et al., Journal of Molecular Biology 215:403-410, 1990.) is available from several sources, including the National Center for Biotechnology Information (NCBI, Bethesda, Md.) and on the Internet, for use in connection with the sequence analysis programs blastp, blastn, blastx, tblastn and tblastx.

Specific binding agent: An agent that binds substantially only to a defined target. Thus an antigen specific binding agent is an agent that binds substantially to an antigenic polypeptide or antigenic fragment thereof. In one embodiment, the specific binding agent is a monoclonal or polyclonal antibody or a CH2 or CH3 domain molecule that specifically binds the antigenic polypeptide or antigenic fragment thereof.

The term "specifically binds" refers to the preferential association of a binding agent, such as a CH2D or other ligand molecule, in whole or part, with a cell or tissue bearing that target of that binding agent and not to cells or tissues lacking a detectable amount of that target. It is, of course, recognized that a certain degree of non-specific interaction may occur between a molecule and a non-target cell or tissue. Nevertheless, specific binding may be distinguished as mediated through specific recognition of the antigen. Specific binding results in a much stronger association between the CH2 or CH3 domain molecule and cells bearing the target molecule than between the bound or CH2 or CH3 domain molecule and cells lacking the target molecule. Specific binding typically results in greater than 2-fold, such as greater than 5-fold, greater than 10-fold, or greater than 100-fold increase in amount of bound CH2 or CH3 domain molecule (per unit time) to a cell or tissue bearing the target polypeptide as compared to a cell or tissue lacking the target polypeptide, respectively. Specific binding to a protein under such conditions requires a CH2 or CH3 domain molecule that is selected for its specificity for a particular protein. A variety of immunoassay formats are appropriate for selecting CH2 or CH3 domain molecules specifically reactive with a particular protein. For example, solid-phase ELISA immunoassays are routinely used.

Subject: Living multi-cellular organisms, including vertebrate organisms, a category that includes both human and non-human mammals.

Therapeutic agents include such compounds as nucleic acids, proteins, peptides, amino acids or derivatives, glycoproteins, radioisotopes, lipids, carbohydrates, small molecules, recombinant viruses, or the like. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, such as a CH2 or CH3 domain molecule, may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies are well known to those of skill in the art. See, for example, U.S. Pat. No. 4,957,735; and Connor et al. 1985, Pharm. Ther. 28:341-365. Diagnostic agents or moieties include radioisotopes and other detectable labels. Detectable labels useful for such purposes are also well known in the art, and include radioactive isotopes such as $Tc^{99m}$, $In^{111}$, $^{32}P$, $^{125}I$, and $^{131}I$, fluorophores, chemiluminescent agents, and enzymes.

Therapeutically effective amount: A quantity of a specified agent sufficient to achieve a desired effect in a subject being treated with that agent. Such agents include the CH2 or CH3 domain molecules described herein. For example, this may be the amount of an HIV-specific CH2 domain molecule useful in preventing, treating or ameliorating infection by HIV. Ideally, a therapeutically effective amount of a CH2D is an amount sufficient to prevent, treat or ameliorate infection or disease, such as is caused by HIV infection in a subject without causing a substantial cytotoxic effect in the subject. The therapeutically effective amount of an agent useful for preventing, ameliorating, and/or treating a subject will be dependent on the subject being treated, the type and severity of the affliction, and the manner of administration of the therapeutic composition.

Toxin: See Immunoconjugate

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration. Such cells are sometimes called transformed cells.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Viral-associated antigen (VAAs): A viral antigen that can stimulate viral-specific T-cell-defined immune responses. Exemplary VAAs include, but are not limited to, an antigen from human immunodeficiency virus (HIV), BK virus, JC virus, Epstein-Barr virus (EBV), cytomegalovirus (CMV), adenovirus, respiratory syncytial virus (RSV), herpes simplex virus 6 (HSV-6), parainfluenza 3, or influenza B.

BRIEF DESCRIPTION OF THE DRAWINGS

In FIG. 1, HiswtCH2 to rFcRn has a $k_a=2.028\times10^4$ (1/Ms); $k_d=0.00184$ (1/s); $K_D=90.8$ nM. HiswtCH2 was tested at 75, 150, 300, 600, 1200 nM. The A curves (1A, 2A, 3A, 4A, 5A, and 6A) are binding curves; the B curves (1B, 2B, 3B, 4B, 5B, and 6B) are fitted curves. The $K_D$ was high because dissociation with pH 8 buffer did not completely remove HiswtCH2 at the end of each binding cycle.

DESCRIPTION OF PREFERRED EMBODIMENTS

Figure 1:
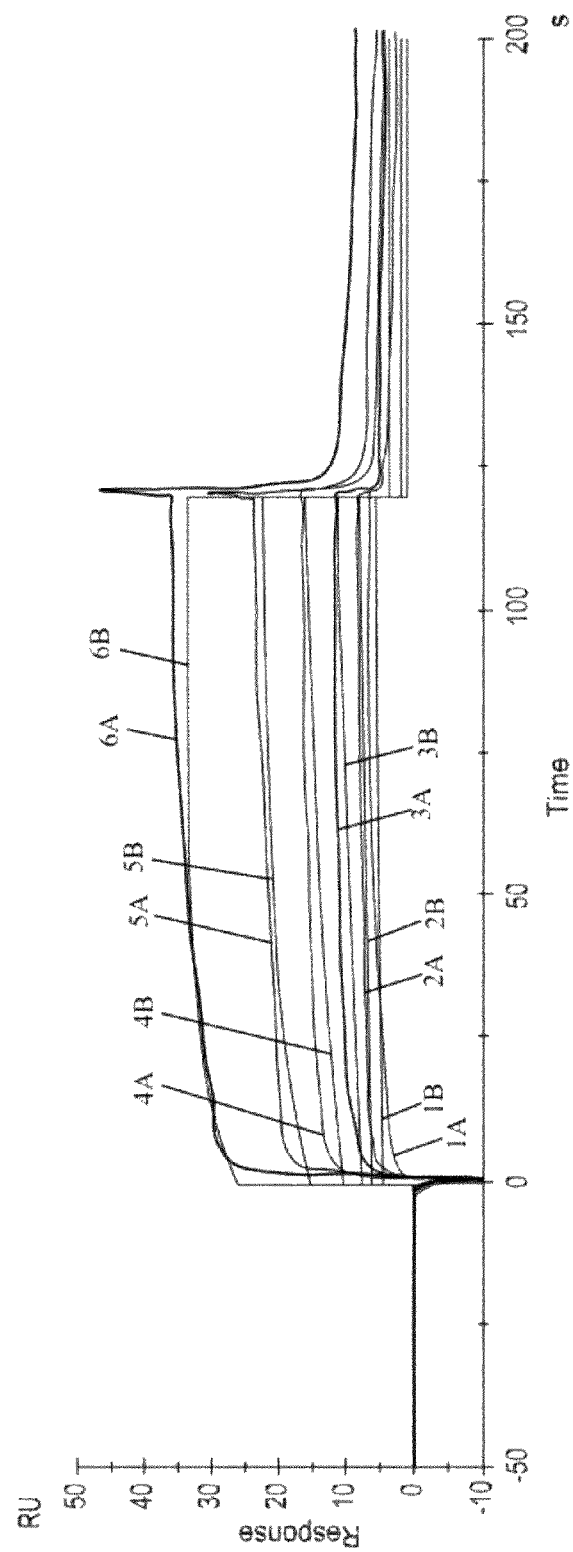
FIG. 1 shows Biacore analysis of the binding of wild type (WT) CH2 ("HiswtCH2") to rFcRn. For reference, the WT CH2 sequence (without the HIS tag) is shown in SEQ ID NO: 1. "HiswtCH2" of FIG. 1 is the WT CH2 sequence with a His tag, e.g., a group of histidine residues in a row, e.g., 6 histidine residues.
Figure 2A:
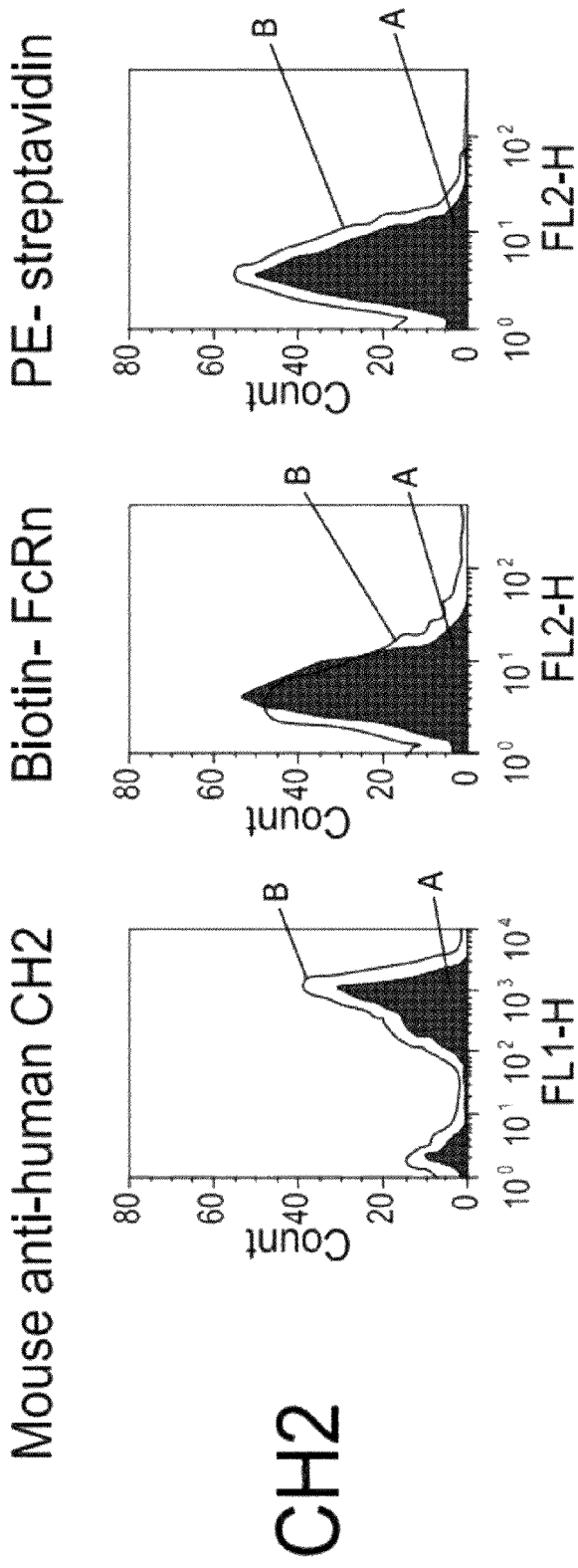
FIG. 2 a-d show binding of CH2, m01s, Fc, and CH3 to soluble FcRn on yeast cells at pH 6.0. CH2, m01s, Fc and CH3 was cloned into vector pYD7 for yeast expression. Fluorescence intensity shift between pH7.4 (blue) and pH 6.0 (red) was compared. For detection of the soluble FcRn binding: biotin-soluble FcRn was added to the yeast cells. PE-streptavidin was used for measurement of the fluorescence intensity. For detection of the expression: Expression CH2, m01s, and Fc: A monoclonal mouse anti-human CH2 was used as primary antibody; Alexa Fluor 488-conjugated goat anti-mouse IgG was used for measurement of the fluorescence intensity. Expression of CH3: Alexa Fluor 488 conjugated goat anti-human Fc polyclonal used for antibody was used for measurement of the fluorescence intensity directly. For determination of the binding specificity: Only PE-streptavidin was used for measurement of the fluorescence intensity directly.
Figure 2B:
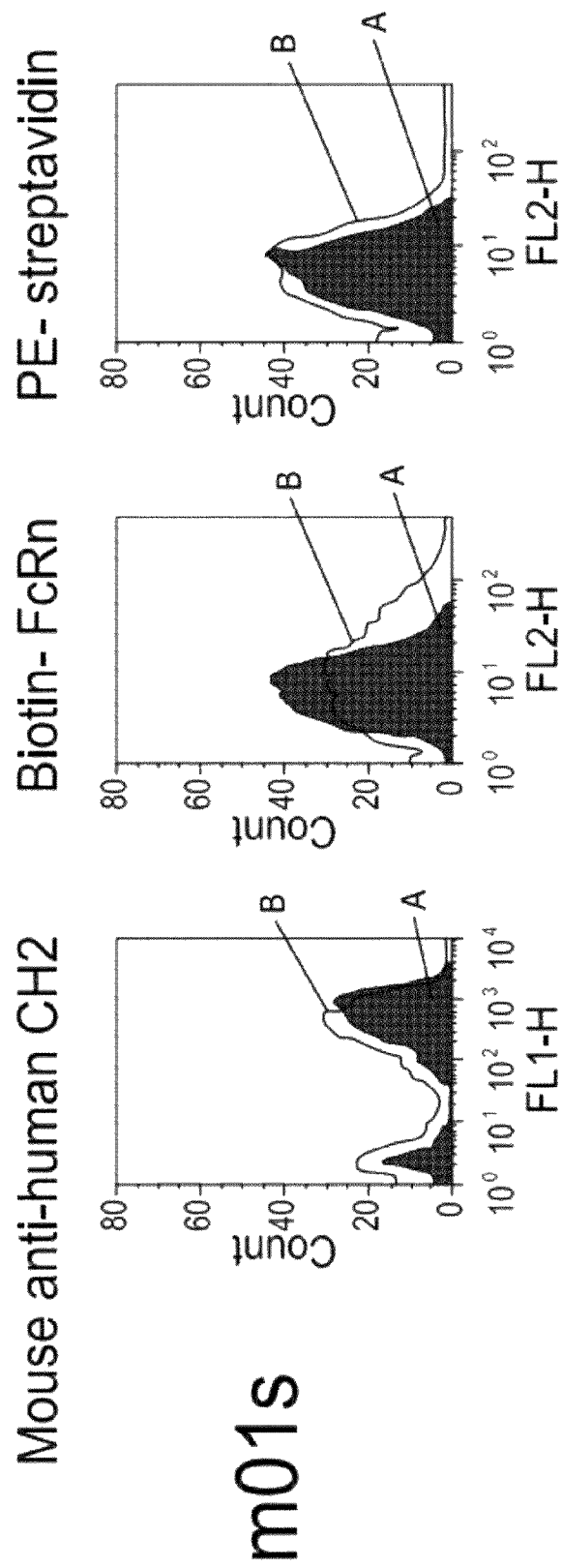
Figure 2C:
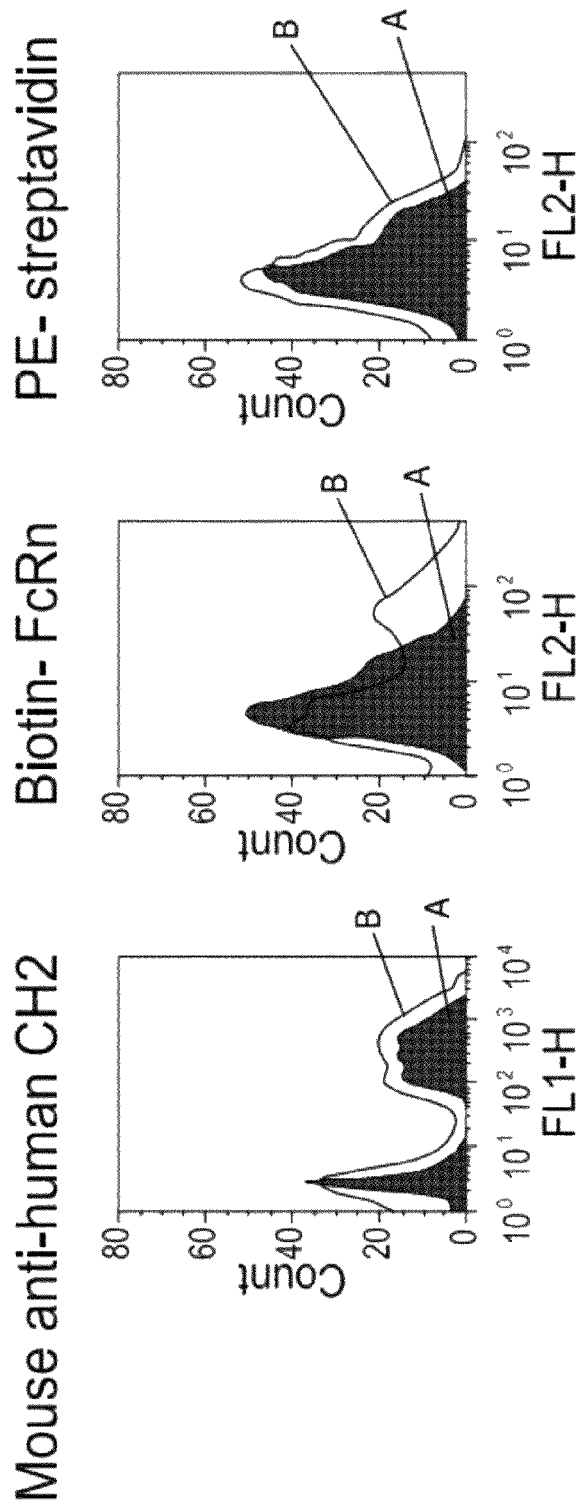
Figure 2D:
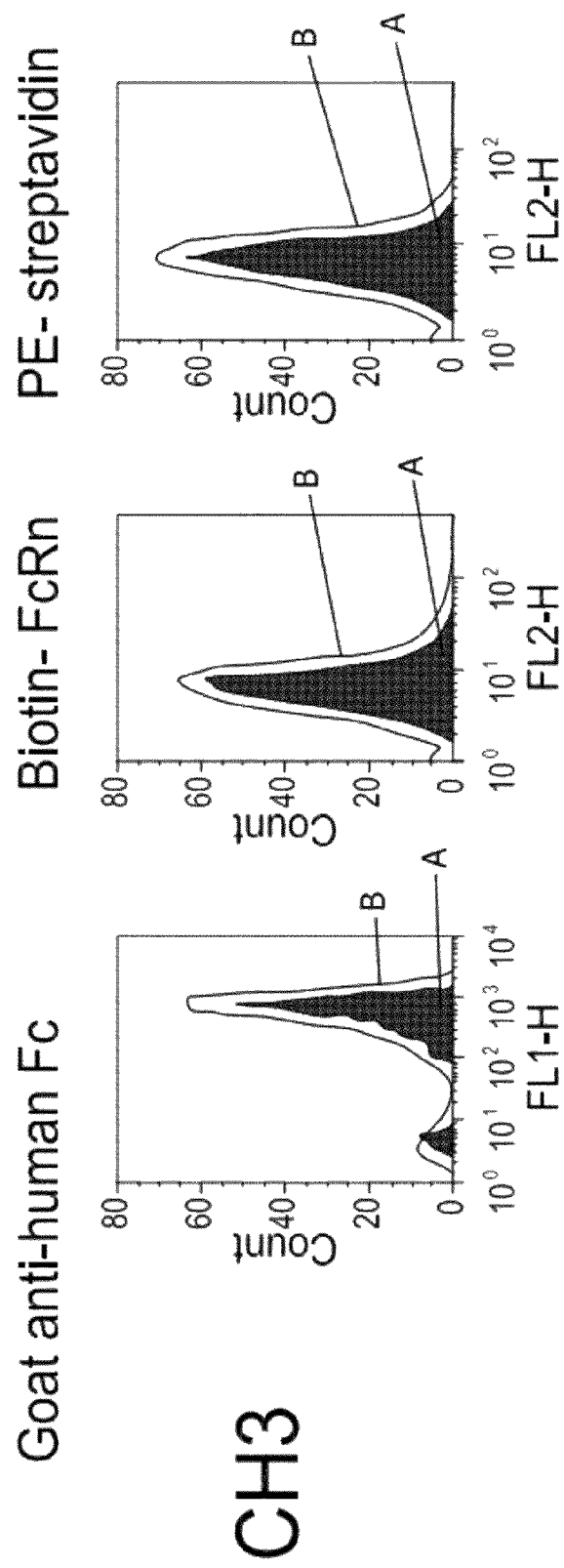

As used herein, the term "CH2 domain scaffold" or "CH2 domain" or "CH2D" refers to a CH2 domain of IgG, IgA, or IgD, or a fragment thereof; or a CH2-like domain (e.g., a peptide domain substantially resembling a CH2 domain of IgG, IgA or IgD) or a fragment thereof; or peptide domain functionally equivalent to or substantially resembling a CH2 domain of IgG, IgA, IgD, or a fragment thereof. Domains that substantially resemble a CH2 domain of IgG, IgA, or IgD may include but are not limited to a CH3 domain of IgE or IgM, or fragments thereof.

Table 1 shows the sequence corresponding to the CH2 domain of human IgG1 (SEQ ID NO: 1). As used herein, the term "wild type CH2" refers to the native human CH2 sequence of IgG shown in SEQ ID NO: 1. The present invention is not limited to using human CH2 of IgG1. Corresponding CH2 domain sequences are available from other human Igs, and corresponding CH2 domain sequences are available from other Igs of other mammals, e.g., macaque IgG. As used herein, the term "His tag" refers to a group of histidines, e.g., six histidines, located at either the N-terminus, the C-terminus, or at both termini of the molecule.

TABLE 1

```
SEQ ID NO: 1 - CH2 domain sequence of Human IgG1 (residues 231-342):

2          2          2          2          2          2
         3          4          5          6          7          8
1234567890 1234567890 1234567890 1234567890 1234567890 1234567890
APELLGGPSV FLFPPKPKDT LMISRTPEVT CVVVDVSHED PEVKFNWYVD GVEVHNAKTK 2          3          3          3          3          3
         9          0          1          2          3          4
1234567890 1234567890 1234567890 1234567890 1234567890 12
PREEQYNSTY RVVSVLTVLH QDWLNGKEYK CKVSNKALPA PIEKTISKAK GQ
```

The present invention features novel "CH2 domain template molecules" and methods of design of such CH2 domain template molecules. Loops from donor molecules (e.g., from a database of domains of donor molecules), e.g., the "donor loops," are transferred to a CH2 domain scaffold (e.g., "the acceptor"), such as but not limited to a human CH2 domain scaffold, to a create CH2 domain template molecules (e.g., the end product). The donor molecules may be chosen based on the length of one or more of its loops (L1, L2, and L3). For example, if the CH2 domain scaffold's L2 loop is to be replaced, a donor molecule may be selected because its L1 loop and L3 loop closely match (e.g., an exact match, plus or minus one amino acid, plus or minus two amino acids, plus or minus three amino acids, plus or minus four amino acids, plus or minus five amino acids, plus or minus more than five amino acids, etc.) the length of the L1 loop and L3 loop, respectively, of the CH2 domain scaffold, and after the donor molecule is chosen the L2 loop of that chosen donor molecule is used to replace the L2 loop of the CH2 domain scaffold Ideally, in some embodiments, a "match" is the same length, or same length plus or minus one amino acid. However, some cases have poorer matches available in the structural database, and in such cases the closest match in length will identify the preferred donor. Any loop transfer with the exact lengths for all 3 corresponding donor acceptor loops will be referred to as an "exact match." On the other hand, if there is a difference in lengths even in one of the loops, it will be referred to as "closely matches." In some embodiments, if the CH2 domain scaffold's L1 loop is to be replaced, a donor molecule may be selected because its L2 loop and L3 loop closely match (e.g., an exact match, plus or minus one amino acid, plus or minus two amino acids, plus or minus three amino acids, plus or minus four amino acids, plus or minus five amino acids, plus or minus more than five amino acids, etc.) the length of the L2 loop and L3 loop, respectively, of the CH2 domain scaffold, and after the donor molecule is chosen the L1 loop of that chosen donor molecule is used to replace the L1 loop of the CH2 domain scaffold. In some embodiments, if the CH2 domain scaffold's L3 loop is to be replaced, a donor molecule may be selected because its L1 loop and L2 loop closely match (e.g., an exact match, plus or minus one amino acid, plus or minus two amino acids, plus or minus three amino acids, plus or minus four amino acids, plus or minus five amino acids, plus or minus more than five amino acids, etc.) the length of the L1 loop and L2 loop, respectively, of the CH2 domain scaffold, and after the donor molecule is chosen the L3 loop of that chosen donor molecule is used to replace the L3 loop of the CH2 domain scaffold.

Selection of donor molecules (and donor loops) in this manner (e.g., "matching" lengths of one or two or all three of the loops) may help the CH2 domain template molecule (end product) retain some of the structure of the CH2 domain scaffold. Maintaining structural resemblance to the CH2 domain scaffold may allow for general retention (or even improvement) of certain properties of the molecule, for example stability (see below).

The donor loop that actually replaces the loop of the CH2 domain scaffold may or may not necessarily have a length that is identical or similar to that of the loop it replaces. As an example, if the L2 loop of the CH2 domain scaffold is replaced with a donor L2 loop from a donor molecule, the donor L2 loop may have a longer length than the L2 loop of the CH2 domain (and the additional length may be that the donor L2 loop naturally has more amino acids than the L2 loop of the CH2 domain or amino acids are added to the donor L2 loop, for example).

More specifically, the present invention features CH2 domain template molecules comprising a CH2 domain scaffold of IgG, IgA, IgD, IgE, or IgM (the CH2 domain scaffold of IgE or IgM referring to the CH3 domain of IgE or IgM, respectively) having a L1 loop [BC], a L2 loop [DE], and a L3 loop [FG]. In some embodiments, the L1 loop is replaced with a donor loop (e.g., the donor L1 loop) of a donor molecule (the donor molecule comprises a donor L1 loop, a donor L2 loop, and a donor L3 loop). In this example, a donor molecule is selected if the length of the donor L2 loop closely matches the length of the L2 loop of the CH2 domain scaffold and the length of the donor L3 loop closely matches the length of the L3 loop of the CH2 domain scaffold. If the donor L2 loop and the donor L3 loop closely match (e.g., the lengths of the donor L2 loop and donor L3 loop closely match the respective loops of the CH2 domain scaffold), then the L1 loop of the CH2 scaffold is replaced with the donor L1 loop of the donor molecule (the donor L2 loop and the donor L3 loop are not transferred to the CH2 domain scaffold in this case).

As used herein, the terms "closely matching" length, lengths that "closely match," or a length that "closely matches" generally refer to a length that is an exact length, a length that is plus or minus one amino acid, a length that is plus or minus two amino acids, a length that is plus or minus three amino acids, a length that is plus or minus four amino acids, a length that is plus or minus five amino acids, or a length that is plus or minus more than five amino acids (e.g., a length that is plus or minus six amino acids, a length that is plus or minus seven amino acids, a length that is plus or minus eight amino acids, a length that is plus or minus nine amino acids, a length that is plus or minus ten amino acids, a length that is plus or minus more than ten amino acids, etc.). Any loop transfer with the exact lengths for all 3 corresponding donor acceptor loops will be referred to as an "exact match." On the other hand, if there is a difference in lengths even in one of the loops, it will be referred to as a "close match" or "closely matches." In some embodiments, a length that is an exact match is ideal. In some embodiments, a length that is plus or minus one amino acid is ideal. In some embodiments, a length that is plus or minus two amino acids is ideal. In some embodiments, a length that is plus or minus three amino acids is ideal. In some embodiments, a length that is plus or minus four amino acids is ideal. In some embodiments, a length that is plus or minus five or more amino acids is ideal. In some embodiments, loops have poor matches available in the structural database, and in such cases the closest match in length will identify a donor (e.g., a preferred donor), e.g., the length may be plus or minus several amino acids versus an exact match or a match plus or minus one (or two) amino acids, for example.

In addition to the CH2 domains (or the structurally corresponding CH3 domains) serving as acceptor molecules for the grafted loop(s), derivatives of these CH2 domains can be used as acceptors. For example, a CH2 domain template already bearing one or more grafted loops might serve as an acceptor for a further grafting of one or more loops. In some embodiments, a CH2 domain template already bearing grafted L1 and L3 loops might serve as an acceptor for a further grafting of a L2. In some embodiments, a CH2 domain template already bearing grafted L1 and L2 loops might serve as an acceptor for a further grafting of a L3. In some embodiments, a CH2 domain template already bearing grafted L2 and L3 loops might serve as an acceptor for a further grafting of a L1. In some embodiments, a CH2 domain template already bearing a grafted L1 loop might serve as an acceptor for a further grafting of a L2 and L3 loop. In some embodiments, a CH2 domain template already bearing a grafted L2 loop might serve as an acceptor for a further grafting of a L1 and L3 loop. In some embodiments, a CH2 domain template already bearing a grafted L3 loop might serve as an acceptor for a further grafting of a L1 and L2 loop.

In some embodiments, a CH2 domain template or a CH2 library member (having one or more grafted loops) may serve as the "CH2 domain scaffold," for example for further iterative cycles of grafting, e.g., for improving binding to a target.

In some embodiments, the L2 loop is replaced with a donor loop (e.g., a donor L2 loop) of a donor molecule (the donor molecule comprises a donor L1 loop, a donor L2 loop, and a donor L3 loop). In this example, a donor molecule is selected if the length of the donor L1 loop of the donor molecule closely matches the length of the L1 loop of the CH2 domain scaffold and the length of the donor L3 loop of the donor molecule closely matches the length of the L3 loop of the CH2 domain scaffold. If the donor L1 loop and the donor L3 loop closely match (e.g., the lengths of the donor L1 loop and the donor L3 loop closely match the respective loops of the CH2 domain scaffold), then the L2 loop of the CH2 scaffold is replaced with the donor L2 loop of the donor molecule (the donor L1 loop and the donor L3 loop are not transferred to the CH2 domain scaffold in this case).

In some embodiments, the L3 loop is replaced with a donor loop (e.g., a donor L3 loop) of a donor molecule (the donor molecule comprises a donor L1 loop, a donor L2 loop, and a donor L3 loop). In this example, a donor molecule is selected if the length of the donor L1 loop of the donor molecule closely matches the length of the L1 loop of the CH2 domain scaffold and the length of the donor L2 loop of the donor molecule closely matches the length of the L2 loop of the CH2 domain scaffold. If the donor L1 and donor L2 loop closely match (e.g., the lengths of the donor L1 loop and donor L2 loop closely match the respective loops of the CH2 domain scaffold), then the L3 loop of the CH2 scaffold is replaced with the donor L3 loop of the donor molecule (the donor L1 loop and the donor L2 loop are not transferred to the CH2 domain scaffold in this case).

In some embodiments, both the L1 loop and L2 loop are replaced with a first donor loop and a second donor loop of a donor molecule, respectively (the donor molecule comprises a donor L1 loop, a donor L2 loop, and a donor L3 loop). In this example, a donor molecule is selected if the length of the donor L3 loop closely matches the length of the L3 loop of the CH2 domain scaffold. If the donor L3 loop closely matches (e.g., the length of the donor L3 loop closely matches the length of the L3 loop of the CH2 domain scaffold), then either the L1 loop of the CH2 domain scaffold is replaced with the donor L1 loop of the donor molecule and the L2 loop of the CH2 domain scaffold is replaced with the donor L2 loop of the donor molecule, or the L2 loop of the CH2 domain scaffold is replaced with the donor L1 loop of the donor molecule and the L1 loop of the CH2 domain scaffold is replaced with the donor L2 loop of the donor molecule (the donor L3 loop is not transferred to the CH2 domain scaffold in this case).

In some embodiments, both the L1 loop and the L3 loop are replaced with a first donor loop and a second donor loop of a donor molecule, respectively (the donor molecule comprises a donor L1 loop, a donor L2 loop, and a donor L3 loop). In this example, a donor molecule is selected if the length of the donor L2 loop of the donor molecule closely matches the length of the L2 loop of the CH2 domain scaffold. If the donor L2 loop closely matches (e.g., the length of the donor L2 loop v the length of the L2 loop of the CH2 domain scaffold), then either the L1 loop of the CH2 domain scaffold is replaced with the donor L1 loop of the donor molecule and the L3 loop of the CH2 domain scaffold is replaced with the donor L3 loop of the donor molecule, or the L1 loop of the CH2 domain scaffold is replaced with the donor L3 loop of the donor molecule and the L3 loop of the CH2 domain scaffold is replaced with the donor L1 loop of the donor molecule (the donor L2 loop is not transferred to the CH2 domain scaffold in this case).

In some embodiments, both the L2 loop and the L3 loop are replaced with a first donor loop and a second donor loop of a donor molecule, respectively (the donor molecule comprises a donor L1 loop, a donor L2 loop, and a donor L3 loop). In this example, a donor molecule is selected if the length of the donor L1 loop of the donor molecule closely matches the length of the L1 loop of the CH2 domain scaffold. If the donor L1 loop closely matches (e.g., the length of the donor L1 loop closely matches the length of the L1 loop of the CH2 domain scaffold), then either the L2 loop of the CH2 domain scaffold is replaced with the donor L2 loop of the donor molecule and the L3 loop of the CH2 domain scaffold is replaced with the donor L3 loop of the donor molecule, or the L2 loop of the CH2 domain scaffold is replaced with the donor L3 loop of the donor molecule and the L3 loop of the CH2 domain scaffold is replaced with the donor L2 loop of the donor molecule (the donor L1 loop is not transferred to the CH2 domain scaffold in this case).

In some embodiments, the L1 loop, the L2 loop, and the L3 loop are replaced with a first donor loop, a second donor loop, and a third donor loop of a donor molecule, respectively.

At least one (up to three loops), e.g., L1, L2, L3, L1 and L2, L1 and L3, L2 and L3, or L1 and L2 and L3, from a donor molecule are transferred to the CH2 domain scaffold to create the "CH2 domain template molecule." Without wishing to limit the present invention to any theory or mechanism, we believe that careful rational transfer of such compatible structural loops from selected donors may ensure preservation of the stereochemistry and surface topology of the antigen binding region. Also, we believe that preservation of interactions among the loops and between the loops and the proximal 13 strands may lead to molecules that have desirable biophysical and biochemical properties (e.g., stability, solubility, etc.). Compatible loops may also help to maintain affinity with the target (or improve affinity with the target). Variations in loop lengths may provide recognition with different types of antigen.

The donor molecule choice is generally due to the 3D architecture of the 13 sheets sandwich present in the domains of the donor molecule, which are generally similar to the 3D fold of the CH2 domain scaffold. A beta strand leads up to the L2 loop in the V domains of antibodies. The corresponding portion in a CH2 domain does not have the geometry and stereochemistry typical of a beta strand, but is closer to a random coil. Despite this difference, the overall dispositions of the three loops, namely L1, L2 and L3, are preserved in the donor database molecules and the CH2 domains. The donor molecules may be obtained from a database of crystal structures or molecules, for example a database of crystal structures of Ig-like molecules, or a database of crystal structures of V-like domains of immunogbulin and related molecules (e.g., from IMGT, Kaas et al., 2004). However the donor molecules are not limited to V-like domains of immunoglobulin and related molecules. Any other peptide, not necessarily one of a V-like domain, may be contemplated for transfer onto the CH2 scaffold. The present invention is not limited to human molecules. For example, donor molecules and/or donor loops may be conceivably obtained from any other organism.

The V-domain generally corresponds to the crystal structure of the V-J region or V-D-J region of the immunoglobulin or T cell receptor chain. This single V-domain is designated (Lefranc, et al., 2003) as: VH (V-domain of an Ig-Heavy chain), VL (V-domain of an Ig-Light chain), V-kappa (V-domain of an Ig-Light-Kappa chain), V-lambda (V-domain of an Ig-Light-Lambda chain), V-alpha (V-domain of a TcR-Alpha chain), V-beta (V-domain of a TcR-Beta chain), V-gamma (V-domain of a TcR-Gamma chain), and V-delta (V-domain of a TcR-Delta chain). A V-like domain may correspond to a domain of similar 3D structure (beta-sandwich framework with CDR-like loops) as the V-domain for proteins other than immunoglobulin or T cell receptor chain.

Donor and Acceptor Criteria

Similarity and classification of domains for the donor database are described in Lefranc et al. (Lefranc, M-P. et al., Dev. Comp. Immunol., 27, 55-77, 2003) and they are based on alignment of more than 5000 sequences, definition of frameworks, and CDR loops, structural data from X-ray crystallography and characterization of hyper-variable loops. The assignment of favorable structural regions within the CH2 domain for interaction with targets is guided by the location of the 2 cysteines and X-ray crystallography of this domain (Prabakaran, P., Vu, B. K., Gan, J., Feng, Y, Dimitrov, D. S. and Ji, X. Acta Cryst, Sec D, 64, 1062-1067, 2008). Such regions are based on the objective criteria that backbone torsional angles are outside the ranges of phi between −110° and −140° and psi between 110° and 140° together with solvent accessible surface areas for residues to be more than 25 Å². A consecutive set of amino acids satisfying these criteria can have a tolerance of one amino acid that may not satisfy all the criteria.

The donor loop may be a corresponding loop or a loop from a different position in the donor protein. For example, in some embodiments, the L1 loop in the CH2 domain scaffold is replaced with a donor L1 loop. Or, in some embodiments, the L1 loop in the CH2 domain scaffold is replaced with a donor L3 loop, or the L1 loop in the CH2 domain scaffold is replaced with a donor L2 loop. In other words, loops may be switched (e.g., L3 receives a donor L1 loop, L2 receives a donor L3 loop, L3 receives a donor L2 loop, L3 receives a donor L3 loop, L2 receives a donor L1 loop, L2 receives a donor L2 loop, etc.)

Conventionally, the term "CDR" refers to Complementarity Determining Regions and the amino acid residues in a particular CDR were assigned using sequence-based methods first proposed by Kabat and coworkers (Kabat, et. al., 1991, Sequences of Proteins of Immunological Interest, National Institutes of Health Publication No. 91-3242, 5th ed., United States Department of Health and Human Services, Bethesda, Md.). Since 3D structural information is not used in this method, a portion of what is actually structural framework is assigned as CDR loop. Alternately, these antigen recognition regions have been defined as "hyper-variable loops" by Chothia and coworkers (Chothia C, Lesk AM. 1987. J. Mol. Biol. 196: 901-917; Al-Lazikani B, Lesk A M, Chothia C. 1997. J. Mol. Biol. 273: 927-948) using information obtained from observations on crystal structures. This method of delineating framework from hyper-variable regions is also not perfect and as a result antigens are recognized by amino acid residues at sites beyond the borders of regions defined as hyper-variable loops. The Raghunathan method (Raghunathan, G., U.S. Patent Application No. 2009/0118127 Methods for use in Human-Adapting monoclonal antibodies) used in this invention uses a combination of Kabat's CDR and Chothia's hyper-variable loop definitions to define regions of the immunoglobulin structure that contain antibody binding residues.

The L1, L2, and L3 loops of the CH2 domain of IgG1 may be defined as follows: the L1 loop is the amino acid sequence DVSHEDPEVK (27-38) (SEQ ID NO: 2), the L2 loop is the sequence EEQYNS (SEQ ID NO: 4) (84, 84.1-84.4, 85.4) or QYNS (SEQ ID NO: 139) (84.2-84.2, 85.4), and the L3 loop is the sequence SNKALAPI (107-117) (SEQ ID NO: 3). Two loop sizes are used for L2 to account for the ambiguity in defining this loop. The numbers in parentheses refer to IMGT numbers. In these loop definitions the L1 loop has a length of 10 amino acids, the L2 loop has a length of 6 amino acids and 4 amino acids, and the L3 loop has a length of 9 amino acids. This differs slightly from the IMGT definition, for example. The present invention is not limited to the aforementioned loop definitions. The CH2 domain scaffold does not have the characteristic beginning and ending sequence patterns that are used traditionally for delineating loops in an antibody variable region domain. However, the positions of the two cysteines are conserved and align well with the donor domains. When the aforementioned structural and conformational criteria based on the crystal structure of the CH2 domain are used to define the loop regions targeted for transfer, it is noted that the loops defined by the structural approach differ from the loops identified by sequence-based definition. In other words, loops defined by the donor criteria of this invention do not coincide with loops that would be defined by CDR-defining criteria. The loops, whether derived for the CH2 domain scaffold or from the donor molecule may singly or in combination form an antigen binding region.

The present invention is not limited to using the exact donor loops obtained from the donor molecules. Loop lengths of donor loops may be generally similar to the loop it replaces or similar to the loop from its donor. However, longer loops (or shorter loops) may be generated in order to have flexibility to recognize different types of antigens. For example, long loops are observed for the third loop of the heavy chain (H3) of antibodies for some antigens, such as HIV-1 protease and also in the antibodies of some species such as camel, llama and shark. Also, long L1 loops have been observed in some antibodies. Such unusually long loops have been found to be necessary to create variations in shapes of the antibody combining site. It has been observed (Raqhunathan, G., Smart, J., Williams, J and Almagro, J. C. J. Mol. Recog. 2012 (in press)) that a flat antibody surface is often optimal for recognizing protein antigens while surfaces with crevices may be necessary for recognizing haptens, which are much smaller.

In some embodiments the donor loop (the loop that replaces the loop of the CH2 domain scaffold) comprises an amino acid addition or deletion (e.g., the donor loop has increased or decreased amino acids). In some embodiments, the donor L1 loop has between 5 and 24 amino acids. For example, the donor L1 loop may have 5 amino acids, 6 amino acids, 7 amino acids, 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, 20 amino acids, 21 amino acids, 22 amino acids, 23 amino acids, or 24 amino acids. In some embodiments, the donor L2 loop has between 3 to 10 amino acids. For example, the donor L2 loop may have 3 amino acids, 4 amino acids, 5 amino acids, 6 amino acids, 7 amino acids, 8 amino acids, 9 amino acids, or 10 amino acids.

In some embodiments, the donor L3 loop has between 3 and 24 amino acids. For example, the donor L3 loop may have 3 amino acids, 4 amino acids, 5 amino acids, 6 amino acids, 7 amino acids, 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, 20 amino acids, 21 amino acids, 22 amino acids, 23 amino acids, or 24 amino acids.

In some embodiments, the donor L1 loop has 10 amino acids and the donor L3 loop has between 7 and 10 amino acids (e.g., 7 amino acids, 8 amino acids, 9 amino acids, 10 amino acids). In some embodiments, the donor L1 loop has 10 amino acids and the donor L3 loop has between 8 and 12 amino acids (e.g., 8 amino acids, 9 amino acids, 10 amino acids, 11 amino acids, 12 amino acids). In some embodiments, the donor L1 loop has 10 amino acids and the donor L3 loop has between 12 and 24 amino acids (e.g., 12 amino acids, 13 amino acids, 14 amino acids, 15 amino acids, 16 amino acids, 17 amino acids, 18 amino acids, 19 amino acids, 20 amino acids, 21 amino acids, 22 amino acids, 23 amino acids, 24 amino acids).

In some embodiments, the donor L1 loop has 9 amino acids and the donor L3 loop has between 8 and 12 amino acids (e.g., 8 amino acids, 9 amino acids, 10 amino acids, 11 amino acids, 12 amino acids). In some embodiments, the donor L1 loop has 9 amino acids and the donor L3 loop has between 12 and 24 amino acids (e.g., 12 amino acids, 13 amino acids, 14 amino acids, 15 amino acids, 16 amino acids, 17 amino acids, 18 amino acids, 19 amino acids, 20 amino acids, 21 amino acids, 22 amino acids, 23 amino acids, 24 amino acids).

In some embodiments, the donor L3 loop has 10 amino acids and the donor L1 loop has between 7 and 10 amino acids (e.g., 7 amino acids, 8 amino acids, 9 amino acids, 10 amino acids). In some embodiments, the donor L3 loop has 10 amino acids and the donor L1 loop has between 8 and 12 amino acids (e.g., 8 amino acids, 9 amino acids, 10 amino acids, 11 amino acids, 12 amino acids). In some embodiments, the donor L3 loop has 10 amino acids and the donor L1 loop has between 12 and 24 amino acids (e.g., 12 amino acids, 13 amino acids, 14 amino acids, 15 amino acids, 16 amino acids, 17 amino acids, 18 amino acids, 19 amino acids, 20 amino acids, 21 amino acids, 22 amino acids, 23 amino acids, 24 amino acids).

In some embodiments, the donor L3 loop has 9 amino acids and the donor L1 loop has between 8 and 12 amino acids (e.g., 8 amino acids, 9 amino acids, 10 amino acids, 11 amino acids, 12 amino acids). In some embodiments, the donor L3 loop has 9 amino acids and the donor L1 loop has between 12 and 24 amino acids (e.g., 12 amino acids, 13 amino acids, 14 amino acids, 15 amino acids, 16 amino acids, 17 amino acids, 18 amino acids, 19 amino acids, 20 amino acids, 21 amino acids, 22 amino acids, 23 amino acids, 24 amino acids).

The present invention is not limited to the aforementioned loop lengths or combinations of loop lengths.

Table 2 shows non-limiting examples of sequences for loops L1, L2, and L3, and also provides the National Center for Biological Information (NCBI) Protein Database (pdb) code for the donor molecule (e.g., the donor crystal structure of the V-like domain). Examples 1-6 have L2 loops obtained from donors (e.g., L2=2, 3, 4, 5, 6, 7, 8) and L1 and L3 loops are from the CH2 domain scaffold. Examples 7-12 have L1 and L3 obtained from donors (e.g., L1=10, L3=7, 8, 9, 10), and L2 loops are from the CH2 domain scaffold. Examples 13-18 have L1 and L3 obtained from donors (e.g., L1=9, L3=8, 9, 11, 12), and L2 loops are from the CH2 domain scaffold. Examples 19-26 have long L3 loops. L1 and L3 loops are obtained from donors (e.g., L1=10, L3=12, 13, 14, 15, 16, 17, 18, 24). L2 loops are from the CH2 domain scaffold. Examples 27-34 have long L1 loops. L1 and L3 loops are obtained from donors (e.g., L1=10, L3=12, 13, 14, 15, 16, 17, 18, 24) wherein the L1 and L3 loops are switched (e.g., the donor L3 loop replaces the L1 loop of the CH2 domain scaffold and the donor L1 loop replaces the L3 loop of the CH2 domain scaffold). L2 loops are from the CH2 domain scaffold. Example 35 has the L1 and L3 interchanged in the native CH2 molecule.

TABLE 2

| Example | CH2 Graft Mol Id | L1 Sequence | L2 Sequence | L3 Sequence | Donor pdb code |
|---|---|---|---|---|---|
| 1 | CT-2-2456 | DVSHEDPEVK (SEQ ID NO: 2) | EEHN (SEQ ID NO: 5) | SNKALPAPI (SEQ ID NO: 3) | 7fab_L |
| 2 | CT-2-2022 | DVSHEDPEVK (SEQ ID NO: 2) | EEAAS (SEQ ID NO: 6) | SNKALPAPI (SEQ ID NO: 3) | 3e8u_L |
| 3 | CT-2-1329 | DVSHEDPEVK (SEQ ID NO: 2) | EEYDTS (SEQ ID NO: 7) | SNKALPAPI (SEQ ID NO: 3) | 2fec_L |
| 4 | CT-2-1617 | DVSHEDPEVK (SEQ ID NO: 2) | VYPGSI (SEQ ID NO: 8) | SNKALPAPI (SEQ ID NO: 3) | 2ojz_H |
| 5 | CT-2-1557 | DVSHEDPEVK (SEQ ID NO: 2) | IYWDDDK (SEQ ID NO: 9) | SNKALPAPI (SEQ ID NO: 3) | 2j88_H |
| 6 | CT-2-2117 | DVSHEDPEVK (SEQ ID NO: 2) | ISSSGDPT (SEQ ID NO: 10) | SNKALPAPI (SEQ ID NO: 3) | 3fzu_C |
| 7 | CT-1-3-321 | GFSLSTYGMG (SEQ ID NO: 11) | EEQYNS (SEQ ID NO: 4) | VQEGYIY (SEQ ID NO: 35) | 1ggi_H |
| 8 | CT-1-3-1999 | KSVSTSGYSY (SEQ ID NO: 12) | EEQYNS (SEQ ID NO: 4) | QHSRELLT (SEQ ID NO: 36) | 3dgg_A |
| 9 | CT-1-3-1557 | GFSLSTSGMG (SEQ ID NO: 13) | EEQYNS (SEQ ID NO: 4) | TLYYGSVDY (SEQ ID NO: 37) | 2j88_H |
| 10 | CT-1-3-2022 | QSVDYNGDSY (SEQ ID NO: 14) | EEQYNS (SEQ ID NO: 4) | QQSNEDPFT (SEQ ID NO: 38) | 3e8u_L |
| 11 | CT-1-3-1795 | GGSIRSGGYY (SEQ ID NO: 15) | EEQYNS (SEQ ID NO: 4) | ARLDGYTLDI (SEQ ID NO: 39) | 2vxq_H |

TABLE 2-continued

| Example | CH2 Graft Mol Id | L1 Sequence | L2 Sequence | L3 Sequence | Donor pdb code |
|---|---|---|---|---|---|
| 12 | CT-1-3-369 | KSVSTSGYNY (SEQ ID NO: 16) | EEQYNS (SEQ ID NO: 4) | LYSREFPPWT (SEQ ID NO: 40) | 1i7z_A |
| 13 | CT-1-3-71 | GYSITSDYA (SEQ ID NO: 17) | EEQYNS (SEQ ID NO: 4) | ARGWPLAY (SEQ ID NO: 41) | 1baf_H |
| 14 | CT-1-3-2167 | SRDVGGYNY (SEQ ID NO: 18) | EEQYNS (SEQ ID NO: 4) | WSFAGSYYV (SEQ ID NO: 42) | 3gje_A |
| 15 | CT-1-3-2132 | GYSITSDFA (SEQ ID NO: 19) | EEQYNS (SEQ ID NO: 4) | ATAGRGFPY (SEQ ID NO: 43) | 3g5z_B |
| 16 | CT-1-3-2194 | SSNIGAGYD (SEQ ID NO: 20) | EEQYNS (SEQ ID NO: 4) | QSYDSSLSGSV (SEQ ID NO: 44) | 3h42_L |
| 17 | CT-1-3-239 | GYSITSDYA (SEQ ID NO: 17) | EEQYNS (SEQ ID NO: 4) | ASYDDYTWFTY (SEQ ID NO: 45) | 1f8t_H |
| 18 | CT-1-3-1874 | GYSISSDYA (SEQ ID NO: 21) | EEQYNS (SEQ ID NO: 4) | ARGYYGSSHSPV (SEQ ID NO: 46) | 32c2_B |
| 19 | CT-1-3-2291 | GFSLSTSGMS (SEQ ID NO: 22) | EEQYNS (SEQ ID NO: 4) | ARRTTTADYFAY (SEQ ID NO: 27) | 3ifl_H |
| 20 | CT-1-3-2399 | GFSLSTYGVG (SEQ ID NO: 23) | EEQYNS (SEQ ID NO: 4) | ARLGSDYDVWFDY (SEQ ID NO: 28) | 3l5y_H |
| 21 | CT-1-3-451 | GFSLTTYGMG (SEQ ID NO: 24) | EEQYNS (SEQ ID NO: 4) | ARRAPFYGNHAMDY (SEQ ID NO: 47) | 1jrh_H |
| 22 | CT-1-3-2067 | GFSLSTSGMG (SEQ ID NO: 13) | EEQYNS (SEQ ID NO: 4) | VRRAHTTVLGDWFAY (SEQ ID NO: 30) | 3eys_H |
| 23 | CT-1-3-2425 | GFSLSTSGMS (SEQ ID NO: 22) | EEQYNS (SEQ ID NO: 4) | ARTLRVSGDYVRDFDL (SEQ ID NO: 31) | 3lzf_H |
| 24 | CT-1-3-1885 | GFSIRTSKVG (SEQ ID NO: 25) | EEQYNS (SEQ ID NO: 4) | ARRGFYGRKYEVNHFDY (SEQ ID NO: 32) | 3bae_H |
| 25 | CT-1-3-220 | GFSLSTSGMG (SEQ ID NO: 13) | EEQYNS (SEQ ID NO: 4) | ARRTFSYYYGSSFYYFDN (SEQ ID NO: 33) | 1etz_B |
| 26 | CT-1-3-1317 | GFSLSDFGVG (SEQ ID NO: 26) | EEQYNS (SEQ ID NO: 4) | AHRRGPTTLFGVPIARGPVNAMDV (SEQ ID NO: 34) | 2f5b_H |
| 27 | CT-3-1-2291 | ARRTTTADYFAY (SEQ ID NO: 27) | EEQYNS (SEQ ID NO: 4) | GFSLSTSGMS (SEQ ID NO: 22) | 3ifl_H |
| 28 | CT-3-1-2399 | ARLGSDYDVWFDY (SEQ ID NO: 28) | EEQYNS (SEQ ID NO: 4) | GFSLSTYGVG (SEQ ID NO: 23) | 3l5y_H |
| 29 | CT-3-1-451 | ARRAPFYGNHAMDY (SEQ ID NO: 29) | EEQYNS (SEQ ID NO: 4) | GFSLTTYGMG (SEQ ID NO: 24) | 1jrh_H |
| 30 | CT-3-1-2067 | VRRAHTTVLGDWFAY (SEQ ID NO: 30) | EEQYNS (SEQ ID NO: 4) | GFSLSTSGMG (SEQ ID NO: 13) | 3eys_H |

TABLE 2-continued

| Example | CH2 Graft Mol Id | L1 Sequence | L2 Sequence | L3 Sequence | Donor pdb code |
|---|---|---|---|---|---|
| 31 | CT-3-1-2425 | ARTLRVSGDYVRDFDL (SEQ ID NO: 31) | EEQYNS (SEQ ID NO: 4) | GFSLSTSGMS (SEQ ID NO: 22) | 3lzf_H |
| 32 | CT-3-1-1885 | ARRGFYGRKYEVNHFDY (SEQ ID NO: 32) | EEQYNS (SEQ ID NO: 4) | GFSIRTSKVG (SEQ ID NO: 25) | 3bae_H |
| 33 | CT-3-1-220 | ARRTFSYYYGSSFYYFDN (SEQ ID NO: 33) | EEQYNS (SEQ ID NO: 4) | GFSLSTSGMG (SEQ ID NO: 13) | 1etz_B |
| 34 | CT-3-1-1317 | AHRRGPTTLFGVPIARGPVNAMDV (SEQ ID NO: 34) | EEQYNS (SEQ ID NO: 4) | GFSLSDFGVG (SEQ ID NO: 26) | 2f5b_H |
| 35 | CT-3-2-1-CH2 | SNKALPAPI (SEQ ID NO: 3) | EEQYNS (SEQ ID NO: 4) | DVSHEDPEVK (SEQ ID NO: 2) | 3dg9_A |

The CH2 domain template molecule may have a molecular weight less than about 30 kDa. In some embodiments, the CH2 domain template molecule has a molecular weight less than about 20 kDa. In some embodiments, the CH2 domain template molecule has a molecular weight less than about 15 kDa.

The CH2 domain templates may be used to create a library. Methods of library construction are well known to one of ordinary skill in the art. The library of CH2 domain templates (comprising a variety of CH2 domain templates) may be used for a variety of purposes including but not limited to identification of a CH2 domain template or identification of an antibody binding region that binds to a specific target. The CH2 domain template molecule may effectively bind to a target antigen (or one or more target antigens). In some embodiments, the CH2 domain template molecule has a greater avidity and/or affinity for the target (or targets) as compared to the avidity and/or affinity of a CH2 domain scaffold or a comparable antibody.

In some embodiments, the CH2 domain template molecule is linked to an immunoconjugate, toxin, immunotoxin, a drug, an isotope, or an imaging agent. In some embodiments, the CH2 domain template molecule comprises a leader sequence.

Methods for producing antibodies and antibody fragments, for example the CH2 domain template molecules, and methods of DNA construction for such antibodies and antibody fragments, for example the CH2 domain template molecules, are well known to one of ordinary skill in the art. For example, the CH2 domain template molecules may be expressed in a bacterial system (e.g., including but not limited to *Escherichia coli*, a yeast system, a phage display system, an insect system, a mammalian system, a ribosomal display, a cis display system (Odegrip, R. et al., PNAS 101 (9): 2806-2810, 2004), the like, or a combination thereof. The present invention is in no way limited to the methods (e.g., protein expression and display systems) described herein.

The present invention includes herein all constructs and methods related to the constructing of CH2 domain template molecules (e.g., on the DNA level) as well as methods of constructing a library. The methods may, for example, comprise providing a DNA construct having a sequence corresponding to a CH2 domain scaffold of IgG, IgA, IgD, or a CH3 domain scaffold of IgE, or IgM, having a L1 loop, a L2 loop, and a L3 loop; and choosing any of (i) replacing a sequence corresponding to the L1 loop of the scaffold with a sequence corresponding to a donor L1 loop of a donor molecule, the donor molecule further comprising a donor L2 loop and a donor L3 loop, wherein the donor L2 loop of the donor molecule has a first amino acid length and the donor L3 loop of the donor molecule has a second amino acid length, the first amino acid length closely matching an amino acid length of the L2 loop of the scaffold and the second length closely matching an amino acid length of the L3 loop of the scaffold; (ii) replacing a sequence corresponding to the L2 loop of the scaffold with a sequence corresponding to a donor L2 loop of a donor molecule, the donor molecule further comprising a donor L1 loop and a donor L3 loop, wherein the donor L1 loop of the donor molecule has a first length and the donor L3 loop of the donor molecule has a second length, the first length closely matching a length of the L1 loop of the scaffold and the second length closely matching a length of the L3 loop of the scaffold; (iii) replacing a sequence corresponding to the L3 loop of the scaffold with a sequence corresponding to a donor L3 loop of a donor molecule, the donor molecule further comprising a donor L1 loop and a donor L2 loop, wherein the donor L1 loop of the donor molecule has a first length and the donor L2 loop of the donor molecule has a second length, the first length closely matching a length of the L1 loop of the scaffold and the second length closely matching a length of the L2 loop of the scaffold; (iv) replacing a sequence corresponding to the L1 loop and a sequence corresponding to the L2 loop of the scaffold with either (a) a sequence corresponding to a donor L1 loop and a sequence corresponding to a donor L2 loop of a donor molecule, respectively, or (b) a sequence corresponding to a donor L2 loop and a sequence corresponding to a donor L2 loop of a donor molecule, respectively, wherein the donor molecule further comprises a donor L3 loop having a first length, the first length closely matching a length of the L3 loop of the scaffold; (v) replacing a sequence corresponding to the L1 loop and a sequence corresponding to the L3 loop of the scaffold with either (a) a sequence corresponding to a donor L1 loop and a sequence corresponding to a donor L3 loop of a donor molecule, respectively, or (b) a sequence corresponding to a donor L3 loop and a sequence corresponding to a donor L1 loop of a donor molecule, respectively, wherein the donor molecule further comprises a donor L2 loop having a first length, the first length closely matching a length of the L2 loop of the scaffold; (vi) replacing a sequence corresponding to the L2 loop and a sequence corresponding to the L3 loop of the scaffold with either (a) a sequence corresponding to a donor L2 loop and a sequence corresponding to a donor L3 loop of a donor molecule, respectively, or (b) a sequence corresponding to a donor L3 loop and a sequence corresponding to a donor L2 loop of a donor molecule, respectively, wherein the donor molecule further comprises a donor L1 loop having a first length, the first length closely matching a length of the L1 loop of the scaffold; or (vii) replacing a sequence corresponding to the L1 loop, a sequence corresponding to the L2 loop, and a sequence corresponding to the L3 loop of the scaffold with either (a) a sequence corresponding to a donor L1 loop, a sequence corresponding to a donor L2 loop, and a sequence corresponding to a donor L3 loop, respectively; (b) a sequence corresponding to a donor L1 loop, a sequence corresponding to a donor L3 loop, and a sequence corresponding to a donor L2 loop, respectively; (c) a sequence corresponding to a donor L2 loop, a sequence corresponding to a donor L1 loop, and a sequence corresponding to a donor L3 loop, respectively; (d) a sequence corresponding to a donor L2 loop, a sequence corresponding to a donor L3 loop, and a sequence corresponding to a donor L1 loop, respectively; (e) a sequence corresponding to a donor L3 loop, a sequence corresponding to a donor L1 loop, and a sequence corresponding to a donor L2 loop, respectively; or (f) a sequence corresponding to a donor L3 loop, a sequence corresponding to a donor L2 loop, and a sequence corresponding to a donor L1 loop, respectively. The aforementioned steps may be repeated as necessary to create a library of CH2 domain template molecules.

In some embodiments, after the initial steps are taken to create a CH2 domain template molecule, the template molecule may be evaluated for certain properties. In some embodiments, the template molecule is further modified to provide enhancements to the molecule, for example stability, target specificity, etc.

In some embodiments, the CH2 domain templates are multimers of individual CH2 domain templates. For example, the CH2 domain template may comprise two individual CH2 domain templates (e.g., a dimer). In some embodiments, the CH2 domain template comprises three CH2 domain templates, four CH2 domain templates, or more than four CH2 domain templates. The individual CH2 domain templates may be linked via linkers, for example.

Disulfide Bonds

Each domain in an immunoglobulin has a conserved structure referred to as the immunoglobulin fold. The immunoglobulin fold comprises two beta sheets arranged in a compressed anti-parallel beta barrel. With respect to constant domains, the immunoglobulin fold comprises a 3-stranded sheet containing strands C, F, and G, packed against a 4-stranded sheet containing strands A, B, D, and E. The strands are connected by loops. The fold is stabilized by hydrogen bonding, by hydrophobic interactions, and by a disulfide bond. Disulfide bonds are known to provide a level of stability to the peptide, and in some cases additional disulfide bonds confer additional stability. In some embodiments, the CH2 domain template molecule (or CH2 domain scaffold with donor loop(s) incorporated) comprises one or more additional disulfide bonds. Table 3 describes non-limiting examples of CH2 domain scaffolds with additional disulfide bonds (e.g., V240 to C240 and I332 to C332; S239 to C239 and I332 to C332; P244 to C244 and I336 to C336; L242 to C242 and K334 to C334; and V240 to C240 and K334 to C334). While these disulfide bonds are engineered based on structural considerations, substitutions at positions whose C-alpha is up to about 5.3 angstroms from these selected positions might also favor disulfide bonds. The new cysteine residues in Table 3 are boxed for reference.

In some embodiments, additional disulfide bonds can be added in sites adjacent to the aforementioned disulfide bond sites (or other disulfide bond sites), when the disulfide bond sites are situated in the loop region (e.g., versus the beta sheet portion). In some embodiments, additional disulfide bonds are incorporated into the molecule by adding amino acids (versus substituting amino acids as previously described).

TABLE 3

| Example | CH2 domain sequences (residues 231-342) with additional disulfide bonds: | | | | | |
|---|---|---|---|---|---|---|
| 1<br>(V240 → C<br>and I332 →<br>C)<br>(SEQ ID NO: 48) | 2<br>3<br>1234567890<br>APELLGGPS[C] | 2<br>4<br>1234567890<br>FLFPPKPKDT | 2<br>5<br>1234567890<br>LMISRTPEVT | 2<br>6<br>1234567890<br>CVVVDVSHED | 2<br>7<br>1234567890<br>PEVKFNWYVD | 2<br>8<br>1234567890<br>GVEVHNAKTK |
| | 2<br>9<br>1234567890<br>PREEQYNSTY | 3<br>0<br>1234567890<br>RVVSVLTVLH | 3<br>1<br>1234567890<br>QDWLNGKEYK | 3<br>2<br>1234567890<br>CKVSNKALPA | 3<br>3<br>1234567890<br>P[C]EKTISKAK | 3<br>4<br>12<br>GQ |
| 2<br>(S239 → C<br>and I332 →<br>C)<br>(SEQ ID NO: 49) | 2<br>3<br>1234567890<br>APELLGGP[C]V | 2<br>4<br>1234567890<br>FLFPPKPKDT | 2<br>5<br>1234567890<br>LMISRTPEVT | 2<br>6<br>1234567890<br>CVVVDVSHED | 2<br>7<br>1234567890<br>PEVKFNWYVD | 2<br>8<br>1234567890<br>GVEVHNAKTK |
| | 2<br>9<br>1234567890<br>PREEQYNSTY | 3<br>0<br>1234567890<br>RVVSVLTVLH | 3<br>1<br>1234567890<br>QDWLNGKEYK | 3<br>2<br>1234567890<br>CKVSNKALPA | 3<br>3<br>1234567890<br>P[C]EKTISKAK | 3<br>4<br>12<br>GQ |

TABLE 3-continued

| Example | CH2 domain sequences (residues 231-342) with additional disulfide bonds: |
|---|---|
| 3<br>(P244 → C<br>and I336 →<br>C)<br>(SEQ ID NO:<br>50) |       2            2            2            2            2            2<br>      3            4            5            6            7            8<br>1234567890 1234567890 1234567890 1234567890 1234567890 1234567890<br>APELLGGPSV FLF[C]PKPKDT LMISRTPEVT CVVVDVSHED PEVKFNWYVD GVEVHNAKTK<br><br>      2            3            3            3            3            3<br>      9            0            1            2            3            4<br>1234567890 1234567890 1234567890 1234567890 1234567890 12<br>PREEQYNSTV RVVSVLTVLH QDWLNGKEYK CKVSNKALPA PIEKT[C]SKAK GQ |
| 4<br>(L242 → C<br>and K334 →<br>C)<br>(SEQ ID NO:<br>51) |       2            2            2            2            2            2<br>      3            4            5            6            7            8<br>1234567890 1234567890 1234567890 1234567890 1234567890 1234567890<br>APELLGGPSV F[C]FPPKPKDT LMISRTPEVT CVVVDVSHED PEVKFNWYVD GVEVHNAKTK<br><br>      2            3            3            3            3            3<br>      9            0            1            2            3            4<br>1234567890 1234567890 1234567890 1234567890 1234567890 12<br>PREEQYNSTY RVVSVLTVLH QDWLNGKEYK CKVSNKALPA PIE[C]TISKAK GQ |
| 5<br>(V240 → C<br>and K334 →<br>C)<br>(SEQ ID NO:<br>52) |       2            2            2            2            2            2<br>      3            4            5            6            7            8<br>1234567890 1234567890 1234567890 1234567890 1234567890 1234567890<br>APELLGGPS[C] FLFPPKPKDT LMISRTPEVT CVVVDVSHED PEVKFNWYVD GVEVHNAKTK<br><br>      2            3            3            3            3            3<br>      9            0            1            2            3            4<br>1234567890 1234567890 1234567890 1234567890 1234567890 12<br>PREEQYNSTY RVVSVLTVLH QDWLNGKEYK CKVSNKALPA P[I]ECTISKAK GQ |

The disulfide bond may be engineered to flank (or even include one end of) the L2 loop (the recipient/final grafted L2 loop). This may create additional stability for the loop (e.g., like a staple). Table 4 shows an example of a L2 loop with an additional disulfide bond wherein both residue E293 and residue R301 have been changed to cysteines (C). The new cysteine residues in Table 4 are boxed for reference. In some embodiments, the disulfide bond may be positioned at the base of the loop.

TABLE 4

| Example | CH2 domain sequence (residues 231-342) with additional disulfide bonds to constrain loop L2: |
|---|---|
| 1<br>(E293 → C<br>and R301 →<br>C)<br>(SEQ ID NO:<br>53) |       2            2            2            2            2            2<br>      3            4            5            6            7            8<br>1234567890 1234567890 1234567890 1234567890 1234567890 1234567890<br>APELLGGPSV FLFPPKPKDT LMISRTPEVT CVVVDVSHED PEVKFNWYVD GVEVHNAKTK<br><br>      2            3            3            3            3            3<br>      9            0            1            2            3            4<br>1234567890 1234567890 1234567890 1234567890 1234567890 12<br>PR[C]EQYNSTY [C]VVSVLTVLH QDWLNGKEYK CKVSNKALPA PIEKTISKAK GQ |

In some embodiments, the disulfide bonds (one or more) of the CH2 domain scaffold have been moved (relocated, for example) to create the CH2 domain template molecule.
Modifications One or more loops and/or strands (of the beta sheets, A, B, C, D, E, F, G) of one or more CH2 domain scaffolds or donor loops (or CH2 domain template molecules) may be modified. As used herein, the term "modified" or "modification," can include one or more mutations, deletions, additions, substitutions, physical alteration (e.g., cross-linking modification, covalent bonding of a component, post-translational modification, e.g., acetylation, glycosylation, tagging, e.g., His-tags, the like, or a combination thereof), the like, or a combination thereof. Modification, e.g., mutation, is not limited to random modification (e.g., random mutagenesis) but includes rational design as well.

The CH2 domain scaffold (or CH2 domain template molecule) may comprise truncations/deletions, e.g., deletions of portions of the N-terminus and/or portions of the C-terminus. In some embodiments, the truncation/deletion may be between about 1 to 10 amino acids, for example the truncation is a one amino acid truncation, a two amino acid truncation, a three amino acid truncation, a four amino acid truncation, a five amino acid truncation, a six amino acid truncation, a seven amino acid truncation, an eight amino acid truncation, a nine amino acid truncation, a ten amino acid truncation, etc.

In some embodiments, the CH2 domain scaffold (or CH2 domain template molecule) comprises a truncation or deletion of the first seven amino acids of the N-terminus. Or, in some embodiments, the CH2 domain scaffold (or CH2 domain template molecule) comprises a deletion of the first amino acid, the first two, the first three, the first four, the first five, the first six, or the first seven amino acids of the N-terminus. In some embodiments, the CH2 domain scaffold (or CH2 domain template molecule) comprises a deletion of the first eight, the first nine, or the first ten amino acids of the N-terminus. In some embodiments, the CH2 domain scaffold (or CH2 domain template molecule) comprises a deletion of the last four amino acids of the C-terminus. In some embodiments, the CH2 domain scaffold scaffold (or CH2 domain template molecule) comprises a deletion of the last amino acid, the last two, the last three, the last four, the last five, the last six, the last seven, the last eight, the last nine, or the last ten amino acids of the C-terminus. In some embodiments, the CH2 domain scaffold (or CH2 domain template molecule) comprises a deletion at both the N-terminus and the C-terminus. For example, in some embodiments, the CH2 domain scaffold (or CH2 domain template molecule) comprises a deletion of the first amino acid, the first two, the first three, the first four, the first five, the first six, or the first seven amino acids of the N-terminus and a deletion of the last amino acid, the last two, the last three, the last four, the last five, the last six, the last seven, the last eight, the last nine, or the last ten amino acids of the C-terminus. The present invention is not limited to the aforementioned examples of deletions. The CH2 domain scaffold (or CH2 domain template molecule) may comprise other deletions in other regions of the protein. Without wishing to limit the present invention to any theory or mechanism, it is believed that such truncations or deletions (or other modifications) to the molecule may confer a particular property, for example including but not limited to enhanced stability.

The CH2 domain scaffold (or CH2 domain template molecule) may comprise additions, e.g., additions of amino acids on the N-terminus and/or on the C-terminus. In some embodiments, the addition may be between about 1 to 10 amino acids, for example the addition is a one amino acid addition, a two amino acid addition, a three amino acid addition, a four amino acid addition, a five amino acid addition, a six amino acid addition, a seven amino acid addition, an eight amino acid addition, a nine amino acid addition, a ten amino acid addition, an eleven amino acid addition, a twelve amino acid addition, etc.

In some embodiments, the CH2 domain scaffold (or CH2 domain template molecule) comprises a one amino acid addition, a two amino acid addition, a three amino acid addition, a four amino acid addition, a five amino acid addition, a six amino acid addition, a seven amino acid addition, an eight amino acid addition, a nine amino acid addition, a ten amino acid addition, an eleven amino acid addition, a twelve amino acid addition, etc. on the N-terminus. In some embodiments, the CH2 domain scaffold (or CH2 domain template molecule) comprises a one amino acid addition, a two amino acid addition, a three amino acid addition, a four amino acid addition, a five amino acid addition, a six amino acid addition, a seven amino acid addition, an eight amino acid addition, a nine amino acid addition, a ten amino acid addition, an eleven amino acid addition, a twelve amino acid addition, etc. on the C-terminus. In some embodiments, the CH2 domain scaffold (or CH2 domain template molecule) comprises an addition on the N-terminus and on the C-terminus. For example, the CH2 domain scaffold (or CH2 domain template molecule) may comprise a one amino acid addition, a two amino acid addition, a three amino acid addition, a four amino acid addition, a five amino acid addition, a six amino acid addition, a seven amino acid addition, an eight amino acid addition, a nine amino acid addition, a ten amino acid addition, an eleven amino acid addition, a twelve amino acid addition, etc. on the N-terminus and a one amino acid addition, a two amino acid addition, a three amino acid addition, a four amino acid addition, a five amino acid addition, a six amino acid addition, a seven amino acid addition, an eight amino acid addition, a nine amino acid addition, a ten amino acid addition, an eleven amino acid addition, a twelve amino acid addition, etc. on the C-terminus, One or more portions of the CH2 domain scaffold (or CH2 domain template molecule) or one or more amino acids may be substituted with another peptide or amino acid, respectively. For example, in some embodiments, the CH2 domain scaffold (or CH2 domain template molecule) comprises a first amino acid substitution. In some embodiments, the CH2 domain scaffold (or CH2 domain template molecule) comprises a first amino acid substitution and a second amino acid substitution. In some embodiments, the CH2 domain scaffold (or CH2 domain template molecule) comprises a first amino acid substitution, a second amino acid substitution, and a third amino acid substitution. In some embodiments, the CH2 domain scaffold (or CH2 domain template molecule) comprises more than three amino acid substitutions. Examples of amino acid substitutions may include but are not limited to M252Y, S254T, T256E, T307A, or a combination thereof. Without wishing to limit the present invention to any theory or mechanism, it is believed that one or more of the substitutions M252Y, S254T, T256E, T307A may increase serum half life of the molecule (e.g., increase FcRn binding).

In some embodiments, the CH2 domain scaffold or template molecule comprises a tag, for example including but not limited to a His tag (e.g., the CH2 domain template molecule found in Table 3, Example 4 may be comprise a His tag, e.g., "His-m01s", a template molecule GSGS (SEQ ID NO:140)-hinge6-CH2 may comprise a His tag, e.g., "His tag-GSGS (SEQ ID NO:140)-hinge6-CH2", etc.).

Serum Half-Life and Effector Molecule Binding Serum half-life of an immunoglobulin is mediated by the binding of the $F_c$ region to the neonatal receptor FcRn. The alpha domain is the portion of FcRn that interacts with the CH2 domain (and possibly CH3 domain) of IgG, and possibly with IgA, and IgD or with the CH3 domain (and possibly CH4 domain) of IgM and IgE. Several studies support a correlation between the affinity for FcRn binding and the serum half-life of an immunoglobulin.

In some embodiments, the CH2 domain template molecule has a similar or greater half-life in media (e.g., serum) as compared to the half-life of its CH2 domain scaffold. For example, the half-life in media of the CH2 domain template molecule is within about 20% of that of its CH2 domain scaffold. In some embodiments, the half-life in media of the CH2 domain template molecule is greater than that of its CH2 domain scaffold, for example between about 1 to 10% greater, between about 10 to 20% greater, between about 20 to 30% greater, between about 30 to 40% greater, between about 40 to 50% greater, between about 50 to 60% greater, between about 60 to 70% greater, between about 70 to 80% greater, between about 80 to 90% greater, between about 90 to 100% greater, or more than 100% greater.

Modifications may be made to the CH2 domain template molecule to modify (e.g., increase or decrease) the affinity and/or avidity the immunoglobulin has for FcRn (see, for example, U.S. Patent Application No. 2007/0135620). Modifications may include mutations (amino acid substitutions, deletions, physical modifications to amino acids) of one or more amino acid residues in one or more of the CH2 domains. Modifications may also include insertion of one or more amino acid residues or one or more binding sites (e.g., insertion of additional binding sites for FcRn). A modification may, for example, increase the affinity for FcRn at a lower pH (or higher pH). The present invention is not limited to the aforementioned modifications.

In some embodiments, the CH2 domain template molecule comprises at least one binding site for FcRn (e.g., wild type, modified, etc.). In some embodiments, the CH2 domain template molecule comprises at least two binding sites for FcRn (e.g., wild type, modified, etc.). In some embodiments, the CH2 domain template molecule comprises three or more binding sites for FcRn. None, one, or more of the binding sites for FcRn may be modified. In some embodiments, the CH2 domain template molecule comprises no binding sites for FcRn (e.g., no functional binding sites). In some embodiments, the CH2 domain template molecule comprises no binding sites for complement (e.g., no functional binding sites for complement). In some embodiments, the CH2 domain template molecule comprises one or more binding sites for complement (e.g., one binding site, two binding sites, three binding sites, etc.). In some embodiments, the CH2 domain template molecule comprises no binding sites for $F_c\gamma$ receptors (e.g., no functional binding sites). In some embodiments, the CH2 domain template molecule comprises one or more binding sites for $F_c\gamma$ receptors (e.g., one binding site, two binding sites, three binding sites, etc.).

$F_c$ receptors are receptors found on certain immune system cells, for example phagocytes (e.g., macrophages), natural killer cells, neutrophils, and mast cells. $F_c$ receptor activation can cause phagocytic or cytotoxic cells to destroy the target antigen bound to the antibody's paratope. $F_c$ receptors are classified based on the isotype of antibody they recognize. For example, $F_c\gamma$ receptors bind IgG, $F_c\alpha$ receptors bind IgA, $F_c\delta$ receptors bind IgD, $F_c\epsilon$ receptors bind IgE, and $F_c\mu$ receptors bind IgM. While all of the aforementioned $F_c$ receptors (excluding FcRn) are involved in immune responses, a subset of the $F_c\gamma$ receptors is considered to be the most potent pro-inflammatory receptors. In the case of $F_c\gamma$ receptors, receptor activation leads to activation of signalling cascades via motifs, for example an immunoreceptor tyrosine-based activation motif (ITAM), which causes activation of various other kinase reaction cascades depending on the cell type. Certain $F_c\gamma$ receptors antagonize the signalling of the pro-inflammatory $F_c\gamma$ receptors, and these anti-inflammatory receptors typically are linked to immunoreceptor tyrosine-based inhibition motif (ITIM) (see, for example Ravetch et al., (2000) Science 290:84-89).

Without wishing to limit the present invention to any theory or mechanism, it is believed that the CH2 domains of IgG, IgA, and IgD (or the equivalent CH3 domain of IgM and IgE) are responsible for all or most of the interaction with $F_c$ receptors (e.g., $F_c\gamma$, $F_c\alpha$, $F_c\delta$, $F_c\epsilon$, $F_c\mu$). In some embodiments, it may be useful to limit the ability of the CH2 domain template molecule to functionally bind $F_c$ receptors (e.g., pro-inflammatory $F_c\gamma$, $F_c\alpha$, $F_c\delta$, $F_c\epsilon$, $F_c\mu$), for example to help prevent adverse immune response effects. In such cases, retaining only one functional binding interaction with a particular pro-inflammatory $F_c$ receptor will confer properties most analogous to those of a native immunoglobulin. In contrast, in some embodiments it may be useful to enhance the ability of the CH2 domain template molecule to functionally bind $F_c$ receptors ($F_c\gamma$, $F_c\alpha$, $F_c\delta$, $F_c\epsilon$, $F_c\mu$), for example if one wishes to perform research experiments to study $F_c$ receptors. In another example, one may target a specific Fc receptor to either agonize or antagonize that receptor.

While construction of the template molecule may cause loss of FcR binding (e.g., FcγR binding) and/or complement binding, template molecules may be engineered to incorporate FcR and/or complement binding. For example, in some embodiments, the CH2 domain template molecule comprises no more than one functional binding site able to activate pro-inflammatory FcγR. In some embodiments, the term "functional $F_c$ receptor-binding region" refers to the ability of the binding of the $F_c$ receptor-binding region to the $F_c$ receptor to cause activation of a signalling cascade, for example via an ITAM. In some embodiments, a "non-functional $F_c$ receptor-binding region" may refer to an $F_c$ receptor-binding region that cannot bind to the $F_c$ receptor (or cannot completely bind), or to a $F_c$ receptor-binding region that can bind to the $F_c$ receptor but cannot cause activation of a signalling cascade (e.g., via an ITAM). In some embodiments, the CH2 domain template molecule does not have a functional $F_c$ receptor-binding region for binding to a target $F_c$ receptor to effectively activate an immune response.

The CH2 domains of IgG, IgA, and IgD (or the equivalent CH3 domain of IgM and IgE) also have binding sites for complement. In some embodiments, it may be useful to limit the ability of the CH2 domain template molecule to activate a complement cascade, for example to help prevent adverse immune response effects for reasons analogous to those discussed above in relation to pro-inflammatory $F_c$ receptor binding. In contrast, in some embodiments it may be useful to enhance the ability of the CH2 domain template molecule to activate a complement cascade, for example if one wishes to perform research experiments to study complement or in anti-cancer applications.

In some embodiments, the CH2 domain template molecule has one or more functional binding sites for complement (functional referring to the ability of the binding site to initiate a complement cascade). In some embodiments, the CH2 domain template molecule lacks a functional binding site for a complement molecule (functional referring to the ability of the binding site to initiate a complement cascade). In some embodiments, the complement binding site (or sites) of the CH2 domain template molecule is modified (e.g., mutated, etc.) so as to reduce or eliminate complement activation. Or, the complement binding site(s) may be selected from an immunoglobulin isotype having reduced or absent ability to activate a complement cascade.

Stability and Solubility

Stability is an important property of a protein, and it can determine the ability of the protein to withstand storage or transport conditions as well as affect the protein's half-life after administration (e.g., in serum). The melting temperature of the protein, or the temperature at which the protein loses it tertiary structure, is a measure of the physical stability of the protein. The CH2 domain template molecule may at least retain the melting temperature of the CH2 domain scaffold from which it was created. The CH2 domain template molecule resulting from the transfer of one or more loops may not necessarily have a high melting temperature (e.g., the melting temperature may be about 40° C., 45° C., 50° C., 55° C., etc. However, subsequent modifications of the CH2 domain template molecule may result in higher melting temperatures, for example about 55° C., 60° C., 65° C., 70° C., 75° C., 80° C., 85° C., 90° C., etc. In some embodiments, the CH2 domain template molecule has a melting temperature that is at least 40° C. In some embodiments, the CH2 domain template molecule has a melting temperature that is at least 50° C. In some embodiments, the CH2 domain template molecule has a melting temperature that is at least 60° C. In some embodiments, the CH2 domain template molecule has a melting temperature that is at least 65° C. In some embodiments, the CH2 domain template molecule has a melting temperature that is at least 70° C. In some embodiments, the CH2 domain template molecule has a melting temperature that is at least 80° C. Protocols for determining melting temperature of such proteins are well known to one of ordinary skill in the art (e.g., see Gong et al., 2009, JBC 284:21, pp 14203-14210, and WO 2009/099961A2).

In some embodiments, the CH2 domain template molecule may have a melting temperature that is about the same (or greater than) its CH2 domain scaffold, and the term "about the same" may refer to plus or minus 10%, or plus or minus 20%, etc. For example, a CH2 domain template molecule retains the melting temperature of its CH2 domain scaffold if its melting temperature is within plus or minus 10% of the CH2 domain scaffold.

As described herein, the CH2 domain template molecules may comprise none, one, or more than one "modification." For example, a CH2 domain template may comprise an N-terminal truncation and an additional disulfide bond. In some embodiments, the CH2 domain template comprises a longer loop (e.g., a L3 loop with additional amino acids) and one or more additional disulfide bonds. In some embodiments, the CH2 domain template comprises a longer loop (e.g., a L3 loop with additional amino acids) and an additional FcRn binding site. The present invention is not limited to the aforementioned "modifications" or combinations of modifications.

Pharmaceutical Compositions

In some embodiments, the CH2 domain template molecules comprise or are contained in a pharmaceutical composition, for example for providing increased stability. Examples of pharmaceutical compositions for antibodies and peptides are well known to one of ordinary skill in the art and are described below.

In some embodiments, the CH2 domain template molecules are bound to a molecule (or molecules) that confers increased stability (e.g., serum half-life). Dextrans, various polyethylene glycols (PEG), and albumin-binding peptides are extremely common scaffolds for this purpose (see, for example, Dennis et al., 2002, Journal of Biological Chemistry 33:238390). The molecules may be conjugated to the CH2 domain template molecule by a variety of mechanisms, for example via chemical treatments and/or modification of the protein structure, sequence, etc (see, for example, Ashkenazi et al., 1997, Current Opinions in Immunology 9:195-200; U.S. Pat. No. 5,612,034; U.S. Pat. No. 6,103,233). The molecule (e.g., dextran, PEG, etc.) may be bound to the CH2 domain template molecules through a reactive sulfhydryl by incorporating a cysteine at the end of the protein opposite the binding loops. Such techniques are well known in the art. In another example, one of the CH2 domain template molecules may bind specifically to albumin to utilize the albumin in serum to increase circulating half-life.

Choosing pharmaceutical compositions that confer increased protein stability or binding of the CH2 domain template molecules to scaffolds that confer increased protein stability are not the only ways in which the stability of the protein can be improved. In some embodiments, the CH2 domain template molecules of the present invention may be modified to alter their stability. Again, the term "modified" or "modification," can include one or more mutations, additions, deletions, substitutions, disulfide bond additions, physical alteration (e.g., cross-linking modification, covalent bonding of a component, post-translational modification, e.g., acetylation, glycosylation, pegylation, the like, or a combination thereof), the like, or a combination thereof. Gong et al. (2009, Journal of Biological Chemistry 284:14203-14210) shows examples of modified CH2 domains having increased stability. For example, human γ1 CH2 was cloned and a variety of cysteine mutants were created. The stability of the mutants with respect to the wild type CH2 was determined (e.g., the proteins were subjected to high temperatures and urea treatment). One mutant (m01, which comprised additional disulfide bonds) was particularly stable having a higher melting temperature, increased resistance to urea-induced unfolding, and increased solubility. CH2 domain template molecules with higher melting temperatures and/or increased resistance to urea-induced unfolding and/or and increased solubility may be more likely to withstand storage and transport conditions as well as have increased serum stability after administration.

Due to the unstable nature of proteins, pharmaceutical compositions are often transported and stored via cold chains, which are temperature-controlled uninterrupted supply chains. For example, some pharmaceutical compositions may be stored and transported at a temperature between about 2 to 8 degrees Celsius. Cold chains dramatically increase the costs of such pharmaceutical compositions. Without wishing to limit the present invention to any theory or mechanism, it is believed that increasing the stability of the CH2 domain template molecules of the present invention (e.g., via modification such as addition of disulfide bonds, via pharmaceutical compositions, etc.) may help reduce or eliminate the need to store and transport the CH2 domain template molecules via cold chains.

In some embodiments, the compositions comprise a CH2 domain template molecule as discussed above and a pharmaceutical carrier. The pharmaceutical carrier (vehicles) may be a conventional but is not limited to a conventional carrier (vehicle). For example, E. W. Martin, Remington's Pharmaceutical Sciences, Mack Publishing Co., Easton, Pa., 15th Edition (1975) and D. B. Troy, ed. Remington: The Science and Practice of Pharmacy, Lippincott Williams & Wilkins, Baltimore Md. and Philadelphia, Pa., 21st Edition (2006)

describe compositions and formulations suitable for pharmaceutical delivery of one or more therapeutic compounds or molecules, such as one or more antibodies, and additional pharmaceutical agents.

For example, U.S. Pat. No. 7,648,702 features an aqueous pharmaceutical composition suitable for long-term storage of polypeptides containing an Fc domain of an immunoglobulin. Pharmaceutical compositions may comprise buffers (e.g., sodium phosphate, histidine, potassium phosphate, sodium citrate, potassium citrate, maleic acid, ammonium acetate, tris-(hydroxymethyl)-aminomethane (tris), acetate, diethanolamine, etc.), amino acids (e.g., argenine, cysteine, histidine, glycine, serine, lysine, alanine, glutamic acid, proline), sodium chloride, potassium chloride, sodium citrate, sucrose, glucose, mannitol, lactose, glycerol, xylitol, sorbitol, maltose, inositol, trehalose, bovine serum albumin (BSA), albumin (e.g., human serum albumin, recombinant albumin), dextran, PVA, hydroxypropyl methylcellulose (HPMC), polyethyleneimine, gelatin, polyvinylpyrrolidone (PVP), hydroxyethylcellulose (HEC), polyethylene glycol (PEG), ethylene glycol, dimethylsulfoxide (DMSO), dimethylformamide (DMF), hydrochloride, sacrosine, gamma-aminobutyric acid, Tween-20, Tween-80, sodium dodecyl sulfate (SDS), polysorbate, polyoxyethylene copolymer, sodium acetate, ammonium sulfate, magnesium sulfate, sodium sulfate, trimethylamine N-oxide, betaine, zinc ions, copper ions, calcium ions, manganese ions, magnesium ions, CHAPS, sucrose monolaurate, 2-O-beta-mannoglycerate, the like, or a combination thereof. The present invention is in no way limited to the pharmaceutical composition components disclosed herein, for example pharmaceutical compositions may comprise propellants (e.g., hydrofluoroalkane (HFA)) for aerosol delivery. U.S. Pat. No. 5,192,743 describes a formulation that when reconstituted forms a gel which can improve stability of a protein of interest (e.g., for storage). Pharmaceutical compositions may be appropriately constructed for some or all routes of administration, for example topical administration (including inhalation and nasal administration), oral or enteral administration, intravenous or parenteral administration, transdermal administration, epidural administration, and/or the like. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

In some embodiments, a parenteral formulations may comprise injectable fluids that include pharmaceutically and physiologically acceptable fluids such as water, physiological saline, balanced salt solutions, aqueous dextrose, glycerol or the like as a vehicle. As a non-limiting example, the formulation for injectable trastuzumab includes L-histidine HCl, L-histidine, trehalose dihydrate and polysorbate 20 as a dry powder in a glass vial that is reconstituted with sterile water prior to injection. Other formulations of antibodies and proteins for parenteral or subcutaneous use are well known in the art. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The aforementioned pharmaceutical compositions and protein modifications to increase protein stability can be applied as described in U.S. Patent Application 2009/032692.

Methods

Methods for screening protein binding specificity are well known to one of ordinary skill in the art. The present invention also features methods of identifying a CH2 domain template molecule that specifically binds a target. The method may comprise providing a library of particles (e.g., yeast, particles, cells, molecules such as phage, ribosomes, etc.) that display on their surface a CH2 domain template molecule (as described above), introducing the target to the library of particles; and selecting particles from the library (CH2 domain template molecules) that specifically bind to the target. Particles from the library that specifically bind to the target can be selected via standard methods well known to one of ordinary skill in the art. CH2 domain template molecules may provide a means of obtaining a greater diversity of loops to discover those that have an increased probability of binding a target compared to the diversity of loops that might be available in a whole antibody or variable region-containing format (see, for example, Xiao et al., 2009, Biological and Biophysical Research Communications 387:387-392).

The CH2 domain template molecules of the present invention may be important tools for treating or managing diseases or conditions or detecting diseases or conditions. The present invention also features methods of treating or managing a disease or a condition (e.g., in a mammal, e.g., a human). The methods may comprise obtaining a CH2 domain template molecule (as described above) and introducing the CH2 domain template molecule into a tissue of the mammal, wherein the CH2 domain template molecule binds to a first target and the binding functions to cause neutralization or destruction of the first target. Optionally, the CH2 domain template molecule binds to a first or second target that causes either activation or inhibition of a signaling event through that target. The CH2 domain template molecule may comprise an agent (e.g., chemical, peptide, toxin) that functions to neutralize or destroy the first target. In some embodiments, the agent is inert or has reduced activity when it is linked to the CH2 domain template molecule, wherein the agent is activated or released upon uptake or recycling.

Binding of the CH2 domain template molecule may function to cause the neutralization or destruction of the target. The target may be, for example, a cell, a tumor cell, an immune cell, a protein, a peptide, a molecule, a bacterium, a virus, a protist, a fungus, the like, or a combination thereof. For example, destruction of a target cell (in this example a tumor) could be achieved by therapy using the following CH2 domain template molecule: a first CH2 domain template molecule directed to a particular tumor surface antigen (such as an EGFR, IGFR, nucleolin, ROR1, CD20, CD19, CD22, CD79a, stem cell markers) is linked to a second CH2 domain template molecule that binds to a different tumor surface antigen on the same cell from that bound by the first domain. This arrangement may enhance the specificity of for the tumor over any normal tissues since it may bind more tightly to cells displaying both of the two antigens. The dimer described above may be further linked to an additional CH2 domain template molecule (now a trimer) that binds to an immune effector cell surface antigen (for example, a T-cell specific antigen like CD3, or an NK cell specific surface antigen, like FcγRIIIa). In this way, the specific binding to the tumor by the two targeting domains leads to recruitment of a T-cell (or of an NK cell) that destroys the tumor cell.

The present invention also features methods of detecting a disease or condition (e.g., in a mammal, e.g., a patient). The method may comprise obtaining a CH2 domain template molecule (as described above), introducing the CH2 domain template molecule into a sample of the mammal (or the mammal itself), and detecting binding of the CH2 domain template molecule to a target (e.g., a target associated with the disease or condition) in the sample or mammal. Detecting the binding of the CH2 domain template molecule to the target may be indicative of the disease or condition.

While not explicitly described, the present invention also features isolated DNA sequences and constructs for production of the CH2 domain template molecules and intermediates (e.g., CH2 domain scaffolds, whether wild type or modified).

The present invention provides methods for generating a series of "CH2 domain template molecules." The template molecules are obtained by transferring up to three loops L1, L2 and L3 from a database of crystal structures of domains whose architectures are similar to that of a CH2 domain. The present invention has provided a unique way to define structural loops in CH2 domain based on a set of stereo-chemical criteria, such that the CH2 domain can accept the loops from the donors with a high likelihood of preserving the desired properties of those loops. Criteria for selection of compatible loops include a careful definition to delineate the loops, compatibility in the length of the loops between the donor and CH2 domains as described above. Since the donor molecules are selected from a database of crystal structures, it is believed that the selected templates are well expressed and soluble and have good biophysical and biochemical properties. These template molecules offer a good source for binding to diverse set of targets. In summary, donor loops are chosen based on one or more of the following: the number of amino acids for a given loop (as described above), solubility and expressability of a donor loop in its original format, physical characteristics as described above, and/or epitope recognition.

EXAMPLE 1

Examples of CH2 Domain Template Molecules

The following example is a list of potential CH2 domain template molecules shown in Table 5. The present invention is not limited to the examples described herein.

TABLE 5

| SEQ ID NO: | MOL ID | SEQUENCE |
|---|---|---|
| 54 | CT-2-2456 | GGPSV FLFPPKPKDT LMISRTPEVT CVVVDVSHED PEVKFNWYVD GVEVHNAKTK PREEHNTY RVVSVLTVLH QDWLNGKEYK CKVSNKALPA PIEKTISKAK GQ |
| 55 | CT-2-2022 | GGPSV FLFPPKPKDT LMISRTPEVT CVVVDVSHED PEVKFNWYVD GVEVHNAKTK PREEAASTY RVVSVLTVLH QDWLNGKEYK CKVSNKALPA PIEKTISKAK GQ |
| 56 | CT-2-1329 | GGPSV FLFPPKPKDT LMISRTPEVT CVVVDVSHED PEVKFNWYVD GVEVHNAKTK PREEYDTSTY RVVSVLTVLH QDWLNGKEYK CKVSNKALPA PIEKTISKAK GQ |
| 57 | CT-2-1617 | GGPSV FLFPPKPKDT LMISRTPEVT CVVVDVSHED PEVKFNWYVD GVEVHNAKTK PRVYPGSITY RVVSVLTVLH QDWLNGKEYK CKVSNKALPA PIEKTISKAK GQ |
| 58 | CT-2-1557 | GGPSV FLFPPKPKDT LMISRTPEVT CVVVDVSHED PEVKFNWYVD GVEVHNAKTK PRIYWDDDKTY RVVSVLTVLH QDWLNGKEYK CKVSNKALPA PIEKTISKAK GQ |
| 59 | CT-2-2117 | GGPSV FLFPPKPKDT LMISRTPEVT CVVVDVSHED PEVKFNWYVD GVEVHNAKTK PRISSSGDPTTY RVVSVLTVLH QDWLNGKEYK CKVSNKALPA PIEKTISKAK GQ |
| 60 | CT-1-3-321 | GGPSV FLFPPKPKDT LMISRTPEVT CVVVGFSLST YGMGFNWYVD GVEVHNAKTK PREEQYNSTY RVVSVLTVLH QDWLNGKEYK CKVVQEGY IYEKTISKAK GQ |
| 61 | CT-1-3-1999 | GGPSV FLFPPKPKDT LMISRTPEVT CVVVKSVSTS GYSYFNWYVD GVEVHNAKTK PREEQYNSTY RVVSVLTVLH QDWLNGKEYK CKVQHSREL LTEKTISKAK GQ |
| 62 | CT-1-3-1557 | GGPSV FLFPPKPKDT LMISRTPEVT CVVVGFSLST SGMGFNWYVD GVEVHNAKTK PREEQYNSTY RVVSVLTVLH QDWLNGKEYK CKVTLYYGSV DYEKTISKAK GQ |

TABLE 5-continued

| SEQ ID NO: | MOL ID | SEQUENCE |
|---|---|---|
| 63 | CT-1-3-2022 | GGPSV FLFPPKPKDT LMISRTPEVT CVVVQSVDYN GDSYFNWYVD GVEVHNAKTK PREEQYNSTY RVVSVLTVLH QDWLNGKEYK CKVQQSNEDP FTEKTISKAK GQ |
| 64 | CT-1-3-1795 | GGPSV FLFPPKPKDT LMISRTPEVT CVVVGGSIRS GGYYFNWYVD GVEVHNAKTK PREEQYNSTY RVVSVLTVLH QDWLNGKEYK CKVARLDGYTL DIEKTISKAK GQ |
| 65 | CT-1-3-369 | GGPSV FLFPPKPKDT LMISRTPEVT CVVVKSVSTS GYNYFNWYVD GVEVHNAKTK PREEQYNSTY RVVSVLTVLH QDWLNGKEYK CKVLYSREFPP WTEKTISKAK GQ |
| 66 | CT-1-3-71 | GGPSV FLFPPKPKDT LMISRTPEVT CVVVGYSITS DYAFNWYVD GVEVHNAKTK PREEQYNSTY RVVSVLTVLH QDWLNGKEYK CKVARGWPL AYEKTISKAK GQ |
| 67 | CT-1-3-2167 | GGPSV FLFPPKPKDT LMISRTPEVT CVVVSRDVGG YNYFNWYVD GVEVHNAKTK PREEQYNSTY RVVSVLTVLH QDWLNGKEYK CKVWSFAGSY YVEKTISKAK GQ |
| 68 | CT-1-3-2132 | GGPSV FLFPPKPKDT LMISRTPEVT CVVVGYSITS DFAFNWYVD GVEVHNAKTK PREEQYNSTY RVVSVLTVLH QDWLNGKEYK CKVATAGRGF PYEKTISKAK GQ |
| 69 | CT-1-3-2194 | GGPSV FLFPPKPKDT LMISRTPEVT CVVVSSNIGA GYDFNWYVD GVEVHNAKTK PREEQYNSTY RVVSVLTVLH QDWLNGKEYK CKVQSYDSSLSG SVEKTISKAK GQ |
| 70 | CT-1-3-239 | GGPSV FLFPPKPKDT LMISRTPEVT CVVVGYSITS DYAFNWYVD GVEVHNAKTK PREEQYNSTY RVVSVLTVLH QDWLNGKEYK CKVASYDDYTWF TYEKTISKAK GQ |
| 71 | CT-1-3-1874 | GGPSV FLFPPKPKDT LMISRTPEVT CVVVGYSISS DYAFNWYVD GVEVHNAKTK PREEQYNSTY RVVSVLTVLH QDWLNGKEYK CKVARGYYGSSHS PVEKTISKAK GQ |
| 72 | CT-1-3-2291 | GGPSV FLFPPKPKDT LMISRTPEVT CVVVGFSLST SGMSFNWYVD GVEVHNAKTK PREEQYNSTY RVVSVLTVLH QDWLNGKEYK CKVARRTTTADYF AYEKTISKAK GQ |
| 73 | CT-1-3-2399 | GGPSV FLFPPKPKDT LMISRTPEVT CVVVGFSLST YGVGFNWYVD GVEVHNAKTK PREEQYNSTY RVVSVLTVLH QDWLNGKEYK CKVARLGSDYDVWF DYEKTISKAK GQ |
| 74 | CT-1-3-451 | GGPSV FLFPPKPKDT LMISRTPEVT CVVVGFSLTT YGMGFNWYVD GVEVHNAKTK PREEQYNSTY RVVSVLTVLH QDWLNGKEYK CKVARRAPFY GNHAM DYEKTISKAK GQ |
| 75 | CT-1-3-2067 | GGPSV FLFPPKPKDT LMISRTPEVT CVVVGFSLSTSGMGFNWYVD GVEVHNAKTK PREEQYNSTY RVVSVLTVLH QDWLNGKEYK CKVVRRAHTT VLGDWF AYEKTISKAK GQ |
| 76 | CT-1-3-2425 | GGPSV FLFPPKPKDT LMISRTPEVT CVVVGFSLST SGMSFNWYVD GVEVHNAKTK PREEQYNSTY RVVSVLTVLH QDWLNGKEYK CKVARTLRVS GDYVRDF DLEKTISKAK GQ |
| 77 | CT-1-3-1885 | GGPSV FLFPPKPKDT LMISRTPEVT CVVVGFSIRT SKVGFNWYVD GVEVHNAKTK PREEQYNSTY RVVSVLTVLH QDWLNGKEYK CKVARRGFYG RKYEVNHF DYEKTISKAK GQ |
| 78 | CT-1-3-220 | GGPSV FLFPPKPKDT LMISRTPEVT CVVVGFSLST SGMGFNWYVD GVEVHNAKTK |

TABLE 5-continued

| SEQ ID NO: | MOL ID | SEQUENCE |
|---|---|---|
| | | PREEQYNSTYRVVSVLTVLHQDWLNGKEYK CKVARRTFSY YYGSSFYYF DNEKTISKAK GQ |
| 79 | CT-1-3-1317 | GGPSV FLFPPKPKDT LMISRTPEVT CVVVGFSLSD FGVGFNWYVD GVEVHNAKTK PREEQYNSTY RVVSVLTVLH QDWLNGKEYK CKVAHRRGPT TLFGVPIARG PVNAM DVEKTISKAK GQ |
| 80 | CT-3-1-2291 | GGPSV FLFPPKPKDT LMISRTPEVT CVVVARRTTT ADYFAYFNWYVD GVEVHNAKTK PREEQYNSTY RVVSVLTVLH QDWLNGKEYK CKVGFSLSTSG MSEKTISKAK GQ |
| 81 | CT-3-1-2399 | GGPSV FLFPPKPKDT LMISRTPEVT CVVVARLGSD YDVWFDYFNWYVD GVEVHNAKTK PREEQYNSTY RVVSVLTVLH QDWLNGKEYK CKVGFSLSTYG VGEKTISKAK GQ |
| 82 | CT-3-1-451 | GGPSV FLFPPKPKDT LMISRTPEVT CVVVARRAPF YGNHAMDYFNWYVD GVEVHNAKTK PREEQYNSTY RVVSVLTVLH QDWLNGKEYK CKVGFSLTTYG MGEKTISKAK GQ |
| 83 | CT-3-1-2067 | GGPSV FLFPPKPKDT LMISRTPEVT CVVVVRRAHT TVLGDWFAYFNWYVD GVEVHNAKTK PREEQYNSTY RVVSVLTVLH QDWLNGKEYK CKVGFSLSTSG MGEKTISKAK GQ |
| 84 | CT-3-1-2425 | GGPSV FLFPPKPKDT LMISRTPEVT CVVVATLRV SGDYVRDFDLFNWYVD GVEVHNAKTK PREEQYNSTY RVVSVLTVLH QDWLNGKEYK CKVGFSLSTSG MSEKTISKAK GQ |
| 85 | CT-3-1-1885 | GGPSV FLFPPKPKDT LMISRTPEVT CVVVARRGFY GRKYEVN HFDYFNWYVD GVEVHNAKTK PREEQYNSTY RVVSVLTVLH QDWLNGKEYK CKVGFSIRTSK VGEKTISKAK GQ |
| 86 | CT-3-1-220 | GGPSV FLFPPKPKDT LMISRTPEVT CVVVARRTFS YYYGSSFY YFDNFNWYVD GVEVHNAKTK PREEQYNSTY RVVSVLTVLH QDWLNGKEYK CKVGFSLSTSG MGEKTISKAK GQ |
| 87 | CT-3-1-1317 | GGPSV FLFPPKPKDT LMISRTPEVT CVVVAHRRGP TTLFGVPIARGPVN AMDVFNWYVD GVEVHNAKTK PREEQYNSTY RVVSVLTVLH QDWLNGKEYK CKVGFSLSDFG VGEKTISKAK GQ |
| 88 | CT-3-2-1-CH2 | GGPSV FLFPPKPKDT LMISRTPEVT CVVVSNKAL PAPIFNWYVD GVEVHNAKTK PREEQYNSTY RVVSVLTVLH QDWLNGKEYK CKVDVSHEDPE VKEKTISKAK GQ |

EXAMPLE 2

Prophetic Example of Libraries Based on CH2D Template

A starting CH2D template molecule is selected from among the characterized CH2D templates, as preferably being (a) well expressed in the desired library host (*E. coli* in the case of phage display or in vitro display systems such as CIS or ribosomal display that employ *E. coli* extracts for coupled transcription-translation; yeast in the case of a yeast cell-surface display system), and (b) acceptably stable. The starting CH2D template for a subsequent library may also be selected based on having a loop structure that is more distantly related to the loop structures of any other CH2D which has previously been selected and used to derive a library, thereby accessing additional potential surface shapes with which the new library members may interact.

Based on this selected CH2D template, a series of variants are generated that differ by at least one amino acid in their sequence compared with the sequence of the starting selected CH2D template. Changes may include but are not limited to deletions of an amino acid, insertions, and/or substitutions. In generating a library of potential binding molecules, designed changes may be focused on the loops, and even within those loops at potentially preferred interaction sites, e.g., based on the structure database of donors from which the loops were derived. At any one site, variants may be generated that introduce any of the 20 naturally occurring amino acids (or non-natural amino acids), or a more restricted subset of amino acids might be substituted. Alternatively, in some embodiments, random mutations may be introduced by mutagenesis of the entire molecule, scaffold and loops. Such mutagenesis can be accomplished either in vivo (in a mutagenic host or by addition of exogenous mutagen) or in vitro (by using mutagenic mixtures of precursors and/or by using a DNA polymerase that exhibits reduced or no proofreading nuclease activity). In the case of certain display methods (e.g. CIS, ribosome display), a combination of the two approaches may be employed, synthesizing the initial variants to focus changes within the loops and then allowing random mutagenesis at each round of selection-amplification. Such methods of creating a diverse collection of variant nucleotide sequences to produce variant amino acid sequences are well known in the art.

The libraries made in such a way and displayed by any of the established methods available, may be used to isolate individual molecules from that library which bind to a target of interest. A target molecule is used to contact a display library. The purified target molecules are presented in either 1) a form that is immobilized on a solid surface, or 2) as soluble molecules in solution. If in solution, they are engineered to bear a simple means for subsequent capture, preferably biotin. In the case of cell surface display (e.g. on yeast), the target molecule is tagged fluorescently to enable cell sorting based upon the fluorescent signal due to bound target by the displayed CH2D variant.

Various methods may be used for detecting the binding of the CH2 domain template molecule to the target in the sample. Such methods are well known to one of ordinary skill in the art. In some embodiments, detecting binding of the CH2 domain template molecule to the target indicates the presence of the disease or condition in the sample.

EXAMPLE 3

CH2D Pharmacokinetic Study

The following example describes a single-dose pharmacokinetic study of three CH2D variants in B6 mice, hFcRn mice, and cynomolgus primates.

Three human CH2D variants were produced: (1) CH2D WT monomer (SEQ ID NO: 89); (2) CH2D WT dimer (SEQ ID NO: 90); and (3) CH2D stabilized monomer (m01s) (SEQ ID NO: 91). Briefly, proteins were produced in E. coli, purified by Ni-column affinity chromatography, endotoxin was removed and proteins suspended in PBS at pH 7.4. More specifically, the CH2D stabilized monomer (His-m01s) was expressed in E. coli. Cell paste was resuspended in 10 vol Buffer A (50 mMTris-HCl, and 450 mM NaCl, pH 8.0) and Polymyxin B sulfate was added to suspension at 0.5 mu/ml and gently rotated for 1 h at room temperature. The resulting lysate was centrifuged at 20,000×g for 45 min. Clarified lysate was loaded on to a Ni-Sepharose column pre-equilibrated with Buffer A (2.5 ml of resin used per 1 L expression scale). The column was washed with 10 CV of Buffer A and bound protein was eluted with 100% Buffer B (Buffer A+200 mM Imidazole). Protein-containing fractions were analyzed by Coomassie-stained SDS-PAGE and Western blotting (anti-His antibody). Prominent His-m01s containing fractions were pooled, dialyzed against 1×PBS and the pool was concentrated. Endotoxin levels were estimated using the EndoSafe PTS kit (Charles River Labs) and levels were reduced by the De-tox™ process (Blue Sky's proprietary endotoxin removal method). The final formulation was in PBS at pH 7.4.

The CH2D WT dimer (His-GSGS-hinge-CH2) was enriched according to the protocol for the CH2D stabilized monomer (His-m01s). Prominent His-GSGS-hinge-CH2 containing fractions were pooled, dialyzed against 1×PBS and the pool was concentrated. Endotoxin levels were estimated using the EndoSafe PTS kit (Charles River Labs) and levels were reduced by the De-tox™ process (Blue Sky's proprietary endotoxin removal method). The final formulation was in PBS at pH 7.4.

CH2D WT (His-CH2) was expressed in E. coli strain HB2151. A 50 mL seed culture (SB media w/2% glucose+Kan) was incubated at 37 degrees C. for 16 h and was used to inoculate 1 L of pre-warmed SB media containing 100 μg/mL Ampacillin and 0.2% glucose at a 1:100 dilution. Cell cultures were allowed to incubate at 37 degrees C. until A600=0.9 at which point the culture was induced with 1 mM IPTG. The culture was then allowed to incubate at 30 degrees C. for 18 hrs. Cells were harvested by centrifugation and stored at −80° C. Pre-induction and postinduction samples were analyzed by SDS-PAGE and Western blot.

Twenty four (24) female B6 mice were housed in individually and positively ventilated polycarbonate cages with HEPA filtered air at a density of 4 mice per cage. The animal room was lighted entirely with artificial fluorescent lighting, with a controlled 12 h light/dark cycle (6 am to 6 pm light). The normal temperature and relative humidity ranges in the animal rooms were 22±4° C. and 50±15%, respectively. The animal rooms were set to have 15 air exchanges per hour. Filtered tap water, acidified to a pH of 2.5 to 3.0, and a diet was provided ad libitum. After 1 week of acclimation, the mice each received a single IV injection (100 ug/mouse) of one of three CH2Ds (n=8 for each CH2D): Tail vein injections (50 ul) were performed with CH2D at a concentration of 2 mg/ml.

Mice were bled, orbitally, (50 ul) at pre-dose, 1, 8, 24, 48, 72 and 120 hr. All mice received a baseline bleed, then for the remaining bleeds subsets of 4 mice were bled at alternating time points. All mice were bled at 120 hr. Blood was pooled for each group and processed to serum and frozen at −80 degrees C. Samples were analyzed by enzyme-linked immunosorbent assay (ELISA) (see Example 4). Table 6 shows the pharmacokinetic data in the B6 mice. All pK analyses were performed using ELISA concentration/timepoint data running the PK Solutions 2.0, noncompartmental pharmacokinetics data analysis software from Summit Research Services.

TABLE 6

| PHARMACOKINETIC DATA (B6 MICE) | | |
|---|---|---|
| PEPTIDE | ALPHA PHASE (HR) | BETA PHASE (HR) |
| CH2D WT monomer (12.5 kDa) | 2.0 | 6.9 |
| CH2D WT dimer (25 kDa) | 1.7 | 9.9 |
| CH2D stabilized mo1s (12.5 kDa) | 1.0 | 14.5 |

Transgenic hFcRn mice (Tg276 hemizygous) are described in Roopenian D C., et al., Chapter 6 in Mouse models for drug discovery, Methods in molecular biology 602, 2010, 93-104 and in Roopenian D C. and Akilesh S., Nature Reviews 7, Sep. 2007, [715-725. Twenty four (24) female transgenic hFcRn mice (Tg276 hemizygous) were housed in individually and positively ventilated polycarbonate cages with HEPA filtered air at a density of 4 mice per cage. The animal room was lighted entirely with artificial fluorescent lighting, with a controlled 12 h light/dark cycle (6 am to 6 pm light). The normal temperature and relative humidity ranges in the animal rooms were 22 plus/minus 4 degrees C. and 50 plus/minus 15%, respectively. The animal rooms were set to have 15 air exchanges per hour. Filtered tap water, acidified to a pH of 2.5 to 3.0, and a diet was provided ad libitum. After 1 week of acclimation, the mice each received a single IV injection (100 ug/mouse) of one of three CH2Ds (n=8 for each CH2D): Tail vein injections (50 ul) were performed with CH2D at a concentration of 2 mg/ml.

Mice were bled, orbitally, (50 μl) at pre-dose, 1, 8, 24, 48, 72 and 120 hr. All mice received a baseline bleed, then for the remaining bleeds subsets of 4 mice were bled at alternating time points. All mice were bled at 120 hr. Blood was pooled for each group and processed to serum and frozen at −80 degrees C. Samples were analyzed by enzyme-linked immunosorbent assay (ELISA) (see Example 4). Table 7 shows the pharmacokinetic data in the transgenic mice. All pK analyses were performed using ELISA concentration/timepoint data running the PK Solutions 2.0, noncompartmental pharmacokinetics data analysis software from Summit Research Services. Due to the minimal early time points and need for the best fit for the correlation coefficient, the data was calculated based on the Elimination phase only (eta-phase).

TABLE 7

PHARMACOKINETIC DATA (TRANSGENIC hFcRn MICE)

| PEPTIDE | ALPHA PHASE (HR) | BETA PHASE (HR) |
|---|---|---|
| CH2D WT monomer (12.5 kDa) | N/A | 7.6 |
| CH2D WT dimer (25 kDa) | N/A | 10.3 |
| CH2D stabilized mo1s (12.5 kDa) | N/A | 8.5 |

Only the CH2D WT dimer and CH2D stabilized monomer (m01s) were tested in cynomolgus primates. The CH2Ds were dosed as a single IV administration at either 10 mg/kg or 20 mg/kg in 3 animals per test article (12 total). Animals in the 10 mg/kg group were administered approximately 16 ml at 2-3 ml/min of m01s and 11 ml at 2-3 ml/min of the dimer. Animals in the 20 mg/kg group received 31 ml at 1 ml/min of m01s and 22 ml at 1 ml/min for the dimer. In addition, animals in the 20 mg/kg group developed a shigella infection and were treated with Bytril for one week with one week washout before starting the study. Finally, all animals in the 20 mg/kg group received 20 ml/kg (avg. 90 ml) of normal saline SQ to expand their blood volume 24 hours prior to dosing. Blood draws were timed following administration. Purified CH2D protein was provided in PBS. Animals were individually caged for the duration of the study and observed daily for clinical signs and symptoms. 3 to 5 ml of blood was drawn at baseline (t0), 1, 2, 4, 12, 24, 48, and 72 hrs after test article administration. Serum was prepared for ELISA standards. For all ELISA's the material used for injection was used to make the standard curves. The data are reported from pooled serum samples for each group. Table 8 and Table 9 show the pharmacokinetic data in the cynomolgus primates (10 mg/kg and 20 mg/kg, respectively). All pK analyses were performed using ELISA concentration/timepoint data running the PK Solutions 2.0, noncompartmental pharmacokinetics data analysis software from Summit Research Services.

TABLE 8

PHARMACOKINETIC DATA (CYNOMOLGUS PRIMATES, 10 MG/KG)

| PEPTIDE | ALPHA PHASE (HR) | BETA PHASE (HR) |
|---|---|---|
| CH2D WT dimer (25 kDa) | 0.7 | 13.5 |
| CH2D stabilized mo1s (12.5 kDa) | 0.7 | 11.4 |

TABLE 9

PHARMACOKINETIC DATA (CYNOMOLGUS PRIMATES, 20 MG/KG)

| PEPTIDE | ALPHA PHASE (HR) | BETA PHASE (HR) |
|---|---|---|
| CH2D WT dimer (25 kDa) | 2.1 | 8.8 |
| CH2D stabilized mo1s (12.5 kDa) | 0.7 | 11.1 |

Figure 3:
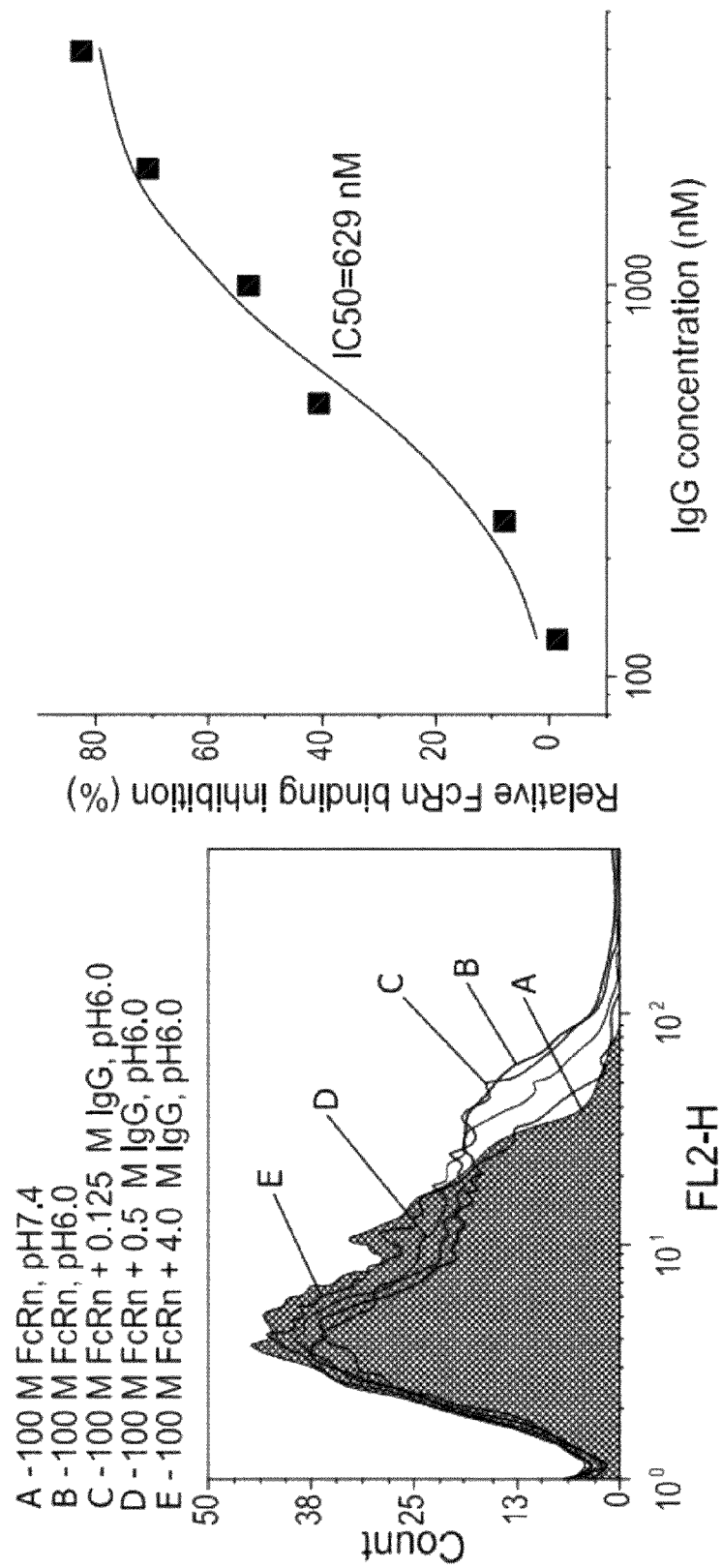
FIG. 3 shows the inhibition of binding of mO1s to FcRn on yeast cells by IgG1. Percent of inhibition (%)=[(mean max at pH6.0−mean at pH6.0)/(mean max at pH6.0−mean at 7.4)]×100. While mean max at pH 6.0 was the mean value in the absence of IgG, mean at pH 7.4 was mean value measured at pH 7.4 in the absence of IgG and mean at pH 6.0 was mean value measured at pH 6.0 with different IgG concentrations. The binding was inhibited with the increase of IgG concentration. 1050=629 nM.

The CH2Ds tested in this study demonstrated serum half-lives ranging from 7-15 hours in B6 mice, 7-10 hours in hFcRn mice and 8-14 hours in cynomolgus monkeys. The increase in the observed serum half-life for hCH2D may be due to the binding of CH2D to the FcRn receptor, as these CH2D's had no target binding specificity. Binding to FcRn will result in serum retention and delay in renal clearance. Potential binding of CH2D to FcRn is further supported by work demonstrating that the CH2D stabilized (m01s) binds to soluble, recombinant hFcRn and can be blocked by human Fc (see FIG. 1, FIG. 3). In addition, CH2D formats have also been shown to bind to hFcRn expressed on the surface of yeast cells and analyzed by FACS (see FIG. 2).

EXAMPLE 4

ELISA

ELISA is well known to one of ordinary skill in the art. The following example describes a non-limiting example of monitoring concentrations of CH2 protein in monkey serum (sera) with Capturing ELISA.

Materials: Protein G resin (cat#17-0618-02 for 25 ml or 17-0404-01 for 5 of 1 ml column, GE Healthcare); Mouse monoclonal antibody to human IgG1 Fc CH2 domain specific: at 1 mg/ml (cat#MCA2477G, clone#8A4); Mouse monoclonal antibody to human IgG1 Fc (ABD Serotec, cat# MCA2477G); Half area ELISA plate: (cat# CLS 3690-100 Corning ½ area 96 well plate, from Corning or Sigma); Anti-human IgG (Fc specific) peroxidase conjugate (Sigma, A0170); Wash buffer: PBST (PBS+0.05% Tween 20); Blocking buffer: 4% non-fat dry milk in PBST, ABTS substrate for HRP (cat#1684302 from Roche)

Procedure: (1) Preparing monkey serum samples for capture ELISA: The monkey (rhesus or cynomolgus) IgG is also recognized by the mouse IgG 8A4, it needs to be depleted from serum before the CH2-containing serum is applied to ELISA wells for capture ELISA. Protein G resin does not bind to CH2 protein. Clarify the serum by centrifugation at 20,000 g for 10 min. Recover the clear supernatant without disturbing the red blood cell pellet. Dilute the serum in PBS at 1:1 ratio, named serum/PBS thereafter. A minimal of 300 ul of serum/PBS sample is required for a test. Incubate the serum/PBS sample with protein G resin at 4 C for 1 hour. Use 100 ul (packed volume) (or 200 ul 50% slurry) protein G resin for every 100 ul serum/PBS sample. After incubation, spin at 5000g×2 min, recover the supernatant, which has monkey IgG depleted now—called serum/PBS- thereafter. The serum/PBS- sample will be tested at various dilutions (typically 1:2 serial dilution in blocking buffer), to ensure that the CH2 concentrations in wells fall into the CH2 standard range. Each dilution will be tested in duplicates. Protein G resin can be regenerated: strip bound IgG with pH 3.0 buffer, either 100 mM glycine or 50 mM acetic acid first then equilibrate with PBS.

(2) For capture ELISA, coat mouse mAb@human CH2 (the capture antibody) on half area ELISA plate wells at 100 ng/well in 50 ul PBS. Let the plate incubate at 4 C overnight.

(3) Wash the plate 2 times with PBST. Each wash consists of adding 150 ul PBST/well, immediately pouring off the wash buffer, and tapping out residual buffer on paper towel.

(4) Add 100 ul blocking buffer to block the uncoated areas in the wells. Incubate at 37 C×1 hour.

(5) While the blocking is in progress, prepare the CH2 standard samples. (1 mg/ml CH2=66 uM). Start the standard from 1000 nM, then 1:5 or 1:2 serial dilutions in blocking buffer to cover the range of expected CH2 concentrations in serum. Also include two wells with no CH2 as the background control.

(6) Pour off the blocking buffer from ELISA plate. Wash the ELISA plate with PBST 4 times. Add CH2 standards and serum/PBS- in duplicate wells. Each well receives 50 ul of CH2 standard solution in blocking buffer or diluted serum/PBS-. Let the plate incubate for 2 hours at 37 C.

(7) Pour off the CH2 standard and serum/PBS-. Serum samples should be disposed properly in biohazard containers. Wash the ELISA plate 4 times with PBST.

(8) Prepare the secondary Ab, anti-human IgG (Fc specific) peroxidase conjugate (Sigma, A0170), used at 1:1000 or 1:2000 in blocking buffer. Add 50 ul/well.

(9) Let the plate incubate at 37 C for 1 hour.

(10) Pour off the secondary Ab solution. Wash the plate 4 times with PBST.

(11) Add HRP substrate ABTS to develop: 50 ul/well.

(12) Read the signal in a 96-well plate reader at 405 nm wavelength. The time of reading may vary depending on the intensity of signal. If required, plates may be read multiple times. Note: If multiple plates are used for many samples, each plate should have CH2 standards included. It is NOT recommended to use the CH2 standard readings from one plate to calculate samples from another ELISA plate. This anti-human IgG Fc antibody can also binding to monkey IgG, therefore, all the samples with serum should be depleted by protein G twice. The amount of use of protein G should be optimized to make sure the monkey IgGs are completely cleaned.

EXAMPLE 5

Expression and Properties of CH2 Scaffolds

The following example describes testing expression and properties of a series of variant CH2 scaffold molecules in *E. coli*. The variants as well as the parent molecule (SEQ ID NO: 92) are shown in Table 10 (FR1=Framework 1, L1=Loop 1, FR2=Framework 2, L2=loop 2, FR3=Framework 3, L3=loop 3, FR4=Framework, LP=DsbA leader peptide, His=His tag). Each variant represents particular loops grafted onto the CH2 scaffold in place of the native loops.

TABLE 10

| | Parent (SEQ ID NO: 92) | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | DVSHEDPEVK | (SEQ ID NO: 2) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | SNKALPAPI | (SEQ ID NO: 3) |
| FR4 | EKTISKAKGQ | (SEQ ID NO: 146) |
| | CT-2-2456 (SEQ ID NO: 93) | |
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | DVSHEDPEVK | (SEQ ID NO: 2) |
| FR2 | FNWYVDGVEVHNAKTKPR | (SEQ ID NO: 144) |
| L2 | EEHN | (SEQ ID NO: 5) |
| FR3 | TYRVVSVLTVLHQDWLNGKEYKCKV | (SEQ ID NO: 145) |
| L3 | SNKALPAPI | (SEQ ID NO: 3) |
| FR4 | EKTISKAKGQ | (SEQ ID NO: 146) |
| | CT-2-2022 (SEQ ID NO: 94) | |
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | DVSHEDPEVK | (SEQ ID NO: 2) |
| FR2 | FNWYVDGVEVHNAKTKPR | (SEQ ID NO: 144) |
| L2 | EEAAS | (SEQ ID NO: 5) |
| FR3 | TYRVVSVLTVLHQDWLNGKEYKCKV | (SEQ ID NO: 145) |
| L3 | SNKALPAPI | (SEQ ID NO: 3) |
| FR4 | EKTISKAKGQ | (SEQ ID NO: 146) |
| | CT-2-1329 (SEQ ID NO: 95) | |
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | DVSHEDPEVK | (SEQ ID NO: 2) |
| FR2 | FNWYVDGVEVHNAKTKPR | (SEQ ID NO: 144) |
| L2 | EEYDTS | (SEQ ID NO: 7) |
| FR3 | TYRVVSVLTVLHQDWLNGKEYKCKV | (SEQ ID NO: 145) |
| L3 | SNKALPAPI | (SEQ ID NO: 3) |
| FR4 | EKTISKAKGQ | (SEQ ID NO: 146) |
| | CT-2-1617 (SEQ ID NO: 96) | |
| LP | MKKIWLALAGLVLAFSASAAGYE | (SEQ ID NO: 141) |
| HIS | DGKGHHHHHHAPELL | (SEQ ID NO: 142) |

TABLE 10-continued

| | | |
|---|---|---|
| FR1 | GGPSVFLFPPKPKDTLMISRTPE-VTCVVV | (SEQ ID NO: 143) |
| L1 | DVSHEDPEVK | (SEQ ID NO: 2) |
| FR2 | FNWYVDGVEVHNAKTKPR | (SEQ ID NO: 144) |
| L2 | VYPGSI | (SEQ ID NO: 8) |
| FR3 | TYRVVSVLTVLHQDWLNGKEYKCKV | (SEQ ID NO: 145) |
| L3 | SNKALPAPI | (SEQ ID NO: 3) |
| FR4 | EKTISKAKGQ | (SEQ ID NO: 146) |

CT-2-1557 (SEQ ID NO: 97)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | DVSHEDPEVK | (SEQ ID NO: 2) |
| FR2 | FNWYVDGVEVHNAKTKPR | (SEQ ID NO: 144) |
| L2 | IYWDDDK | (SEQ ID NO: 9) |
| FR3 | TYRVVSVLTVLHQDWLNGKEYKCKV | (SEQ ID NO: 145) |
| L3 | SNKALPAPI | (SEQ ID NO: 3) |
| FR4 | EKTISKAKGQ | (SEQ ID NO: 146) |

CT-2-2117 (SEQ ID NO: 98)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | DVSHEDPEVK | (SEQ ID NO: 2) |
| FR2 | FNWYVDGVEVHNAKTKPR | (SEQ ID NO: 144) |
| L2 | ISSSGDPT | (SEQ ID NO: 10) |
| FR3 | TYRVVSVLTVLHQDWLNGKEYKCKV | (SEQ ID NO: 145) |
| L3 | SNKALPAPI | (SEQ ID NO: 3) |
| FR4 | EKTISKAKGQ | (SEQ ID NO: 146) |

CT-1-3-321 (SEQ ID NO: 99)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | GFSLSTYGMG | (SEQ ID NO: 11) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | VQEGYIY | (SEQ ID NO: 35) |
| FR4 | EKTISKAKGQ | (SEQ ID NO: 146) |

CT-1-3-1999 (SEQ ID NO: 100)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | KSVSTSGYSY | (SEQ ID NO: 12) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | QHSRELLT | (SEQ ID NO: 36) |
| FR4 | EKTISKAKGQ | (SEQ ID NO: 146) |

CT-1-3-1557 (SEQ ID NO: 101)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | GFSLSTSGMG | (SEQ ID NO: 13) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | TLYYGSVDY | (SEQ ID NO: 37) |
| FR4 | EKTISKAKGQ | (SEQ ID NO: 146) |

CT-1-3-2022 (SEQ ID NO: 102)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | QSVDYNGDSY | (SEQ ID NO: 14) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | QQSNEDPFT | (SEQ ID NO: 38) |
| FR4 | EKTISKAKGQ | (SEQ ID NO: 146) |

CT-2-3-1795 (SEQ ID NO: 103)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | GGSIRSGGYY | (SEQ ID NO: 15) |
| FR2 | FNWYVDGVEVHNAKTKPR | (SEQ ID NO: 144) |

TABLE 10-continued

| | | |
|---|---|---|
| L2 | EEQYNS | (SEQ ID NO: 4) |
| FR3 | TYRVVSVLTVLHQDWLNGKEYKCKV | (SEQ ID NO: 145) |
| L3 | ARLDGYTLDI | (SEQ ID NO: 39) |
| FR4 | EKTISKAKGQ | (SEQ ID NO: 146) |

CT-1-3-369 (SEQ ID NO: 104)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | KSVSTSGYNY | (SEQ ID NO: 16) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | LYSREFPPWT | (SEQ ID NO: 40) |
| FR4 | EKTISKAKGQ | (SEQ ID NO: 146) |

CT-1-3-71 (SEQ ID NO: 105)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | GYSITSDYA | (SEQ ID NO: 17) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | ARGWPLAY | (SEQ ID NO: 41) |
| FR4 | EKTISKAKGQ | (SEQ ID NO: 146) |

CT-1-3-2167 (SEQ ID NO: 106)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | SRDVGGYNY | (SEQ ID NO: 18) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | WSFAGSYYV | (SEQ ID NO: 42) |
| FR4 | EKTISKAKGQ | (SEQ ID NO: 146) |

CT-1-3-2132 (SEQ ID NO: 107)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | GYSITSDFA | (SEQ ID NO: 19) |
| FR2 | FNWYVDGVEVHNAKTKPR | (SEQ ID NO: 144) |
| L2 | EEQYNS | (SEQ ID NO: 146) |
| FR3 | TYRVVSVLTVLHQDWLNGKEYKCKV | (SEQ ID NO: 145) |
| L3 | ATAGRGFPY | (SEQ ID NO: 43) |
| FR4 | EKTISKAKGQ | (SEQ ID NO: 146) |

CT-1-3-2194 (SEQ ID NO: 108)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | SSNIGAGYD | (SEQ ID NO: 20) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | QSYDSSLSGSV | (SEQ ID NO: 44) |
| FR4 | EKTISKAKGQ | (SEQ ID NO: 146) |

CT-1-3-239 (SEQ ID NO: 109)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | GYSITSDYA | (SEQ ID NO: 17) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | ASYDDYTWFTY | (SEQ ID NO: 45) |
| FR4 | EKTISKAKGQ | (SEQ ID NO: 146) |

CT-1-3-1874 (SEQ ID NO: 110)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | GYSISSDYA | (SEQ ID NO: 21) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |

TABLE 10-continued

| | | |
|---|---|---|
| L3 | ARGYYGSSHSPV | (SEQ ID NO: 46) |
| FR4 | EKTISKAKGQ | (SEQ ID NO: 146) |

CT-1-3-2291 (SEQ ID NO: 111)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | GFSLSTSGMS | (SEQ ID NO: 22) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | ARRTTTADYFAY | (SEQ ID NO: 27) |
| FR4 | EKTISKAKGQ | (SEQ ID NO: 146) |

CT-1-3-2399 (SEQ ID NO: 112)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | GFSLSTYGVG | (SEQ ID NO: 23) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | ARLGSDYDVWFDY | (SEQ ID NO: 28) |
| FR4 | EKTISKAKGQ | (SEQ ID NO: 146) |

CT-1-3-451 (SEQ ID NO: 113)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | GFSLTTYGMG | (SEQ ID NO: 24) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | ARRAPFYGNHAMDY | (SEQ ID NO: 29) |
| FR4 | EKTISKAKGQ | (SEQ ID NO: 146) |

CT-1-3-2067 (SEQ ID NO: 114)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | GFSLSTSGMG | (SEQ ID NO: 13) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | VRRAHTTVLGDWFAY | (SEQ ID NO: 30) |
| FR4 | EKTISKAKGQ | (SEQ ID NO: 146) |

CT-1-3-2425 (SEQ ID NO: 115)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | GFSLSTSGMS | (SEQ ID NO: 22) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | ARTLRVSGDYVRDFDL | (SEQ ID NO: 31) |
| FR4 | EKTISKAKGQ | (SEQ ID NO: 146) |

CT-1-3-1885 (SEQ ID NO: 116)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | GFSIRTSKVG | (SEQ ID NO: 25) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | ARRGFYGRKYEVNHFDY | (SEQ ID NO: 32) |
| FR4 | EKTISKAKGQ | (SEQ ID NO: 146) |

CT-1-3-220 (SEQ ID NO: 117)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | GFSLSTSGMG | (SEQ ID NO: 13) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | ARRTFSYYYGSSFYYFDN | (SEQ ID NO: 33) |
| FR4 | EKTISKAKGQ | (SEQ ID NO: 146) |

CT-1-3-1317 (SEQ ID NO: 118)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |

TABLE 10-continued

| | | |
|---|---|---|
| L1 | GFSLSDFGVG | (SEQ ID NO: 26) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | AHRRGPTTLFGVPIARGPVNAMDV | (SEQ ID NO: 34) |
| FR4 | EKTISKAKGQ | (SEQ ID NO: 146) |

CT-3-1-2291 (SEQ ID NO: 119)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | ARRTTTADYFAY | (SEQ ID NO: 27) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | GFSLSTSGMS | (SEQ ID NO: 22) |
| FR4 | EKTISKAKGQ | (SEQ ID NO: 146) |

CT-3-1-2399 (SEQ ID NO: 120)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | ARLGSDYDVWFDY | (SEQ ID NO: 28) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | GFSLSTYGVG | (SEQ ID NO: 23) |
| FR4 | EKTISKAKGQ | (SEQ ID NO: 146) |

CT-3-1-451 (SEQ ID NO: 121)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | ARRAPFYGNHAMDY | (SEQ ID NO: 29) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | GFSLTTYGMG | (SEQ ID NO: 24) |
| FR4 | EKTISKAKGQ | (SEQ ID NO: 146) |

CT-3-1-2067 (SEQ ID NO: 122)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | VRRAHTTVLGDWFAY | (SEQ ID NO: 30) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | GFSLSTSGMG | (SEQ ID NO: 13) |
| FR4 | EKTISKAKGQ | (SEQ ID NO: 146) |

CT-3-1-2425 (SEQ ID NO: 123)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | ARTLRVSGDYVRDFDL | (SEQ ID NO: 31) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | GFSLSTSGMS | (SEQ ID NO: 22) |
| FR4 | EKTISKAKGQ | (SEQ ID NO: 146) |

CT-3-1-1885 (SEQ ID NO: 124)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | ARRGFYGRKYEVNHFDY | (SEQ ID NO: 32) |
| FR2 | FNWYVDGVEVHNAKTKPR | (SEQ ID NO: 143) |
| L2 | EEQYNS | (SEQ ID NO: 3) |
| FR3 | TYRVVSVLTVLHQDWLNGKEYKCKV | (SEQ ID NO: 145) |
| L3 | GFSIRTSKVG | (SEQ ID NO: 25) |
| FR4 | EKTISKAKGQ | (SEQ ID NO: 146) |

CT-3-1-220 (SEQ ID NO: 125)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | ARRTFSYYYGSSFYYFDN | (SEQ ID NO: 33) |
| FR2 | FNWYVDGVEVHNAKTKPR | (SEQ ID NO: 144) |

TABLE 10-continued

| | | |
|---|---|---|
| L2 | EEQYNS | (SEQ ID NO: 4) |
| FR3 | TYRVVSVLTVLHQDWLNGKEYKCKV | (SEQ ID NO: 145) |
| L3 | GFSLSTSGMG | (SEQ ID NO: 13) |
| FR4 | EKTISKAKGQ | (SEQ ID NO: 146) |

CT-3-1-1317 (SEQ ID NO: 126)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | AHRRGPTTLFGVPIARGPVNAMDV | (SEQ ID NO: 34) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | GFSLSDFGVG | (SEQ ID NO: 26) |
| FR4 | EKTISKAKGQ | (SEQ ID NO: 146) |

CT-3-2-1-CH2 (SEQ ID NO: 127)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | SNKALPAPI | (SEQ ID NO: 3) |
| FR2 | FNWYVDGVEVHNAKTKPR | (SEQ ID NO: 144) |
| L2 | CEQYNS | (SEQ ID NO: 147) |
| FR3 | TYCVVSVLTVLHQDWLNGKEYKCKV | (SEQ ID NO: 148) |
| L3 | DVSHEDPEVK | (SEQ ID NO: 2) |
| FR4 | EKTISKAKGQ | (SEQ ID NO: 146) |

CT-3-2-1-CH2* (SEQ ID NO: 128)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | SNKALPAPI | (SEQ ID NO: 3) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | DVSHEDPEVK | (SEQ ID NO: 2) |
| FR4 | EKTISKAKGQ | (SEQ ID NO: 146) |

CT-S-S-N-TERM1* (SEQ ID NO: 129)

| | | |
|---|---|---|
| LP | MKKIWLALAGLVLAFSASAAGYE | (SEQ ID NO: 1) |
| HIS | DGKGHHHHHHAPELL | (SEQ ID NO: 2) |
| FR1 | GGPSCFLFPPKPKDTLMISRTPE-VTCVVV | (SEQ ID NO: 149) |
| L1 | DVSHEDPEVK | (SEQ ID NO: 2) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | SNKALPAPIC | (SEQ ID NO: 3) |
| FR4 | EKTISKAKGQ | (SEQ ID NO: 146) |

CT-S-S-N-TERM1 (SEQ ID NO: 130)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPSCFLFPPKPKDTLMISRTPE-VTCVVV | (SEQ ID NO: 149) |
| L1 | DVSHEDPEVK | (SEQ ID NO: 2) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | SNKALPAPC | (SEQ ID NO: 150) |
| FR4 | EKTISKAKGQ | (SEQ ID NO: 146) |

CT-S-S-N-TERM2* (SEQ ID NO: 131)

| | | |
|---|---|---|
| LP | MKKIWLALAGLVLAFSASAAGYE | (SEQ ID NO: 141) |
| HIS | DGKGHHHHHHAPELL | (SEQ ID NO: 143) |
| FR1 | GGPCVFLFPPKPKDTLMISRTPE-VTCVVV | (SEQ ID NO: 151) |
| L1 | DVSHEDPEVK | (SEQ ID NO: 2) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | SNKALPAPIC | (SEQ ID NO: 3) |
| FR4 | EKTISKAKGQ | (SEQ ID NO: 146) |

CT-S-S-N-TERM2 (SEQ ID NO: 132)

| | | |
|---|---|---|
| LP | MKKIWLALAGLVLAFSASAAGYE | (SEQ ID NO: 141) |
| HIS | DGKGHHHHHHAPELL | (SEQ ID NO: 142) |
| FR1 | GGPCVFLFPPKPKDTLMISRTPE-VTCVVV | (SEQ ID NO: 151) |
| L1 | DVSHEDPEVK | (SEQ ID NO: 2) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |

TABLE 10-continued

| | | |
|---|---|---|
| L3 | SNKALPAPC | (SEQ ID NO: 150) |
| FR4 | EKTISKAKGQ | (SEQ ID NO: 146) |
| **CT-S-S-C-TERM\* (SEQ ID NO: 133)** | | |
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFCPKPKDTLMISRTPE-VTCVVV | (SEQ ID NO: 152) |
| L1 | DVSHEDPEVK | (SEQ ID NO: 2) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | SNKALPAPI | (SEQ ID NO: 3) |
| FR4 | EKTICSKAKGQ | (SEQ ID NO: 153) |
| CT-S-S-C-TERM (SEQ ID NO: 134) | | |
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFCPKPKDTLMISRTPE-VTCVVV | (SEQ ID NO: 152) |
| L1 | DVSHEDPEVK | (SEQ ID NO: 2) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | SNKALPAPI | (SEQ ID NO: 3) |
| FR4 | EKTCSKAKGQ | (SEQ ID NO: 154) |
| CT-S-S-L2 (SEQ ID NO: 135) | | |
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTCVVV | (SEQ ID NO: 143) |
| L1 | DVSHEDPEVK | (SEQ ID NO: 2) |
| FR2 | FNWYVDGVEVHNAKTKPR | (SEQ ID NO: 144) |
| L2 | CEQYNS | (SEQ ID NO: 147) |
| FR3 | TYCVVSVLTVLHQDWLNGKEYKCKV | (SEQ ID NO: 148) |
| L3 | SNKALPAPI | (SEQ ID NO: 3) |
| FR4 | EKTISKAKGQ | (SEQ ID NO: 146) |
| CT-S-S-M01 (SEQ ID NO: 136) | | |
| LP | MKKIWLALAGLVLAFSASAAGYE | (SEQ ID NO: 141) |
| HIS | DGKGHHHHHHAPELL | (SEQ ID NO: 142) |
| FR1 | GGPSVFCFPPKPKDTLMISRTPE-VTCVVV | (SEQ ID NO: 155) |
| L1 | DVSHEDPEVK | (SEQ ID NO: 2) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKCKV | (SEQ ID NO: 145) |
| L3 | SNKALPAPI | (SEQ ID NO: 3) |
| FR4 | ECTISKAKGQ | (SEQ ID NO: 156) |
| CT-A-A-not-S-S (SEQ ID NO: 137) | | |
| LP | MKKIWLALAGLVLAFSASAAGYE | (SEQ ID NO: 141) |
| HIS | DGKGHHHHHHAPELL | (SEQ ID NO: 142) |
| FR1 | GGPSVFLFPPKPKDTLMISRTPE-VTAVVV | (SEQ ID NO: 157) |
| L1 | DVSHEDPEVK | (SEQ ID NO: 2) |
| FR2 | FNWYVDGVEVHNAKTKPR | (SEQ ID NO: 144) |
| L2 | EEQYNS | (SEQ ID NO: 4) |
| FR3 | TYRVVSVLTVLHQDWLNGKEYKAKV | (SEQ ID NO: 158) |
| L3 | SNKALPAPI | (SEQ ID NO: 3) |
| FR4 | EKTISKAKGQ | (SEQ ID NO: 146) |
| CT-S-S-M01-YTEA (SEQ ID NO: 138) | | |
| LP | MKKIWLALAGLVLAFSASAAGYE | (SEQ ID NO: 141) |
| HIS | DGKGHHHHHHAPELL | (SEQ ID NO: 142) |
| FR1 | GGPSVFCFPPKPKDTLYITREPE-VTCVVV | (SEQ ID NO: 159) |
| L1 | DVSHEDPEVK | (SEQ ID NO: 2) |
| FR2 | FNWYVDGVEVHNAKTKPR | (SEQ ID NO: 144) |
| L2 | EEQYNS | (SEQ ID NO: 4) |
| FR3 | TYRVVSVLAVLHQDWLNGKEYKCKV | (SEQ ID NO: 160) |
| L3 | SNKALPAPI | (SEQ ID NO: 3) |
| FR4 | ECTISKAKGQ | (SEQ ID NO: 156) |

SEQ ID NO: 92 is the parent sequence. SEQ ID NO: 93 through SEQ ID NO: 138 are the variants. For SEQ ID NO: 93 through SEQ ID NO: 98, L2 loops from donors are used, and the L1 loops and L3 loops are from the CH2s. For SEQ ID NO: 99 through SEQ ID NO: 110, L2 loops from the CH2s are used, and the L1 loops and L3 loops are from the donors. For SEQ ID NO: 111 through SEQ ID NO: 118, L2 loops from the CH2s are used, and the L1 loops and L3 loops are from the donors (L3 loops are long loops). SEQ ID NO: 119 through SEQ ID NO: 126 are similar to SEQ ID NO: 111 THROUGH SEQ ID NO: 118, respectively, but the L1 loops and L3 loops are interchanged. SEQ ID NO: 127 through SEQ ID NO: 138 have engineered disulfide bonds.

A set of plasmids encoding the variants (and the parent) were provided. All constructs were cloned into pJexpress404 (Apr) and are under the control of the T5 promoter; all had standard ribosome binding sites, and NdeI and XhoI sites for subcloning. The variants were tested for expression, solubility, and folding (see Table 11). In Table 11, "Exp" refers to total made, "Peri" refers the relative amount of soluble protein made, "ELISA" refers to a relative measure of the amount of folded-correctly template made.

TABLE 11

| SEQ ID NO | Exp | Peri | ELISA |
|---|---|---|---|
| 92 | 100 | 100 | 100 |
| 93 | 124 | 20 | 30 |
| 94 | 130 | 56 | 70 |
| 95 | 142 | 87 | 64 |
| 96 | 169 | 20 | 10 |
| 99 | 163 | 14 | 2.5 |
| 100 | 10 | | |
| 101 | 114 | 14 | 1 |
| 102 | 124 | 21 | 1.4 |
| 103 | 121 | 5 | 1.3 |
| 111 | 74 | 0 | 0 |
| 112 | 200 | 5 | 0 |
| 113 | 58 | 10 | 0 |
| 114 | 8 | | |
| 115 | 163 | 5 | 0 |
| 116 | 80 | 5 | 0 |
| 117 | 137 | 0 | 0 |
| 118 | 168 | 0 | 0 |
| 119 | 69 | 10 | 10 |
| 120 | 194 | 5 | 5 |
| 121 | 118 | 5 | 5 |
| 122 | 85 | 10 | 10 |
| 123 | 113 | 20 | 0 |
| 124 | 101 | 5 | 0 |
| 125 | 101 | 5 | 0 |
| 126 | 101 | 10 | 0 |
| 127 | 112 | 10 | 0 |
| 128 | 28 | 20 | 3.8 |
| 129 | 147 | 46 | 80 |
| 130 | 60 | 104 | 20 |
| 131 | 121 | 1 | 1 |
| 132 | 68 | 1 | 3 |
| 133 | 128 | 0 | 0 |
| 134 | 65 | 65 | 12 |
| 145 | 104 | 20 | 28 |
| 136 | 57 | 1 | 3 |
| 137 | 148 | 10 | 10 |
| 138 | 285 | 20 | 50 |

For reference, sequences and sequence ID numbers disclosed herein can be found in Table 12 below.

TABLE 12

| SEQ ID NO: | SEQUENCE |
|---|---|
| 1 | APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQ |
| 2 | DVSHEDPEVK |
| 3 | SNKALPAPI |
| 4 | EEQYNS |
| 5 | EEHN |
| 6 | EEAAS |
| 7 | EEYDTS |
| 8 | VYPGSI |
| 9 | IYWDDDK |
| 10 | ISSSGDPT |
| 11 | GFSLSTYGMG |
| 12 | KSVSTSGYSY |
| 13 | GFSLSTSGMG |
| 14 | QSVDYNGDSY |
| 15 | GGSIRSGGYY |
| 16 | KSVSTSGYNY |
| 17 | GYSITSDYA |
| 18 | SRDVGGYNY |
| 19 | GYSITSDFA |
| 20 | SSNIGAGYD |
| 21 | GYSISSDYA |
| 22 | GFSLSTSGMS |
| 23 | GFSLSTYGVG |
| 24 | GFSLTTYGMG |

TABLE 12-continued

| SEQ ID NO: | SEQUENCE |
|---|---|
| 25 | GFSIRTSKVG |
| 26 | GFSLSDFGVG |
| 27 | ARRTTTADYFAY |
| 28 | ARLGSDYDVWFDY |
| 29 | ARRAPFYGNHAMDY |
| 30 | VRRAHTTVLGDWFAY |
| 31 | ARTLRVSGDYVRDFDL |
| 32 | ARRGFYGRKYEVNHFDY |
| 33 | ARRTFSYYYGSSFYYFDN |
| 34 | AHRRGPTTLFGVPIARGPVNAMDV |
| 35 | VQEGYIY |
| 36 | QHSRELLT |
| 37 | TLYYGSVDY |
| 38 | QQSNEDPFT |
| 39 | ARLDGYTLDI |
| 40 | LYSREFPPWT |
| 41 | ARGWPLAY |
| 42 | WSFAGSYYV |
| 43 | ATAGRGFPY |
| 44 | QSYDSSLSGSV |
| 45 | ASYDDYTWFTY |
| 46 | ARGYYGSSHSPV |
| 47 | ARRAPFYGNHAMDY |
| 48 | APELLGGPSC FLFPPKPKDT LMISRTPEVT CVVVDVSHED PEVKFNWYVD GVEVHNAKTK PREEQYNSTY RVVSVLTVLH QDWLNGKEYK CKVSNKALPA PCEKTISKAK GQ |
| 49 | APELLGGPCV FLFPPKPKDT LMISRTPEVT CVVVDVSHED PEVKFNWYVD GVEVHNAKTK PREEQYNSTY RVVSVLTVLH QDWLNGKEYK CKVSNKALPA PCEKTISKAK GQ |
| 50 | APELLGGPSV FLFCPKPKDT LMISRTPEVT CVVVDVSHED PEVKFNWYVD GVEVHNAKTK PREEQYNSTY RVVSVLTVLH QDWLNGKEYK CKVSNKALPA PIEKTCSKAK GQ |
| 51 | APELLGGPSV FCFPPKPKDT LMISRTPEVT CVVVDVSHED PEVKFNWYVD GVEVHNAKTK PREEQYNSTY RVVSVLTVLH QDWLNGKEYK CKVSNKALPA PIECTISKAK GQ |
| 52 | APELLGGPSC FLFPPKPKDT LMISRTPEVT CVVVDVSHED PEVKFNWYVD GVEVHNAKTK PREEQYNSTY RVVSVLTVLH QDWLNGKEYK CKVSNKALPA PIECTISKAK GQ |
| 53 | APELLGGPSV FLFPPKPKDT LMISRTPEVT CVVVDVSHED PEVKFNWYVD GVEVHNAKTK PRCEQYNSTY CVVSVLTVLH QDWLNGKEYK CKVSNKALPA PIEKTISKAK GQ |
| 54 | GGPSV FLFPPKPKDT LMISRTPEVT CVVVDVSHED PEVKFNWYVD GVEVHNAKTK PREEHNTY RVVSVLTVLH QDWLNGKEYK CKVSNKALPA PIEKTISKAK GQ |
| 55 | GGPSV FLFPPKPKDT LMISRTPEVT CVVVDVSHED PEVKFNWYVD GVEVHNAKTK PREEAASTY RVVSVLTVLH QDWLNGKEYK CKVSNKALPA PIEKTISKAK GQ |

TABLE 12-continued

| SEQ ID NO: | SEQUENCE |
|---|---|
| 56 | GGPSV FLFPPKPKDT LMISRTPEVT CVVVDVSHED PEVKFNWYVD GVEVHNAKTK PREEYDTSTY RVVSVLTVLH QDWLNGKEYK CKVSNKALPA PIEKTISKAK GQ |
| 57 | GGPSV FLFPPKPKDT LMISRTPEVT CVVVDVSHED PEVKFNWYVD GVEVHNAKTK PRVYPGSITY RVVSVLTVLH QDWLNGKEYK CKVSNKALPA PIEKTISKAK GQ |
| 58 | GGPSV FLFPPKPKDT LMISRTPEVT CVVVDVSHED PEVKFNWYVD GVEVHNAKTK PRIYWDDDKTY RVVSVLTVLH QDWLNGKEYK CKVSNKALPA PIEKTISKAK GQ |
| 59 | GGPSV FLFPPKPKDT LMISRTPEVT CVVVDVSHED PEVKFNWYVD GVEVHNAKTK PRISSSGDPTTY RVVSVLTVLH QDWLNGKEYK CKVSNKALPA PIEKTISKAK GQ |
| 60 | GGPSV FLFPPKPKDT LMISRTPEVT CVVVGFSLST YGMGFNWYVD GVEVHNAKTK PREEQYNSTY RVVSVLTVLH QDWLNGKEYK CKVVQEGY IYEKTISKAK GQ |
| 61 | GGPSV FLFPPKPKDT LMISRTPEVT CVVVKSVSTS GYSYFNWYVD GVEVHNAKTK PREEQYNSTY RVVSVLTVLH QDWLNGKEYK CKVQHSREL LTEKTISKAK GQ |
| 62 | GGPSV FLFPPKPKDT LMISRTPEVT CVVVGFSLST SGMGFNWYVD GVEVHNAKTK PREEQYNSTY RVVSVLTVLH QDWLNGKEYK CKVTLYYGSV DYEKTISKAK GQ |
| 63 | GGPSV FLFPPKPKDT LMISRTPEVT CVVVQSVDYN GDSYFNWYVD GVEVHNAKTK PREEQYNSTY RVVSVLTVLH QDWLNGKEYK CKVQQSNEDP FTEKTISKAK GQ |
| 64 | GGPSV FLFPPKPKDT LMISRTPEVT CVVVGGSIRS GGYYFNWYVD GVEVHNAKTK PREEQYNSTY RVVSVLTVLH QDWLNGKEYK CKVARLDGYTL DIEKTISKAK GQ |
| 65 | GGPSV FLFPPKPKDT LMISRTPEVT CVVVKSVSTS GYNYFNWYVD GVEVHNAKTK PREEQYNSTY RVVSVLTVLH QDWLNGKEYK CKVLYSREFPP WTEKTISKAK GQ |
| 66 | GGPSV FLFPPKPKDT LMISRTPEVT CVVVGYSITS DYAFNWYVD GVEVHNAKTK PREEQYNSTY RVVSVLTVLH QDWLNGKEYK CKVARGWPL AYEKTISKAK GQ |
| 67 | GGPSV FLFPPKPKDT LMISRTPEVT CVVVSRDVGG YNYFNWYVD GVEVHNAKTK PREEQYNSTY RVVSVLTVLH QDWLNGKEYK CKVWSFAGSY YVEKTISKAK GQ |
| 68 | GGPSV FLFPPKPKDT LMISRTPEVT CVVVGYSITS DFAFNWYVD GVEVHNAKTK PREEQYNSTY RVVSVLTVLH QDWLNGKEYK CKVATAGRGF PYEKTISKAK GQ |
| 69 | GGPSV FLFPPKPKDT LMISRTPEVT CVVVSSNIGA GYDFNWYVD GVEVHNAKTK PREEQYNSTY RVVSVLTVLH QDWLNGKEYK CKVQSYDSSLSG SVEKTISKAK GQ |
| 70 | GGPSV FLFPPKPKDT LMISRTPEVT CVVVGYSITS DYAFNWYVD GVEVHNAKTK PREEQYNSTY RVVSVLTVLH QDWLNGKEYK CKVASYDDYTWF TYEKTISKAK GQ |
| 71 | GGPSV FLFPPKPKDT LMISRTPEVT CVVVGYSISS DYAFNWYVD GVEVHNAKTK PREEQYNSTY RVVSVLTVLH QDWLNGKEYK CKVARGYYGSSHS PVEKTISKAK GQ |
| 72 | GGPSV FLFPPKPKDT LMISRTPEVT CVVVGFSLST SGMSFNWYVD GVEVHNAKTK PREEQYNSTY RVVSVLTVLH QDWLNGKEYK CKVARRTTTADYF AYEKTISKAK GQ |
| 73 | GGPSV FLFPPKPKDT LMISRTPEVT CVVVGFSLST YGVGFNWYVD GVEVHNAKTK PREEQYNSTY RVVSVLTVLH QDWLNGKEYK CKVARLGSDYDVWF DYEKTISKAK GQ |
| 74 | GGPSV FLFPPKPKDT LMISRTPEVT CVVVGFSLTT YGMGFNWYVD GVEVHNAKTK PREEQYNSTY RVVSVLTVLH QDWLNGKEYK CKVARRAPFY GNHAM DYEKTISKAK GQ |
| 75 | GGPSV FLFPPKPKDT LMISRTPEVT CVVVGFSLSTSGMGFNWYVD GVEVHNAKTK PREEQYNSTY RVVSVLTVLH QDWLNGKEYK CKVVRRAHTT VLGDWF AYEKTISKAK GQ |
| 76 | GGPSV FLFPPKPKDT LMISRTPEVT CVVVGFSLST SGMSFNWYVD GVEVHNAKTK PREEQYNSTY RVVSVLTVLH QDWLNGKEYK CKVARTLRVS GDYVRDF DLEKTISKAK GQ |
| 77 | GGPSV FLFPPKPKDT LMISRTPEVT CVVVGFSIRT SKVGFNWYVD GVEVHNAKTK PREEQYNSTY RVVSVLTVLH QDWLNGKEYK CKVARRGFYG RKYEVNHF DYEKTISKAK GQ |
| 78 | GGPSV FLFPPKPKDT LMISRTPEVT CVVVGFSLST SGMGFNWYVD GVEVHNAKTK PREEQYNSTYRVVSVLTVLHQDWLNGKEYK CKVARRTFSY YYGSSFYYF DNEKTISKAK GQ |

TABLE 12-continued

| SEQ ID NO: | SEQUENCE |
|---|---|
| 79 | GGPSV FLFPPKPKDT LMISRTPEVT CVVVGFSLSD FGVGFNWYVD GVEVHNAKTK PREEQYNSTY RVVSVLTVLH QDWLNGKEYK CKVAHRRGPT TLFGVPIARG PVNAM DVEKTISKAK GQ |
| 80 | GGPSV FLFPPKPKDT LMISRTPEVT CVVVARRTTT ADYFAYFNWYVD GVEVHNAKTK PREEQYNSTY RVVSVLTVLH QDWLNGKEYK CKVGFSLSTSG MSEKTISKAK GQ |
| 81 | GGPSV FLFPPKPKDT LMISRTPEVT CVVVARLGSD YDVWFDYFNWYVD GVEVHNAKTK PREEQYNSTY RVVSVLTVLH QDWLNGKEYK CKVGFSLSTYG VGEKTISKAK GQ |
| 82 | GGPSV FLFPPKPKDT LMISRTPEVT CVVVARRAPF YGNHAMDYFNWYVD GVEVHNAKTK PREEQYNSTY RVVSVLTVLH QDWLNGKEYK CKVGFSLTTYG MGEKTISKAK GQ |
| 83 | GGPSV FLFPPKPKDT LMISRTPEVT CVVVVRRAHT TVLGDWFAYFNWYVD GVEVHNAKTK PREEQYNSTY RVVSVLTVLH QDWLNGKEYK CKVGFSLSTSG MGEKTISKAK GQ |
| 84 | GGPSV FLFPPKPKDT LMISRTPEVT CVVVARTLRV SGDYVRDFDLFNWYVD GVEVHNAKTK PREEQYNSTY RVVSVLTVLH QDWLNGKEYK CKVGFSLSTSG MSEKTISKAK GQ |
| 85 | GGPSV FLFPPKPKDT LMISRTPEVT CVVVARRGFY GRKYEVN HFDYFNWYVD GVEVHNAKTK PREEQYNSTY RVVSVLTVLH QDWLNGKEYK CKVGFSIRTSK VGEKTISKAK GQ |
| 86 | GGPSV FLFPPKPKDT LMISRTPEVT CVVVARRTFS YYYGSSFY YFDNFNWYVD GVEVHNAKTK PREEQYNSTY RVVSVLTVLH QDWLNGKEYK CKVGFSLSTSG MGEKTISKAK GQ |
| 87 | GGPSV FLFPPKPKDT LMISRTPEVT CVVVAHRRGP TTLFGVPIARGPVN AMDVFNWYVD GVEVHNAKTK PREEQYNSTY RVVSVLTVLH QDWLNGKEYK CKVGFSLSDFG VGEKTISKAK GQ |
| 88 | GGPSV FLFPPKPKDT LMISRTPEVT CVVVSNKAL PAPIFNWYVD GVEVHNAKTK PREEQYNSTY RVVSVLTVLH QDWLNGKEYK CKVDVSHEDPE VKEKTISKAK GQ |
| 89 | HHHHHH APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK |
| 90 | HHHHHH GSGSCDKTHT APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK |
| 91 | HHHHH PSV FCFPPKPKDT LMISRTPEVT CVVVDVSHED PEVKFNWYVD GVEVHNAKTK PREEQYNSTY RVVSVLTVLH QDWLNGKEYK CKVSNKALPA PIECTISKAK |
| 92 | MKKIWLALAGLVLAFSASAAGYE DGKGHHHHHH APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQ |
| 93 | MKKIWLALAGLVLAFSASAAGYE DGKGHHHHHH APELLGGPSV FLFPPKPKDT LMISRTPEVT CVVVDVSHED PEVKFNWYVD GVEVHNAKTK PREEHNTY RVVSVLTVLH QDWLNGKEYK CKVSNKALPA PIEKTISKAK GQ |
| 94 | MKKIWLALAGLVLAFSASAAGYE DGKGHHHHHH APELLGGPSV FLFPPKPKDT LMISRTPEVT CVVVDVSHED PEVKFNWYVD GVEVHNAKTK PREEAASTY RVVSVLTVLH QDWLNGKEYK CKVSNKALPA PIEKTISKAK GQ |
| 95 | MKKIWLALAGLVLAFSASAAGYE DGKGHHHHHH APELLGGPSV FLFPPKPKDT LMISRTPEVT CVVVDVSHED PEVKFNWYVD GVEVHNAKTK PREEYDTSTY RVVSVLTVLH QDWLNGKEYK CKVSNKALPA PIEKTISKAK GQ |
| 96 | MKKIWLALAGLVLAFSASAAGYE DGKGHHHHHHAPELL GGPSVFLFPPKPKDTLMISRTPEVTCVVV DVSHEDPEVK FNWYVDGVEVHNAKTKPR VYPGSI TYRVVSVLTVLHQDWLNGKEYKCKV SNKALPAPI EKTISKAKGQ |
| 97 | MKKIWLALAGLVLAFSASAAGYE DGKGHHHHHHAPELL GGPSVFLFPPKPKDTLMISRTPEVTCVVV DVSHEDPEVK FNWYVDGVEVHNAKTKPR IYWDDDK TYRVVSVLTVLHQDWLNGKEYKCKV SNKALPAPI EKTISKAKGQ |

TABLE 12-continued

| SEQ ID NO: | SEQUENCE |
|---|---|
| 98 | MKKIWLALAGLVLAFSASAAGYE DGKGHHHHHHAPELL GGPSVFLFPPKPKDTLMISRTPEVTCVVV DVSHEDPEVK FNWYVDGVEVHNAKTKPR ISSSGDPT TYRVVSVLTVLHQDWLNGKEYKCKV SNKALPAPI EKTISKAKGQ |
| 99 | MKKIWLALAGLVLAFSASAAGYE DGKGHHHHHHAPELL GGPSVFLFPPKPKDTLMISRTPEVTCVVV GFSLSTYGMG FNWYVDGVEVHNAKTKPR EEQYNS TYRVVSVLTVLHQDWLNGKEYKCKV VQEGYIY EKTISKAKGQ |
| 100 | MKKIWLALAGLVLAFSASAAGYE DGKGHHHHHHAPELL GGPSVFLFPPKPKDTLMISRTPEVTCVVV KSVSTSGYSY FNWYVDGVEVHNAKTKPR EEQYNS TYRVVSVLTVLHQDWLNGKEYKCKV QHSRELLT EKTISKAKGQ |
| 101 | MKKIWLALAGLVLAFSASAAGYE DGKGHHHHHHAPELL GGPSVFLFPPKPKDTLMISRTPEVTCVVV GFSLSTSGMG FNWYVDGVEVHNAKTKPR EEQYNS TYRVVSVLTVLHQDWLNGKEYKCKV TLYYGSVDY EKTISKAKGQ |
| 102 | MKKIWLALAGLVLAFSASAAGYE DGKGHHHHHHAPELL GGPSVFLFPPKPKDTLMISRTPEVTCVVV QSVDYNGDSY FNWYVDGVEVHNAKTKPR EEQYNS TYRVVSVLTVLHQDWLNGKEYKCKV QQSNEDPFT EKTISKAKGQ |
| 103 | MKKIWLALAGLVLAFSASAAGYE DGKGHHHHHHAPELL GGPSVFLFPPKPKDTLMISRTPEVTCVVV GGSIRSGGYY FNWYVDGVEVHNAKTKPR EEQYNS TYRVVSVLTVLHQDWLNGKEYKCKV ARLDGYTLDI EKTISKAKGQ |
| 104 | MKKIWLALAGLVLAFSASAAGYE DGKGHHHHHHAPELL GGPSVFLFPPKPKDTLMISRTPEVTCVVV KSVSTSGYNY FNWYVDGVEVHNAKTKPR EEQYNS TYRVVSVLTVLHQDWLNGKEYKCKV LYSREFPPWT EKTISKAKGQ |
| 105 | MKKIWLALAGLVLAFSASAAGYE DGKGHHHHHHAPELL GGPSVFLFPPKPKDTLMISRTPEVTCVVV GYSITSDYA FNWYVDGVEVHNAKTKPR EEQYNS TYRVVSVLTVLHQDWLNGKEYKCKV ARGWPLAY EKTISKAKGQ |
| 106 | MKKIWLALAGLVLAFSASAAGYE DGKGHHHHHHAPELL GGPSVFLFPPKPKDTLMISRTPEVTCVVV SRDVGGYNY FNWYVDGVEVHNAKTKPR EEQYNS TYRVVSVLTVLHQDWLNGKEYKCKV WSFAGSYYV EKTISKAKGQ |
| 107 | MKKIWLALAGLVLAFSASAAGYE DGKGHHHHHHAPELL GGPSVFLFPPKPKDTLMISRTPEVTCVVV GYSITSDFA FNWYVDGVEVHNAKTKPR EEQYNS TYRVVSVLTVLHQDWLNGKEYKCKV ATAGRGFPY EKTISKAKGQ |
| 108 | MKKIWLALAGLVLAFSASAAGYE DGKGHHHHHHAPELL GGPSVFLFPPKPKDTLMISRTPEVTCVVV SSNIGAGYD FNWYVDGVEVHNAKTKPR EEQYNS TYRVVSVLTVLHQDWLNGKEYKCKV QSYDSSLSGSV EKTISKAKGQ |
| 109 | MKKIWLALAGLVLAFSASAAGYE DGKGHHHHHHAPELL GGPSVFLFPPKPKDTLMISRTPEVTCVVV GYSITSDYA FNWYVDGVEVHNAKTKPR EEQYNS TYRVVSVLTVLHQDWLNGKEYKCKV ASYDDYTWFTY EKTISKAKGQ |
| 110 | MKKIWLALAGLVLAFSASAAGYE DGKGHHHHHHAPELL GGPSVFLFPPKPKDTLMISRTPEVTCVVV GYSISSDYA FNWYVDGVEVHNAKTKPR EEQYNS TYRVVSVLTVLHQDWLNGKEYKCKV ARGYYGSSHSPV EKTISKAKGQ |
| 111 | MKKIWLALAGLVLAFSASAAGYE DGKGHHHHHHAPELL GGPSVFLFPPKPKDTLMISRTPEVTCVVV GFSLSTSGMS FNWYVDGVEVHNAKTKPR EEQYNS TYRVVSVLTVLHQDWLNGKEYKCKV ARRTTTADYFAY EKTISKAKGQ |
| 112 | MKKIWLALAGLVLAFSASAAGYE DGKGHHHHHHAPELL GGPSVFLFPPKPKDTLMISRTPEVTCVVV GFSLSTYGVG FNWYVDGVEVHNAKTKPR EEQYNS TYRVVSVLTVLHQDWLNGKEYKCKV ARLGSDYDVWFDY EKTISKAKGQ |

TABLE 12-continued

| SEQ ID NO: | SEQUENCE |
|---|---|
| 113 | MKKIWLALAGLVLAFSASAAGYE DGKGHHHHHHAPELL<br>GGPSVFLFPPKPKDTLMISRTPEVTCVVV GFSLTTYGMG<br>FNWYVDGVEVHNAKTKPR EEQYNS TYRVVSVLTVLHQDWLNGKEYKCKV<br>ARRAPFYGNHAMDY EKTISKAKGQ |
| 114 | MKKIWLALAGLVLAFSASAAGYE DGKGHHHHHHAPELL<br>GGPSVFLFPPKPKDTLMISRTPEVTCVVV GFSLSTSGMG<br>FNWYVDGVEVHNAKTKPR EEQYNS TYRVVSVLTVLHQDWLNGKEYKCKV<br>VRRAHTTVLGDWFAY EKTISKAKGQ |
| 115 | MKKIWLALAGLVLAFSASAAGYE DGKGHHHHHHAPELL<br>GGPSVFLFPPKPKDTLMISRTPEVTCVVV GFSLSTSGMS<br>FNWYVDGVEVHNAKTKPR EEQYNS TYRVVSVLTVLHQDWLNGKEYKCKV<br>ARTLRVSGDYVRDFDL EKTISKAKGQ |
| 116 | MKKIWLALAGLVLAFSASAAGYE DGKGHHHHHHAPELL<br>GGPSVFLFPPKPKDTLMISRTPEVTCVVV GFSIRTSKVG<br>FNWYVDGVEVHNAKTKPR EEQYNS TYRVVSVLTVLHQDWLNGKEYKCKV<br>ARRGFYGRKYEVNHFDY EKTISKAKGQ |
| 117 | MKKIWLALAGLVLAFSASAAGYE DGKGHHHHHHAPELL<br>GGPSVFLFPPKPKDTLMISRTPEVTCVVV GFSLSTSGMG<br>FNWYVDGVEVHNAKTKPR EEQYNS TYRVVSVLTVLHQDWLNGKEYKCKV<br>ARRTFSYYYGSSFYYFDN EKTISKAKGQ |
| 118 | MKKIWLALAGLVLAFSASAAGYE DGKGHHHHHHAPELL<br>GGPSVFLFPPKPKDTLMISRTPEVTCVVV GFSLSDFGVG<br>FNWYVDGVEVHNAKTKPR EEQYNS TYRVVSVLTVLHQDWLNGKEYKCKV<br>AHRRGPTTLFGVPIARGPVNAMDV EKTISKAKGQ |
| 119 | MKKIWLALAGLVLAFSASAAGYE DGKGHHHHHHAPELL<br>GGPSVFLFPPKPKDTLMISRTPEVTCVVV ARRTTTADYFAY<br>FNWYVDGVEVHNAKTKPR EEQYNS TYRVVSVLTVLHQDWLNGKEYKCKV<br>GFSLSTSGMS EKTISKAKGQ |
| 120 | MKKIWLALAGLVLAFSASAAGYE DGKGHHHHHHAPELL<br>GGPSVFLFPPKPKDTLMISRTPEVTCVVV ARLGSDYDVWFDY<br>FNWYVDGVEVHNAKTKPR EEQYNS TYRVVSVLTVLHQDWLNGKEYKCKV<br>GFSLSTYGVG EKTISKAKGQ |
| 121 | MKKIWLALAGLVLAFSASAAGYE DGKGHHHHHHAPELL<br>GGPSVFLFPPKPKDTLMISRTPEVTCVVV ARRAPFYGNHAMDY<br>FNWYVDGVEVHNAKTKPR EEQYNS TYRVVSVLTVLHQDWLNGKEYKCKV<br>GFSLTTYGMG EKTISKAKGQ |
| 122 | MKKIWLALAGLVLAFSASAAGYE DGKGHHHHHHAPELL<br>GGPSVFLFPPKPKDTLMISRTPEVTCVVV VRRAHTTVLGDWFAY<br>FNWYVDGVEVHNAKTKPR EEQYNS TYRVVSVLTVLHQDWLNGKEYKCKV<br>GFSLSTSGMG EKTISKAKGQ |
| 123 | MKKIWLALAGLVLAFSASAAGYE DGKGHHHHHHAPELL<br>GGPSVFLFPPKPKDTLMISRTPEVTCVVV ARTLRVSGDYVRDFDL<br>FNWYVDGVEVHNAKTKPR EEQYNS TYRVVSVLTVLHQDWLNGKEYKCKV<br>GFSLSTSGMS EKTISKAKGQ |
| 124 | MKKIWLALAGLVLAFSASAAGYE DGKGHHHHHHAPELL<br>GGPSVFLFPPKPKDTLMISRTPEVTCVVV ARRGFYGRKYEVNHFDY<br>FNWYVDGVEVHNAKTKPR EEQYNS TYRVVSVLTVLHQDWLNGKEYKCKV<br>GFSIRTSKVG EKTISKAKGQ |
| 125 | MKKIWLALAGLVLAFSASAAGYE DGKGHHHHHHAPELL<br>GGPSVFLFPPKPKDTLMISRTPEVTCVVV ARRTFSYYYGSSFYYFDN<br>FNWYVDGVEVHNAKTKPR EEQYNS TYRVVSVLTVLHQDWLNGKEYKCKV<br>GFSLSTSGMG EKTISKAKGQ |
| 126 | MKKIWLALAGLVLAFSASAAGYE DGKGHHHHHHAPELL<br>GGPSVFLFPPKPKDTLMISRTPEVTCVVV AHRRGPTTLFGVPIARGPVNAMDV<br>FNWYVDGVEVHNAKTKPR EEQYNS TYRVVSVLTVLHQDWLNGKEYKCKV<br>GFSLSDFGVG EKTISKAKGQ |
| 127 | MKKIWLALAGLVLAFSASAAGYE DGKGHHHHHHAPELL<br>GGPSVFLFPPKPKDTLMISRTPEVTCVVV SNKALPAPI<br>FNWYVDGVEVHNAKTKPR CEQYNS TYCVVSVLTVLHQDWLNGKEYKCKV<br>DVSHEDPEVK EKTISKAKGQ |

TABLE 12-continued

| SEQ ID NO: | SEQUENCE |
|---|---|
| 128 | MKKIWLALAGLVLAFSASAAGYE DGKGHHHHHHAPELL GGPSVFLFPPKPKDTLMISRTPEVTCVVV SNKALPAPI FNWYVDGVEVHNAKTKPR EEQYNS TYRVVSVLTVLHQDWLNGKEYKCKV DVSHEDPEVK EKTISKAKGQ |
| 129 | MKKIWLALAGLVLAFSASAAGYE DGKGHHHHHHAPELL GGPSCFLFPPKPKDTLMISRTPEVTCVVV DVSHEDPEVK FNWYVDGVEVHNAKTKPR EEQYNS TYRVVSVLTVLHQDWLNGKEYKCKV SNKALPAPIC EKTISKAKGQ |
| 130 | MKKIWLALAGLVLAFSASAAGYE DGKGHHHHHHAPELL GGPSCFLFPPKPKDTLMISRTPEVTCVVV DVSHEDPEVK FNWYVDGVEVHNAKTKPR EEQYNS TYRVVSVLTVLHQDWLNGKEYKCKV SNKALPAPC EKTISKAKGQ |
| 131 | MKKIWLALAGLVLAFSASAAGYE DGKGHHHHHHAPELL GGPCVFLFPPKPKDTLMISRTPEVTCVVV DVSHEDPEVK FNWYVDGVEVHNAKTKPR EEQYNS TYRVVSVLTVLHQDWLNGKEYKCKV SNKALPAPIC EKTISKAKGQ |
| 132 | MKKIWLALAGLVLAFSASAAGYE DGKGHHHHHHAPELL GGPCVFLFPPKPKDTLMISRTPEVTCVVV DVSHEDPEVK FNWYVDGVEVHNAKTKPR EEQYNS TYRVVSVLTVLHQDWLNGKEYKCKV SNKALPAPC EKTISKAKGQ |
| 133 | MKKIWLALAGLVLAFSASAAGYE DGKGHHHHHHAPELL GGPSVFLFCPKPKDTLMISRTPEVTCVVV DVSHEDPEVK FNWYVDGVEVHNAKTKPR EEQYNS TYRVVSVLTVLHQDWLNGKEYKCKV SNKALPAPI EKTICSKAKGQ |
| 134 | MKKIWLALAGLVLAFSASAAGYE DGKGHHHHHHAPELL GGPSVFLFCPKPKDTLMISRTPEVTCVVV DVSHEDPEVK FNWYVDGVEVHNAKTKPR EEQYNS TYRVVSVLTVLHQDWLNGKEYKCKV SNKALPAPI EKTCSKAKGQ |
| 135 | MKKIWLALAGLVLAFSASAAGYE DGKGHHHHHHAPELL GGPSVFLFPPKPKDTLMISRTPEVTCVVV DVSHEDPEVK FNWYVDGVEVHNAKTKPR CEQYNS TYCVVSVLTVLHQDWLNGKEYKCKV SNKALPAPI EKTISKAKGQ |
| 136 | MKKIWLALAGLVLAFSASAAGYE DGKGHHHHHHAPELL GGPSVFCFPPKPKDTLMISRTPEVTCVVV DVSHEDPEVK FNWYVDGVEVHNAKTKPR EEQYNS TYRVVSVLTVLHQDWLNGKEYKCKV SNKALPAPI ECTISKAKGQ |
| 137 | MKKIWLALAGLVLAFSASAAGYE DGKGHHHHHHAPELL GGPSVFLFPPKPKDTLMISRTPEVTAVVV DVSHEDPEVK FNWYVDGVEVHNAKTKPR EEQYNS TYRVVSVLTVLHQDWLNGKEYKAKV SNKALPAPI EKTISKAKGQ |
| 138 | MKKIWLALAGLVLAFSASAAGYE DGKGHHHHHHAPELL GGPSVFCFPPKPKDTLYITREPEVTCVVV DVSHEDPEVK FNWYVDGVEVHNAKTKPR EEQYNS TYRVVSVLAVLHQDWLNGKEYKCKV SNKALPAPI ECTISKAKGQ |

The disclosures of the following U.S. Patents are incorporated in their entirety by reference herein: U.S. Patent Application No. 2007/0178082; U.S. Patent Application No. 2007/0135620.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the invention.

What is claimed is:

1. A CH2 domain template molecule, comprising the amino acid sequence of SEQ ID NO: 97.

* * * * *